United States Patent
Wunberg et al.

(10) Patent No.: US 8,598,157 B2
(45) Date of Patent: Dec. 3, 2013

(54) 5-ALKYNYL-PYRIDINES

(75) Inventors: Tobias Wunberg, Hinterbruehl (AT); Oliver Kraemer, Vienna (AT); Lars van der Veer, Alsbach-Hähnlein (DE)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 130 days.

(21) Appl. No.: 13/357,021

(22) Filed: Jan. 24, 2012

(65) Prior Publication Data
US 2013/0023519 A1    Jan. 24, 2013

(30) Foreign Application Priority Data

Jan. 26, 2011 (EP) .................................. 11152219
Jul. 15, 2011 (EP) .................................. 11174234

(51) Int. Cl.
*C07D 413/14* (2006.01)
*C07D 401/14* (2006.01)
*C07D 405/14* (2006.01)
*C07D 401/06* (2006.01)

(52) U.S. Cl.
USPC ...... 514/211.15; 544/122; 544/295; 544/324; 544/327; 540/544; 540/575

(58) Field of Classification Search
USPC .................................. 544/122, 323–331, 333
See application file for complete search history.

(56) References Cited

U.S. PATENT DOCUMENTS

2005/0245530 A1   11/2005   Borzilleri et al.

FOREIGN PATENT DOCUMENTS

| EP | 08161369.7 | * | 4/2010 |
|----|-----------|---|--------|
| WO | 2006044823 | A2 | 4/2006 |
| WO | 2006082371 | A1 | 8/2006 |
| WO | 2006106721 | A1 | 10/2006 |

OTHER PUBLICATIONS

Waterson et al., Alkynyl pyrimidines as dual EGFR/ErbB2 kinase inhibitors, Bioorganic & Medicinal Chemistry Letters, Pergamon, Elsevier Science, GB, vol. 16, No. 9, May 1, 2006, pp. 2419-2422.

International Search Report, Form PCT/ISR/210, and Written Opinion, Form PCT/ISR/237, for cooresponding application PCT/EP2012/051167, Date of mailing Mar. 16, 2012.

European Search Report for cooresponding application EP 11174234.2, Dec. 15, 2011.

* cited by examiner

*Primary Examiner* — Samantha Shterengarts
*Assistant Examiner* — Amanda L Aguirre
(74) *Attorney, Agent, or Firm* — Michael P. Morris; Alan R. Stempel

(57)   ABSTRACT

5-alkynyl-pyridine of general formula (I)

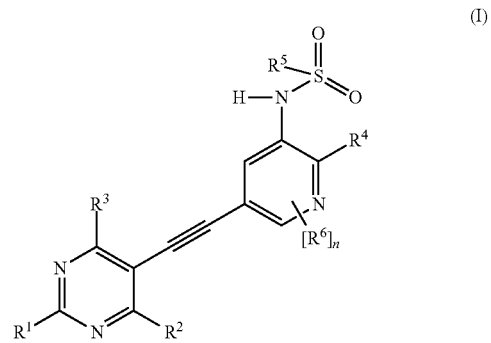

their use as inhibitors of the activity of PI3Kalpha, pharmaceutical compositions containing them, and their use as a medicaments for the treatment and/or prevention of diseases characterized by excessive or abnormal cell proliferation and associated conditions such as cancer.

The groups $R^1$ to $R^6$ and n have the meanings given in the claims and in the specification.

14 Claims, No Drawings

5-ALKYNYL-PYRIDINES

This invention relates to 5-alkynyl-pyridine of general formula (I)

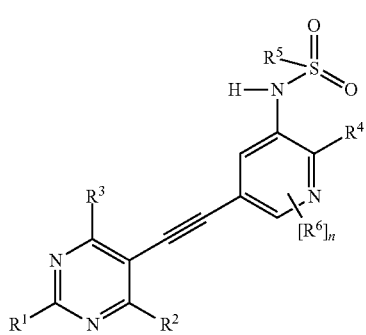

wherein the groups $R^1$ to $R^6$ and n have the meanings given below. The compounds of the invention are suitable for the treatment of diseases characterized by excessive or abnormal cell proliferation, pharmaceutical preparations containing such compounds and their use as medicaments. The compounds of the invention exhibit an inhibitory effect on PI3Kalpha activity.

BACKGROUND OF THE INVENTION

Cell proliferation is the increase in cell numbers as a result of cell growth and division. Generally, cells do not proliferate unless they receive signals that instruct them to do so. In the latter case, complex signal transduction networks are initiated within the cell.

The phosphoinositide 3-kinase pathway is one of the key pathways activated during cell proliferation. Phosphoinositide 3-kinase (PI3-kinase or PI3K) phosphorylates phosphatidylinositol 4,5-bisphosphate (PIP2) on the 3'OH position to produce phopsphatidylinositol (3,4,5)-triphosphate (PI(3,4,5)P3 or PIP3). The tumor suppressor phosphatase and tensin homolog deleted on chromosome 10 (PTEN) dephosphoryates PIP3 to PIP2, thereby terminating PI3K-dependent signaling. PIP3 propagates intracellular signaling leading to the proliferation of the cell.

In particular, the PI3K pathway is implicated in a variety of physiological and pathological functions operative in various human diseases such as cancer, metabolic, inflammatory and cardiovascular diseases (Wymann M P, Nat Rev Mol Cell Biol. 2008 February; 9 (2):162-76., Wymann M P, Curr Opin Cell Biol. 2005 April; 17(2):141-9).

Of the three classes of PI3Ks grouped according to structure and function, Class IA PI3K is the one most implicated in human cancer. It consists of three isoforms, named PI3Kalpha, -beta and -delta, wherein the role of PI3Kalpha as a central signaling molecule downstream of receptor tyrosine kinases (RTKs) and its involvement, in tumorigenesis, growth control and cellular survival has been demonstrated. In fact, activation of the signaling pathway by mutation or amplification of PI3Kalpha or mutation/deletion of the phosphatase PTEN (the most important negative regulator of the pathway) has been found in a large proportion of cancers of different origin. (I. Vivanco & C. L. Sawyers, Nature Reviews 2002, 2:489-501).

Inhibition of PI3K signaling can diminish cell proliferation, and in some circumstances, promote cell death. As a consequence, components of this pathway present attractive targets for cancer therapeutics and likewise inhibitors targeting this pathway are interesting candidates for the treatment of cancer.

Examples of PI3K inhibitors are disclosed in WO 2006/044823, WO 2006/040279 and WO 2009/112565. Nevertheless, there is a need to provide compounds acting as inhibitors of the PI3K pathway.

Thus, the technical problem underlying the present invention is to provide inhibitors useful in the prevention and/or treatment of diseases characterized by excessive or abnormal cell proliferation, such as cancer.

DETAILED DESCRIPTION OF THE INVENTION

The present invention addresses this need and thus provides, as a solution to the technical problem, the compounds according to formula (I)

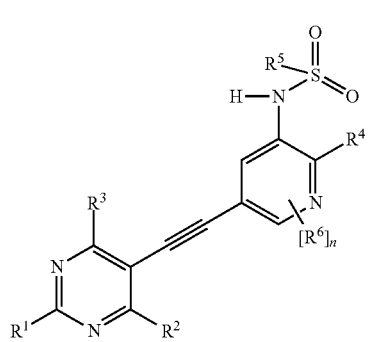

wherein $R^1$ to $R^6$ and n are as defined below. The compounds according to formula (I) inhibit specific signal enzymes which are involved in controlling the proliferation of cells. Thus, the compounds of the invention may be used for example for the treatment of diseases which are connected with the activity of these signal enzymes and are characterized by excessive or abnormal cell proliferation. Preferably, the compounds of the invention can be used in the treatment of cancer.

In more detail, the compounds of the invention are characterized by a powerful inhibitory effect of the PI3K pathway and high efficacy against tumor cells, particularly against those mediated through inhibiting PI3K.

The present invention therefore relates to compounds of general formula (I)

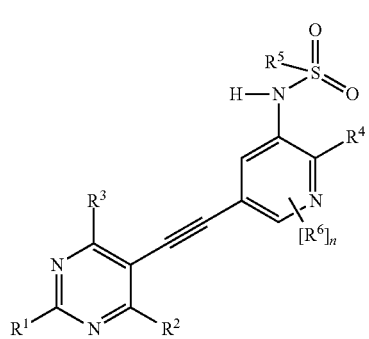

wherein
$R^1$ is —H or —NH$_2$;
$R^2$ is —N(R$^7$, R$^8$);

$R^3$ is —$C_{1-5}$alkyl;

$R^4$ is selected from —H, halogen, —CN, —$C_{1-5}$alkyl, —O—$C_{1-5}$alkyl, —$C_{1-5}$alkyl-O—$C_{1-5}$alkyl or —O—$C_{1-5}$-haloalkyl;

$R^5$ is selected from —$C_{1-5}$alkyl, —$C_{2-5}$alkenyl, —$C_{2-5}$alkynyl, —$C_{3-10}$cycloalkyl, 3-14 membered heterocyclyl, all of which groups can be optionally and independently substituted with one or more =O, —CN, =S, halogen, $R^{15}$ or $R^{16}$ or $R^5$ is selected from —$C_{6-10}$aryl or 5-12 membered heteroaryl, all of which groups can be optionally and independently substituted with one or more —CN, halogen, $R^{15}$ or $R^{16}$;

or $R^5$ is —N($R^{12}$,$R^{13}$);

$R^6$ is selected from halogen, —CN, —$C_{1-5}$alkyl, —$C_{1-5}$-haloalkyl, —O—$C_{1-5}$alkyl, —$C_{1-5}$alkyl-O—$C_{1-5}$alkyl or —O—$C_{1-5}$-haloalkyl;

n is 0, 1 or 2;

$R^7$ is selected from —H, —$C_{1-5}$alkyl, —$C_{2-5}$alkenyl, —$C_{2-5}$alkynyl, —$C_{3-10}$cycloalkyl, 3-14 membered heterocyclyl, —$C_{1-5}$alkyl-O—$R^9$, —$C_{1-5}$alkyl-S—$R^9$, or —$C_{1-5}$alkyl-N($R^9$,$R^{10}$), all of which groups can be optionally and independently substituted with one or more =O, —CN, =S, halogen, or $R^{11}$, $R^8$ is selected from —O—$C_{1-5}$alkyl, —S—$C_{1-5}$alkyl, —$C_{1-5}$alkyl, —$C_{2-5}$alkenyl, —$C_{2-5}$alkynyl, —$C_{3-10}$cycloalkyl, 3-14 membered heterocyclyl, —$C_{1-5}$alkyl-O—$R^9$, —$C_{1-5}$alkyl-S—$R^9$, or —$C_{1-5}$alkyl-N($R^9$,$R^{10}$), all of which groups can be optionally and independently substituted with one or more =O, —CN, =S, halogen, or $R^{11}$ or $R^7$, $R^8$ are the same or different, independently selected from —$C_{6-10}$aryl, 5-12 membered heteroaryl, all of which groups can be optionally and independently substituted with one or more —CN, halogen, or $R^{11}$, or $R^7$ and $R^8$ taken together with the nitrogen atom to which they are attached form a partially or fully saturated 3-14 membered heterocyclyl which group can be optionally and independently substituted with one or more =O, —CN, =S, halogen, or $R^{11}$;

$R^9$ is selected from —H, —$C_{1-5}$alkyl, —$C_{2-5}$alkenyl, —$C_{2-5}$alkynyl, —$C_{3-10}$cycloalkyl, 3-14 membered heterocyclyl, —$C_{1-5}$alkyl-O—$C_{1-5}$alkyl, —$C_{1-5}$alkyl-S—$C_{1-5}$alkyl, or —$C_{1-5}$alkyl-N($C_{1-5}$alkyl, $C_{1-5}$alkyl), all of which groups can be optionally and independently substituted with one or more =O, —CN, =S, halogen, or $R^{11}$, $R^{10}$ is selected from —H, —O—$C_{1-5}$alkyl, —$C_{1-5}$alkyl, —$C_{2-5}$alkenyl, —$C_{2-5}$alkynyl, —$C_{3-10}$cycloalkyl, 3-14 membered heterocyclyl, —$C_{1-5}$alkyl-O—$C_{1-5}$alkyl, —$C_{1-5}$alkyl-S—$C_{1-5}$alkyl or —$C_{1-5}$alkyl-N($C_{1-5}$alkyl, $C_{1-5}$alkyl), all of which groups can be optionally and independently substituted with one or more =O, —CN, =S, halogen, or $R^{11}$, or $R^9$, $R^{10}$ are the same or different, independently selected from —$C_{6-10}$aryl, 5-12 membered heteroaryl, all of which groups can be optionally and independently substituted with one or more —CN, halogen, or $R^{11}$, or $R^9$ and $R^{10}$ taken together with the atom to which they are attached form a 3-14 membered heterocyclyl which group can be optionally and independently substituted with one or more =O, —CN, =S, halogen, or $R^1$;

$R^{11}$ is selected from —OH, —$NH_2$, —$CF_3$, —$S(O)_2CH_3$, —$C(O)CH_3$, —$OCF_3$, —$OCHF_2$, or -nitro, or $R^{11}$ is selected from —$C_{6-10}$aryl or 5-12 membered heteroaryl, all of which groups can be optionally and independently substituted with one or more —CN, halogen, —OH, —$NH_2$, —$CH_3$, —$CH_2CH_3$, —$CF_3$, —$S(O)_2CH_3$, —$C(O)CH_3$, -propyl, -isopropyl, -cyclopropyl, -butyl, iso-butyl-, tert-butyl-, -cyclobutyl, -cyclopentyl, -cyclohexyl, —NH—$CH_3$, —N($CH_3$)$_2$, —N($CH_2CH_3$)$_2$, —NH—$CH_2CH_3$, —N($CH_3$, $CH_2CH_3$), —O—$CH_3$, —O—$CH_2CH_3$, —S—$CH_3$, —C(O)NH$CH_3$, —C(O)N($CH_3$)$_2$, —C(O)NH—$CH_2CH_3$, —C(O)N($CH_2CH_3$)$_2$, —C(O)-pyrazolidinyl, —$OCF_3$, —$OCHF_2$, -tetrahydrofuryl, -tetrahydropyranyl, —N-methylpiperazinlyl, -pyrrolidinyl, -morpholinyl or -nitro;

or $R^{11}$ is selected from —NH—$C_{1-5}$alkyl, —N($C_{1-5}$alkyl, $C_{1-5}$alkyl), —O—$C_{1-5}$alkyl, —S—$C_{1-5}$alkyl, —$C_{1-5}$alkyl, —$C_{2-5}$alkenyl, —$C_{2-5}$alkynyl, —$C_{3-10}$cycloalkyl, 3-14 membered heterocyclyl, optionally and independently substituted with one or more =O, —CN, =S, halogen, —OH, —$NH_2$, —$CH_3$, —$CH_2CH_3$, —$CF_3$, —$S(O)_2CH_3$, —$C(O)CH_3$, -propyl, -isopropyl, -cyclopropyl, -butyl, iso-butyl-, tert-butyl-, -cyclobutyl, -cyclopentyl, -cyclohexyl, —NH—$CH_3$, —N($CH_3$)$_2$, —N($CH_2CH_3$)$_2$, —NH—$CH_2CH_3$, —N($CH_3$, $CH_2CH_3$), —O—$CH_3$, —O—$CH_2CH_3$, —S—$CH_3$, —C(O)NH$CH_3$, —C(O)N($CH_3$)$_2$, —C(O)NH—$CH_2CH_3$, —C(O)N($CH_2CH_3$)$_2$, —C(O)-pyrazolidinyl, —$OCF_3$, —$OCHF_2$, -tetrahydrofuryl, -tetrahydropyranyl, —N-methylpiperazinlyl, -pyrrolidinyl, -morpholinyl or -nitro;

$R^{12}$ is selected from —H, —$C_{1-5}$alkyl, —$C_{2-5}$alkenyl, —$C_{2-5}$alkynyl, —$C_{3-10}$cycloalkyl, 3-14 membered heterocyclyl, —$C_{1-5}$alkyl-O—$C_{1-5}$alkyl, —$C_{1-5}$alkyl-S—$C_{1-5}$alkyl or —$C_{1-5}$alkyl-N($C_{1-5}$alkyl, $C_{1-5}$alkyl), all of which groups can be optionally and independently substituted with one or more =O, —CN, =S, halogen, or $R^{14}$.

$R^{13}$ is selected from —H, —O—$C_{1-5}$alkyl, —$C_{1-5}$alkyl, —$C_{2-5}$alkenyl, —$C_{2-5}$alkynyl, —$C_{3-10}$cycloalkyl, 3-14 membered heterocyclyl, —$C_{6-10}$aryl, 5-12 membered heteroaryl, —$C_{1-5}$alkyl-O—$C_{1-5}$alkyl, —$C_{1-5}$alkyl-S—$C_{1-5}$alkyl, or —$C_{1-5}$alkyl-N($C_{1-5}$alkyl, $C_{1-5}$alkyl), all of which groups can be optionally and independently substituted with one or more =O, —CN, =S, halogen, or $R^{14}$, or $R^{12}$, $R^{13}$ are the same or different, independently selected from —$C_{6-10}$aryl, 5-12 membered heteroaryl, all of which groups can be optionally and independently substituted with one or more —CN, halogen, or $R^{14}$, or $R^{12}$ and $R^{13}$ taken together with the nitrogen atom to which they are attached form a 3-14 membered heterocyclyl which group can be optionally and independently substituted with one or more =O, —CN, =S, halogen, or $R^{14}$;

$R^{14}$ is selected from —OH, —$NH_2$, —$CF_3$, —$OCF_3$, —$OCHF_2$, —$S(O)_2CH_3$, —$C(O)CH_3$ or -nitro, or $R^{14}$ is selected from —$C_{6-10}$aryl, 5-12 membered heteroaryl all of which groups can be optionally and independently substituted with one or more —CN, halogen, —OH, —$NH_2$, —$CH_3$, —$CH_2CH_3$, —$CF_3$, —$S(O)_2CH_3$, —$C(O)CH_3$, -propyl, -isopropyl, -cyclopropyl, -butyl, iso-butyl-, tert-butyl-, -cyclobutyl, -cyclopentyl, -cyclohexyl, —NH—$CH_3$, —N($CH_3$)$_2$, —N($CH_2CH_3$)$_2$, —NH—$CH_2CH_3$, —N($CH_3$,$CH_2CH_3$), —O—$CH_3$, —O—$CH_2CH_3$, —S—$CH_3$, —C(O)NH$CH_3$, —C(O)N($CH_3$)$_2$, —C(O)NH—$CH_2CH_3$, —C(O)N($CH_2CH_3$)$_2$, —C(O)-pyrazolidinyl, —$OCF_3$, —$OCHF_2$, -tetrahydrofuryl, -tetrahydropyranyl, —N-methylpiperazinlyl, -pyrrolidinyl, -morpholinyl or -nitro;

or $R^{14}$ is selected from —NH—$C_{1-5}$alkyl, —N($C_{1-5}$alkyl, $C_{1-5}$alkyl), —O—$C_{1-5}$alkyl, —S—$C_{1-5}$alkyl, —$C_{1-5}$ alkyl, —$C_{2-5}$alkenyl, —$C_{2-5}$alkynyl, —$C_{3-10}$cycloalkyl, 3-14 membered heterocyclyl, all of which groups can be optionally and independently substituted with one or more =O, —CN, =S, halogen, —H, —OH, —$NH_2$, —$CH_3$, —$CH_2CH_3$, —$CF_3$, —S(O)$_2CH_3$, —C(O)$CH_3$, -propyl, -isopropyl, -cyclopropyl, -butyl, iso-butyl-, tert-butyl-, -cyclobutyl, -cyclopentyl, -cyclohexyl, —NH—$CH_3$, —N($CH_3$)$_2$, —N($CH_2CH_3$)$_2$, —NH—$CH_2CH_3$, N($CH_3$,$CH_2CH_3$), —O—$CH_3$, —O—$CH_2CH_3$, —S—$CH_3$, —C(O)NH$CH_3$, —C(O)N($CH_3$)$_2$, —C(O)NH—$CH_2CH_3$, —C(O)N($CH_2CH_3$)$_2$, —C(O)-pyrazolidinyl, —$OCF_3$, —$OCHF_2$, -tetrahydrofuryl, -tetrahydropyranyl, —N-methylpiperazinly, -pyrrolidinyl, -morpholinyl or -nitro;

$R^{15}$ and $R^{16}$ are the same or different, independently selected from: —OH, —$NH_2$, —$CF_3$, —S(O)$_2CH_3$, —C(O)$CH_3$, —$OCF_3$, —$OCHF_2$ or -nitro, or $R^{15}$ and $R^{16}$ are the same or different, independently selected from:
—NH—$C_{1-5}$alkyl, —N($C_{1-5}$alkyl, $C_{1-5}$alkyl), —O—$C_{1-5}$alkyl, —S—$C_{1-5}$alkyl, —$C_{1-5}$alkyl, —$C_{2-5}$alkenyl, —$C_{2-5}$alkynyl, —$C_{3-10}$cycloalkyl, 3-14 membered heterocyclyl, all of which groups can be optionally and independently substituted with one or more =O, —CN, =S, halogen, —OH, —$NH_2$, —$CH_3$, —$CH_2CH_3$, —$CF_3$, —S(O)$_2CH_3$, —C(O)$CH_3$, -propyl, -isopropyl,
-cyclopropyl, -butyl, iso-butyl-, tert-butyl-, -cyclobutyl, -cyclopentyl, -cyclohexyl, —NH—$CH_3$, —N($CH_3$)$_2$, —N($CH_2CH_3$)$_2$, —NH—$CH_2CH_3$, —N($CH_3$,$CH_2CH_3$), —O—$CH_3$, —O—$CH_2CH_3$, —S—$CH_3$, —C(O)NH$CH_3$, —C(O)N($CH_3$)$_2$, —C(O)NH—$CH_2CH_3$, —C(O)N($CH_2CH_3$)$_2$, —C(O)-pyrazolidinyl, —$OCF_3$, —$OCHF_2$, -tetrahydrofuryl, -tetrahydropyranyl, —N-methylpiperazinly, -pyrrolidinyl, -morpholinyl or -nitro;

or $R^{15}$ and $R^{16}$ are the same or different, independently selected from —$C_{6-10}$aryl or 5-12 membered heteroaryl, all of which groups can be optionally and independently substituted with one or more —CN, halogen, —OH, —$NH_2$, —$CH_3$, —$CH_2CH_3$, —$CF_3$, —S(O)$_2CH_3$, —C(O)$CH_3$, -propyl, -isopropyl, -cyclopropyl, -butyl, iso-butyl-, tert-butyl-, -cyclobutyl, -cyclopentyl, -cyclohexyl, —NH—$CH_3$, —N($CH_3$)$_2$, —N($CH_2CH_3$)$_2$, —NH—$CH_2CH_3$, —N($CH_3$,$CH_2CH_3$), —O—$CH_3$, —O—$CH_2CH_3$, —S—$CH_3$, —C(O)NH$CH_3$, —C(O)N($CH_3$)$_2$, —C(O)NH—$CH_2CH_3$, —C(O)N($CH_2CH_3$)$_2$, —C(O)-pyrazolidinyl, —$OCF_3$, —$OCHF_2$, -tetrahydrofuryl, -tetrahydropyranyl, —N-methylpiperazinly, -pyrrolidinyl, -morpholinyl or -nitro;

or $R^{15}$ and $R^{16}$ taken together with the atom to which they are attached form a partially or fully saturated —$C_{3-10}$ cycloalkyl or 4-8 membered heterocyclyl all of which groups can be optionally and independently substituted with one or more =O, —CN, =S, halogen, —OH, —$NH_2$, —$CH_3$, —$CH_2CH_3$, —$CF_3$, —S(O)$_2CH_3$, —C(O)$CH_3$, -propyl, -isopropyl, -cyclopropyl, -butyl, iso-butyl-, tert-butyl-, -cyclobutyl, -cyclopentyl, -cyclohexyl, —NH—$CH_3$, —N($CH_3$)$_2$, —N($CH_2CH_3$)$_2$, —NH—$CH_2CH_3$, —N($CH_3$,$CH_2CH_3$), —O—$CH_3$, —O—$CH_2CH_3$, —S—$CH_3$, —C(O)NH$CH_3$, —C(O)N($CH_3$)$_2$, —C(O)NH—$CH_2CH_3$, —C(O)N($CH_2CH_3$)$_2$, —C(O)-pyrazolidinyl, —$OCF_3$, —$OCHF_2$, -tetrahydrofuryl, -tetrahydropyranyl, —N-methylpiperazinly, -pyrrolidinyl, -morpholinyl, or -nitro;

or salts thereof.

In one aspect the invention relates to compounds of formula (I), wherein $R^1$ is —H.

In another aspect the invention relates to compounds of formula (I), wherein $R^1$ is —$NH_2$.

In another aspect the invention relates to compounds of formula (I), wherein $R^3$ is —$C_{1-5}$alkyl, preferably —$C_{1-3}$ alkyl, more preferably —$CH_3$ or —$CH_2CH_3$.

In another aspect the invention relates to compounds of formula (I), wherein $R^4$ is selected from —H, halogen, —CN, —$C_{1-5}$alkyl, —O—$C_{1-5}$alkyl or —$C_{1-5}$alkyl-O—$C_{1-5}$alkyl or —O—$C_{1-5}$-haloalkyl. Preferably, $R^4$ is —H, —$C_{1-5}$alkyl or —O—$C_{1-5}$alkyl. Most preferred substitutents are —H, —$CH_3$ or —O—$CH_3$.

In another aspect the invention relates to compounds of formula (I), wherein n is 0.

In another aspect the invention relates to compounds of formula (I), wherein $R^6$ is selected from halogen, —CN, —$C_{1-5}$alkyl, —$C_{1-5}$-haloalkyl, —O—$C_{1-5}$alkyl, —$C_{1-5}$ alkyl-O—$C_{1-5}$alkyl or —O—$C_{1-5}$-haloalkyl. Preferably, $R^6$ is —$C_{1-5}$alkyl.

In another aspect the invention relates to compounds of formula (I), wherein $R^5$ is —$C_{1-5}$alkyl, —$C_{2-5}$alkenyl, —$C_{2-5}$ alkynyl, —$C_{3-10}$cycloalkyl, 3-14 membered heterocyclyl, or —N($R^{12}$,$R^{13}$), all of which groups can be optionally and independently substituted with one or more =O, —CN, =S, halogen, $R^{15}$ or $R^{16}$, wherein $R^{15}$ and $R^{16}$ are as defined above.

In another aspect the invention relates to compounds of formula (I), wherein $R^5$ is selected from —$C_{6-10}$aryl or 5-12 membered heteroaryl, all of which groups can be optionally and independently substituted with one or more —CN, halogen, $R^{15}$ or $R^{16}$, wherein $R^{15}$ and $R^{16}$ are as defined above.

In another aspect the invention relates to compounds of formula (I), wherein $R^5$ is —$C_{1-5}$alkyl, —$C_{3-10}$cycloalkyl, 3-14 membered heterocyclyl, all of which groups can be optionally and independently substituted with one or more =O, —CN, =S, halogen, $R^{15}$ or $R^{16}$, wherein $R^{15}$ and $R^{16}$ are as defined above.

In one aspect the invention relates to compounds of formula (I), wherein $R^5$ is selected from —$C_{1-5}$alkyl, preferably —$C_{1-3}$-alkyl, more preferably —$CH_3$, all of which groups can be optionally and independently substituted with one or more =O, —CN, =S, halogen, $R^{15}$ or $R^{16}$, wherein $R^{15}$ and $R^{16}$ are as defined above. In a further preferred embodiment $R^5$ is —$C_{1-5}$-alkyl substituted with one or —O—$C_{1-3}$alkyl, preferably —O—$CH_3$.

In one aspect the invention relates to compounds of formula (I), wherein $R^5$ is selected from —$C_{3-10}$cycloalkyl, preferably $R^5$ is —$C_{3-6}$cycloalkyl, more preferably cyclopropyl or cyclohexyl, all of which groups can be optionally and independently substituted with one or more =O, —CN, =S, halogen, $R^{15}$ or $R^{16}$, wherein $R^{15}$ and $R^{16}$ are as defined above.

In another aspect the invention relates to compounds of formula (I), wherein $R^5$ is —$C_{6-10}$-aryl, more preferably $R^5$ is phenyl, both of which can be optionally and independently substituted with one or more —CN, halogen, $R^{15}$ or $R^{16}$, wherein $R^{15}$ and $R^{16}$ are as defined above. In a further preferred embodiment $R^5$ is phenyl substituted with one or more halogen, more preferably, with one or more —F.

In another preferred embodiment, $R^5$ is phenyl substituted with one or more $R^{15}$ or $R^{16}$ wherein $R^{15}$ or $R^{16}$ is —O—$C_{1-5}$ alkyl, preferably —O—$CH_3$.

In one aspect the invention relates to compounds of formula (I), wherein $R^5$ is 5-12 membered heteroaryl, preferably $R^5$ is pyridinyl, imidazolyl, pyrrazolyl, thiophenyl, furyl, N-methyl-pyrazolyl, N-methyl-imidazolyl, all of which groups can be optionally and independently substituted with one or more —CN, halogen, $R^{15}$ or $R^{16}$, wherein $R^{15}$ and $R^{16}$ are as defined above.

When $R^5$ is 5-12 membered heteroaryl, the compounds show an improved solubility.

In a preferred embodiment, $R^5$ is 5-12 membered heteroaryl substituted with one or more —$C_{1-3}$alkyl, preferably —$CH_3$, or is substituted with halogen, preferably, —Cl.

In another aspect the invention relates to compounds of formula (I), wherein $R^5$ is —$N(R^{12},R^{13})$, wherein $R^{12}$ and $R^{13}$ are as defined below.

In a preferred embodiment $R^{12}$ and $R^{13}$ taken together with the nitrogen atom to which they are attached form a 3-14 membered heterocyclyl which group can be optionally and independently substituted with one or more =O, —CN, =S, halogen, or $R^{14}$, wherein $R^{14}$ is as defined above.

In a preferred embodiment, $R^5$ is pyrrolidinyl which group can be optionally and independently substituted with one or more =O, —CN, =S, halogen, or $R^{14}$, wherein $R^{14}$ is as defined above.

In one aspect the invention relates to compounds of formula (I), wherein $R^7$ is selected from —H, —$C_{1-5}$alkyl, —$C_{2-5}$alkenyl, —$C_{2-5}$alkynyl, —$C_{3-10}$cycloalkyl, 3-14 membered heterocyclyl, —$C_{1-5}$alkyl-O—$R^9$, —$C_{1-5}$alkyl-S—$R^9$, or —$C_{1-15}$alkyl-N($R^9,R^{10}$), all of which groups can be optionally and independently substituted with one or more =O, —CN, =S, halogen, or $R^{11}$, wherein $R^9$, $R^{10}$ and $R^{11}$ are as defined above.

In a preferred embodiment the invention relates to compounds of formula (I), wherein $R^7$ is selected from —H, —$C_{1-5}$alkyl, —$C_{3-10}$cycloalkyl, 3-14 membered heterocyclyl or —$C_{1-5}$alkyl-N($R^9,R^{10}$), all of which groups can be optionally and independently substituted with one or more =O, —CN, =S, halogen, or $R^{11}$, wherein $R^9$, $R^{10}$ and $R^{11}$ are as defined above.

In another aspect the invention relates to compounds of formula (I), wherein $R^7$, $R^8$ are the same or different, independently selected from —$C_{6-10}$aryl, 5-12 membered heteroaryl, all of which groups can be optionally and independently substituted with one or more —CN, halogen, or $R^{11}$, wherein $R^{11}$ are as defined above.

In another aspect the invention relates to compounds of formula (I), wherein $R^8$ is selected from —O—$C_{1-5}$alkyl, —S—$C_{1-5}$alkyl, —$C_{1-5}$alkyl, —$C_{2-5}$alkenyl, —$C_{2-5}$alkynyl, —$C_{3-10}$cycloalkyl, 3-14 membered heterocyclyl, —$C_{1-5}$alkyl-O—$R^9$, —$C_{1-5}$alkyl-S—$R^9$, or —$C_{1-5}$alkyl-N($R^9,R^{10}$), all of which groups can be optionally and independently substituted with one or more =O, —CN, =S, halogen, or $R^{11}$, wherein $R^9$, $R^{10}$ and $R^{11}$ are as defined above.

In a preferred embodiment the invention relates to compounds of formula (I), wherein $R^8$ is selected from —O—$C_{1-5}$alkyl, —S—$C_{1-5}$alkyl, —$C_{1-5}$alkyl, —$C_{3-10}$cycloalkyl, 3-14 membered heterocyclyl, or —$C_{1-5}$alkyl-N($R^9,R^{10}$), all of which groups can be optionally and independently substituted with one or more =O, —CN, =S, halogen, or $R^{11}$, wherein $R^9$, $R^{10}$ and $R^{11}$ is as defined above.

In another aspect the invention relates to compounds of formula (I), wherein $R^2$ is —$N(R^7,R^8)$ wherein $R^7$ and $R^8$ are as defined above and wherein $R^7$ and $R^8$ taken together with the nitrogen atom to which they are attached form a partially or fully saturated 3-14 membered heterocyclyl optionally substituted with one or more =O, —CN, =S, halogen, or $R^{11}$, wherein $R^{11}$ is as defined above.

In a preferred embodiment $R^2$ is morpholinyl, optionally and independently substituted with one or more =O, —CN, =S, halogen, or $R^{11}$, wherein $R^{11}$ is as defined above. In a preferred embodiment, $R^{11}$ is —$C_{1-3}$alkyl, preferably —$CH_3$.

In another preferred embodiment $R^2$ is piperazinyl, optionally and independently substituted with one or more =O, or $R^{11}$. In a preferred embodiment, $R^{11}$ is selected from —$CH_3$, -cyclopropyl, —$C(O)CH_3$, —$S(O)_2CH_3$.

In a further preferred embodiment $R^2$ is [1,4]diazepanyl, optionally and independently substituted with one or more =O, —CN, =S, halogen or $R^{11}$, in a preferred embodiment substituted with —$C(O)CH_3$.

In a further preferred embodiment $R^2$ is piperidine, optionally and independently substituted with one or more =O, —CN, =S, halogen or $R^{11}$, in a preferred embodiment independently substituted with one or more =O, —$CH_3$, —OH, —$S(O)_2CH_3$, —O—$CH_3$.

In another aspect the invention relates to compounds of formula (I), wherein $R^7$ is —$C_{1-3}$alkyl or tetrahydropyranyl.

In another aspect the invention relates to compounds of formula (I), wherein $R^9$ is selected from —H, —$C_{1-5}$alkyl, —$C_{2-5}$alkenyl, —$C_{2-5}$alkynyl, —$C_{3-10}$cycloalkyl, 3-14 membered heterocyclyl, —$C_{1-5}$alkyl-O—$C_{1-5}$alkyl, —$C_{1-5}$alkyl-S—$C_{1-5}$alkyl, or —$C_{1-5}$alkyl-N($C_{1-5}$alkyl, $C_{1-5}$alkyl), all of which groups can be optionally and independently substituted with one or more =O, —CN, =S, halogen, or $R^{11}$, wherein $R^{11}$ is as defined above.

In another aspect the invention relates to compounds of formula (I), wherein $R^9$ is selected from —H, —$C_{1-5}$-alkyl, —$C_{3-10}$cycloalkyl, 3-14 membered heterocyclyl, —$C_{1-5}$alkyl-O—$C_{1-5}$alkyl, or —$C_{1-5}$alkyl-N($C_{1-3}$alkyl, $C_{1-3}$alkyl), all of which groups can be optionally and independently substituted with one or more =O, —CN, =S, halogen, or $R^{11}$, wherein $R^{11}$ is as defined above.

In another aspect the invention relates to compounds of formula (I), wherein $R^9$, $R^{10}$ are the same or different, independently selected from —$C_{6-10}$aryl, 5-12 membered heteroaryl, all of which groups can be optionally and independently substituted with one or more —CN, halogen, or $R^{11}$, wherein $R^{11}$ is as defined above.

In another aspect the invention relates to compounds of formula (I), wherein $R^{10}$ is selected from —H, —O—$C_{1-5}$alkyl, —$C_{1-5}$alkyl, —$C_{2-5}$alkenyl, —$C_{2-5}$alkynyl, —$C_{3-10}$cycloalkyl, 3-14 membered heterocyclyl, —$C_{1-5}$alkyl-O—$C_{1-5}$alkyl, —$C_{1-5}$alkyl-S—$C_{1-5}$alkyl or —$C_{1-5}$alkyl-N($C_{1-5}$alkyl, $C_{1-5}$alkyl), all of which groups can be optionally and independently substituted with one or more =O, —CN, =S, halogen, or $R^{11}$, wherein $R^{11}$ is as defined above.

In another aspect the invention relates to compounds of formula (I), wherein $R^{10}$ is selected from —H, —O—$C_{1-5}$alkyl, —$C_{1-5}$alkyl, —$C_{3-10}$cycloalkyl, 3-14 membered heterocyclyl, —$C_{1-5}$alkyl-O—$C_{1-5}$alkyl, or —$C_{1-5}$alkyl-N($C_{1-3}$alkyl, $C_{1-3}$alkyl), all of which groups can be optionally and independently substituted with one or more =O, —CN, =S, halogen, or $R^{11}$, wherein $R^{11}$ is as defined above.

In another aspect the invention relates to compounds of formula (I), wherein $R^{11}$ is selected from —OH, —$NH_2$, —$CF_3$, —$S(O)_2CH_3$, —$C(O)CH_3$, —$OCF_3$, —$OCHF_2$, —CN or -nitro, —NH—$C_{1-5}$alkyl, —N($C_{1-5}$alkyl, $C_{1-5}$alkyl), —O—$C_{1-5}$alkyl, —S—$C_{1-5}$alkyl, —$C_{1-5}$alkyl, —$C_{2-5}$alkenyl, —$C_{2-5}$alkynyl, —$C_{3-10}$cycloalkyl, 3-14 membered heterocyclyl, all of which groups can be optionally and independently substituted with one or more =O, —CN, =S, halogen, —OH, —$NH_2$, —$CH_3$, —$CH_2CH_3$, —$CF_3$, —$S(O)_2CH_3$, —$C(O)CH_3$, -propyl, -isopropyl, -cyclopropyl, -butyl, iso-butyl-, tert-butyl-, -cyclobutyl, -cyclopentyl, -cyclohexyl, —NH—$CH_3$, —$N(CH_3)_2$, —$N(CH_2CH_3)_2$, —NH—CH$_2$CH$_3$, —N(CH$_3$,CH$_2$CH$_3$), —O—CH$_3$, —O—CH$_2$CH$_3$, —S—CH$_3$, —C(O)NHCH$_3$, —C(O)N(CH$_3$)$_2$, —C(O)NH—CH$_2$CH$_3$, —C(O)N(CH$_2$CH$_3$)$_2$, —C(O)-pyrazolidinyl, —OCF$_3$, —OCHF$_2$, -tetrahydrofuryl, -tetrahydropyranyl, —N-methylpiperazinly, -pyrrolidinyl, -morpholinyl or -nitro.

In another aspect the invention relates to compounds of formula (I), wherein R$^{11}$ is selected from —C$_{6-10}$aryl or 5-12 membered heteroaryl, all of which groups can be optionally and independently substituted with one or more —CN, halogen, —OH, —NH$_2$, —CH$_3$, —CH$_2$CH$_3$, —CF$_3$, —S(O)$_2$CH$_3$, —C(O)CH$_3$, -propyl, -isopropyl, -cyclopropyl, -butyl, iso-butyl-, tert-butyl-, -cyclobutyl, -cyclopentyl, -cyclohexyl, —NH—CH$_3$, —N(CH$_3$)$_2$, —N(CH$_2$CH$_3$)$_2$, —NH—CH$_2$CH$_3$, —N(CH$_3$,CH$_2$CH$_3$), —O—CH$_3$, —O—CH$_2$CH$_3$, —S—CH$_3$, —C(O)NHCH$_3$, —C(O)N(CH$_3$)$_2$, —C(O)NH—CH$_2$CH$_3$, —C(O)N(CH$_2$CH$_3$)$_2$, —C(O)-pyrazolidinyl, —OCF$_3$, —OCHF$_2$, -tetrahydrofuryl, -tetrahydropyranyl, —N-methylpiperazinly, -pyrrolidinyl, -morpholinyl or -nitro.

In another aspect the invention relates to compounds of formula (I), wherein R$^{11}$ is selected from —OH, —NH$_2$, —CH$_3$, —CH$_2$CH$_3$, —CF$_3$, —S(O)$_2$CH$_3$, —C(O)CH$_3$, -propyl, -isopropyl, -cyclopropyl, -butyl, iso-butyl-, tert-butyl-, -cyclobutyl, -cyclopentyl, -cyclohexyl, —NH—CH$_3$, —N(CH$_3$)$_2$, —N(CH$_2$CH$_3$)$_2$, —NH—CH$_2$CH$_3$, —N(CH$_3$,CH$_2$CH$_3$), —O—CH$_3$, —O—CH$_2$CH$_3$, —S—CH$_3$, —C(O)NHCH$_3$, —C(O)N(CH$_3$)$_2$, —C(O)N(CH$_2$CH$_3$)$_2$, —C(O)NH—CH$_2$CH$_3$, —C(O)-pyrazolidinyl, —OCF$_3$, —OCHF$_2$, -tetrahydrofuryl, tetrahydropyranyl, —N-methylpiperazinly, -pyrrolidinyl, -morpholinyl, halogen, —CN or -nitro.

In another aspect the invention relates to compounds of formula (I), wherein R$^{12}$ is selected from —H, —C$_{1-5}$alkyl, —C$_{2-5}$alkenyl, —C$_{2-5}$alkynyl, —C$_{3-10}$cycloalkyl, 3-14 membered heterocyclyl, —C$_{1-5}$alkyl-O—C$_{1-5}$alkyl, —C$_{1-5}$alkyl-S—C$_{1-5}$alkyl, or —C$_{1-5}$alkyl-N(—C$_{1-5}$alkyl, —C$_{1-5}$alkyl), all of which groups can be optionally and independently substituted with one or more =O, —CN, =S, halogen, or R$^{14}$, wherein R$^{14}$ is as defined above.

In another aspect the invention relates to compounds of formula (I), wherein R$^{12}$ is selected from —H, —C$_{1-5}$-alkyl, —C$_{3-10}$cycloalkyl, 3-14 membered heterocyclyl, —C$_{1-5}$alkyl-O—C$_{1-5}$alkyl, or —C$_{1-5}$alkyl-N(—C$_{1-3}$alkyl, —C$_{1-3}$alkyl), all of which groups can be optionally and independently substituted with one or more =O, —CN, =S, halogen, or R$^{14}$ wherein R$^{14}$ is as defined above.

In another aspect the invention relates to compounds of formula (I), wherein R$^{12}$, R$^{13}$ are the same or different, independently selected from —C$_{6-10}$aryl, 5-12 membered heteroaryl, all of which groups can be optionally and independently substituted with one or more —CN, halogen, or R$^{14}$, wherein R$^{14}$ is as defined above.

In another aspect the invention relates to compounds of formula (I), wherein R$^{13}$ is selected from —H, —O—C$_{1-5}$alkyl, —C$_{1-5}$alkyl, —C$_{2-5}$alkenyl, —C$_{2-5}$alkynyl, —C$_{3-10}$cycloalkyl, 3-14 membered heterocyclyl, —C$_{1-5}$alkyl-O—C$_{1-5}$alkyl, —C$_{1-5}$alkyl-S—C$_{1-5}$alkyl, or —C$_{1-5}$alkyl-N(—C$_{1-5}$alkyl, —C$_{1-5}$alkyl), all of which groups can be optionally and independently substituted with one or more =O, —CN, =S, halogen, or R$^{14}$, wherein R$^{14}$ is as defined above.

In another aspect the invention relates to compounds of formula (I), wherein R$^{13}$ is selected from —H, —O—C$_{1-5}$alkyl, —C$_{1-5}$alkyl, —C$_{3-10}$cycloalkyl, 3-14 membered heterocyclyl, —C$_{1-5}$alkyl-O—C$_{1-5}$alkyl, or —C$_{1-5}$alkyl-N(—C$_{1-3}$alkyl, —C$_{1-3}$alkyl), all of which groups can be optionally and independently substituted with one or more =O, —CN, =S, halogen, or R$^{14}$, wherein R$^{14}$ is as defined above.

In another aspect the invention relates to compounds of formula (I), wherein R$^{12}$ and R$^{13}$ taken together with the atom to which they are attached form a 3-14 membered heterocyclyl which can be optionally and independently substituted with one or more =O, —CN, =S, halogen, or R$^{14}$, wherein R$^{14}$ is as defined above.

In another aspect the invention relates to compounds of formula (I), wherein R$^{14}$ is selected from —OH, —NH$_2$, —CF$_3$, —S(O)$_2$CH$_3$, —C(O)CH$_3$, —OCF$_3$, —OCHF$_2$ or -nitro, —NH—C$_{1-5}$alkyl, —N(C$_{1-5}$alkyl, C$_{1-5}$alkyl), —O—C$_{1-5}$alkyl, —S—C$_{1-5}$alkyl, —C$_{1-5}$alkyl, —C$_{2-5}$alkenyl, —C$_{2-5}$alkynyl, —C$_{3-10}$cycloalkyl, 3-14 membered heterocyclyl, all of which groups can be optionally and independently substituted with one or more =O, —CN, =S, halogen, —H, —OH, —NH$_2$, —CH$_3$, —CH$_2$CH$_3$, —CF$_3$, —S(O)$_2$CH$_3$, —C(O)CH$_3$, -propyl, -isopropyl, -cyclopropyl, -butyl, iso-butyl-, tert-butyl-, -cyclobutyl, -cyclopentyl, -cyclohexyl, —NH—CH$_3$, —N(CH$_3$)$_2$, —N(CH$_2$CH$_3$)$_2$, —NH—CH$_2$CH$_3$, —N(CH$_3$,CH$_2$CH$_3$), —O—CH$_3$, —O—CH$_2$CH$_3$, —S—CH$_3$, —C(O)NHCH$_3$, —C(O)N(CH$_3$)$_2$, —C(O)NH—CH$_2$CH$_3$, —C(O)N(CH$_2$CH$_3$)$_2$, —C(O)-pyrazolidinyl, —OCF$_3$, —OCHF$_2$, -tetrahydrofuryl, -tetrahydropyranyl, —N-methylpiperazinly, -pyrrolidinyl, -morpholinyl or -nitro.

In another aspect the invention relates to compounds of formula (I), wherein R$^{14}$ is selected from —C$_{6-10}$aryl, 5-12 membered heteroaryl all of which groups can be optionally and independently substituted with one or more —CN, halogen, —OH, —NH$_2$, —CH$_3$, —CH$_2$CH$_3$, —CF$_3$, —S(O)$_2$CH$_3$, —C(O)CH$_3$, -propyl, -isopropyl, -cyclopropyl, -butyl, iso-butyl-, tert-butyl-, -cyclobutyl, -cyclopentyl, -cyclohexyl, —NH—CH$_3$, —N(CH$_3$)$_2$, —N(CH$_2$CH$_3$)$_2$, —NH—CH$_2$CH$_3$, —N(CH$_3$,CH$_2$CH$_3$), —O—CH$_3$, —O—CH$_2$CH$_3$, —S—CH$_3$, —C(O)NHCH$_3$, —C(O)N(CH$_3$)$_2$, —C(O)NH—CH$_2$CH$_3$, —C(O)N(CH$_2$CH$_3$)$_2$, —C(O)-pyrazolidinyl, —OCF$_3$, —OCHF$_2$, -tetrahydrofuryl, -tetrahydropyranyl, —N-methylpiperazinly, -pyrrolidinyl, -morpholinyl or -nitro.

In another aspect the invention relates to compounds of formula (I), wherein R$^{14}$ is —OH, —NH$_2$, —CH$_3$, —CH$_2$CH$_3$, —CF$_3$, —S(O)$_2$CH$_3$, —C(O)CH$_3$, -propyl, -isopropyl -cyclopropyl, -butyl, iso-butyl-, tert-butyl-, -cyclobutyl-, -cyclopentyl, -cyclohexyl, —NH—CH$_3$, —N(CH$_3$)$_2$, —N(CH$_2$CH$_3$)$_2$, —NH—CH$_2$CH$_3$, —N(CH$_3$,CH$_2$CH$_3$), —O—CH$_3$, —O—CH$_2$CH$_3$, —S—CH$_3$, —C(O)NHCH$_3$, —C(O)N(CH$_3$)$_2$, —C(O)N(CH$_2$CH$_3$)$_2$, —C(O)NH—CH$_2$CH$_3$, —C(O)-pyrazolidinyl, —OCF$_3$, —OCHF$_2$, -tetrahydrofuryl, -tetrahydropyranyl, —N-methylpiperazinly, -pyrrolidinyl, -morpholinyl, halogen, —CN or -nitro.

In another aspect the invention relates to compounds of formula (I), wherein R$^{15}$ and R$^{16}$ are the same or different, independently selected from —OH, —NH$_2$, —CF$_3$, —S(O)$_2$CH$_3$, —C(O)CH$_3$, —OCF$_3$, —OCHF$_2$, —CN or -nitro, —NH—C$_{1-5}$alkyl, —N(C$_{1-5}$alkyl, C$_{1-5}$alkyl), —O—C$_{1-5}$alkyl, —S—C$_{1-5}$alkyl, —C$_{1-5}$alkyl, —C$_{2-5}$alkenyl, —C$_{2-5}$alkynyl, —C$_{3-10}$cycloalkyl, 3-14 membered heterocyclyl, all of which can be optionally and independently substituted with one or more =O, —CN, =S, halogen, —OH, —NH$_2$, —CH$_3$, —CH$_2$CH$_3$, —CF$_3$, —S(O)$_2$CH$_3$, —C(O)CH$_3$, -propyl, -isopropyl, -cyclopropyl, -butyl, iso-butyl-, tert-butyl-, -cyclobutyl, -cyclopentyl, -cyclohexyl, —NH—CH$_3$, —N(CH$_3$)$_2$, —N(CH$_2$CH$_3$)$_2$, —NH—CH$_2$CH$_3$, —N(CH$_3$,CH$_2$CH$_3$), —O—CH$_3$, —O—CH$_2$CH$_3$, —S—CH$_3$, —C(O)NHCH$_3$, —C(O)N(CH$_3$)$_2$, —C(O)NH—CH$_2$CH$_3$, —C(O)N(CH$_2$CH$_3$)$_2$, —C(O)-pyrazolidinyl, —OCF$_3$, —OCHF$_2$, -tetrahydrofuryl, -tetrahydropyranyl, —N-methylpiperazinly, -pyrrolidinyl, -morpholinyl or -nitro.

In another aspect the invention relates to compounds of formula (I), wherein R$^{15}$ and R$^{16}$ are the same or different, independently selected from —C$_{6-10}$aryl or 5-12 membered heteroaryl, all of which groups can be optionally and independently substituted with one or more —CN, halogen, —OH, —NH$_2$, —CH$_3$, —CH$_2$CH$_3$, —CF$_3$, —S(O)$_2$CH$_3$, —C(O)CH$_3$, -propyl, -isopropyl, -cyclopropyl, -butyl, iso-butyl-, tert-butyl-, -cyclobutyl, -cyclopentyl, -cyclohexyl, —NH—CH$_3$, —N(CH$_3$)$_2$, —N(CH$_2$CH$_3$)$_2$, —NH—CH$_2$CH$_3$, —N(CH$_3$,CH$_2$CH$_3$), —O—CH$_3$, —O—CH$_2$CH$_3$, —S—CH$_3$, —C(O)NHCH$_3$, —C(O)N(CH$_3$)$_2$, —C(O)NH—CH$_2$CH$_3$, —C(O)N(CH$_2$CH$_3$)$_2$, —C(O)-pyrazolidinyl, —OCF$_3$, —OCHF$_2$, -tetrahydrofuryl, -tetrahydropyranyl, —N-methylpiperazinly, -pyrrolidinyl, -morpholinyl or -nitro.

In another aspect the invention relates to compounds of formula (I), wherein R$^{15}$ and R$^{16}$ are the same or different, independently selected from —OH, —NH$_2$, —CH$_3$, —CH$_2$CH$_3$, —CF$_3$, —F, —Cl, —Br, —CN, -nitro, —NH—CH$_3$, —N(CH$_3$)$_2$, —NH(CH$_2$CH$_3$), —N(CH$_2$CH$_3$)$_2$, —N(CH$_3$,CH$_2$CH$_3$), —O—CH$_3$, —O—CH$_2$CH$_3$, —S—CH$_3$, —C(O)-pyrazolidinyl, —OCF$_3$, —OCHF$_2$.

In another aspect the invention relates to compounds of formula (I), wherein R$^{15}$ and R$^{16}$ taken together with the atom to which they are attached form a 3-14 membered heterocyclyl which can be optionally and independently substituted with one or more =O, CN, =S, halogen, —OH, —NH$_2$, —CH$_3$, —CH$_2$CH$_3$, —CF$_3$, —S(O)$_2$CH$_3$, —C(O)CH$_3$, -propyl, -isopropyl, -cyclopropyl, -butyl, iso-butyl-, tert-butyl-, -cyclobutyl, -cyclopentyl, -cyclohexyl, —NH—CH$_3$, —N(CH$_3$)$_2$, —N(CH$_2$CH$_3$)$_2$, —NH—CH$_2$CH$_3$, —N(CH$_3$,CH$_2$CH$_3$), —O—CH$_3$, —O—CH$_2$CH$_3$, —S—CH$_3$, —C(O)NHCH$_3$, —C(O)N(CH$_3$)$_2$, —C(O)N(CH$_2$CH$_3$)$_2$, —C(O)NH—CH$_2$CH$_3$, —C(O)-pyrazolidinyl, —OCF$_3$, —OCHF$_2$, -tetrahydrofuryl, -tetrahydropyranyl, —N-methylpiperazinly, -pyrrolidinyl, -morpholinyl or -nitro.

In another aspect, the invention relates to compounds of formula (I), wherein R$^1$ is —NH$_2$ and R$^5$ is —C$_{1-5}$alkyl.

The present invention further relates to hydrates, solvates, polymorphs, metabolites, derivatives and prodrugs of compounds of general formula (I) or of anyone of the embodiments as disclosed above.

In another aspect the invention relates to compounds of general formula (I) or of anyone of the embodiments as disclosed above for use in the treatment of cancer.

In another aspect the invention relates to compounds of general formula (I) or of anyone of the embodiments as disclosed above—or the pharmaceutically acceptable salts thereof—as medicaments.

In another aspect the invention relates to compounds of general formula (I) or of anyone of the embodiments as disclosed above—or the pharmaceutically acceptable salts thereof—for use in the treatment and/or prevention of cancer, infections, inflammations and autoimmune diseases.

In another aspect the invention relates to compounds of general formula (I) or of anyone of the embodiments as disclosed above—or the pharmaceutically acceptable salts thereof—for use in the treatment and/or prevention of cancer. Preferably, carcinomas of the breast, prostate, brain or ovary, non-small-cell bronchial carcinomas (NSCLC), melanomas and chronic lymphatic leukaemias (CLL) or cancer types which pathway is activated by either mutation of PI3K or loss of PTEN.

In another aspect the invention relates to compounds of general formula (I) or of anyone of the embodiments as disclosed above—or the pharmaceutically acceptable salts thereof—for use in the treatment and/or prevention of carcinomas of the breast, prostate, brain or ovary, non-small-cell bronchial carcinomas (NSCLC), melanomas and chronic lymphatic leukaemias (CLL) or cancer types which pathway is activated by either mutation of PI3K or loss of PTEN.

In another aspect the invention relates to a method for the treatment and/or prevention of cancer comprising administering a therapeutically effective amount of a compound of general formula (I) or of anyone of the embodiments as disclosed above—or one of the pharmaceutically acceptable salts thereof—to a human being.

In another aspect the invention relates to a pharmaceutical preparation containing as active substance one or more compounds of general formula (I) or of anyone of the embodiments as disclosed above—or the pharmaceutically acceptable salts thereof—optionally in combination with conventional excipients and/or carriers.

In another aspect the invention relates to a pharmaceutical preparation comprising a compound of general formula (I) or of anyone of the embodiments as disclosed above—or one of the pharmaceutically acceptable salts thereof—and at least one other cytostatic or cytotoxic active substance, different from formula (I).

DEFINITIONS

Terms that are not specifically defined here have the meanings that are apparent to the skilled man in the light of the overall disclosure and the context as a whole.

As used herein, the following definitions apply, unless stated otherwise:

In the groups, radicals, or moieties defined below, the number of carbon atoms is often specified preceding the group, for example, —C$_{1-5}$alkyl means an alkyl group or radical having 1 to 5 carbon atoms. In general, for groups comprising two or more subgroups, the first named sub-group is the radical attachment point, for example the substituent —C$_{1-5}$alkyl-C$_{3-10}$cylcoalkyl, means a C$_{3-10}$cylcoalkyl group which is bound to a C$_{1-5}$alkyl, the latter of which is bound to the core structure or to the group to which the substituent is attached.

The indication of the number of members in groups that contain one or more heteroatom(s) (heteroalkyl, heteroaryl, heteroarylalkyl, heterocyclyl, heterocycylalkyl) relates to the total atomic number of all the ring members or chain members or the total of all the ring and chain members. The person skilled in the art will appreciate that substituent groups containing a nitrogen atom can also be indicated as amine or amino. Similarly, groups containing oxygen atom can also be indicated with -oxy, like for example alkoxy. Groups containing —C(O)— can also be indicated as carboxy; groups containing —NC(O)— can also be indicated as amide; groups containing —NC(O)N— can also be indicated as urea; groups containing —NS(O)$_2$— can also be indicated as sulfonamide.

Alkyl denotes monovalent, saturated hydrocarbon chains, which may be present in both linear and branched form. If an alkyl is substituted, the substitution may take place independently of one another, by mono- or polysubstitution in each case, on all the hydrogen-carrying carbon atoms.

The term "C$_{1-5}$-alkyl" includes for example methyl (Me; —CH$_3$), ethyl (Et; —CH$_2$CH$_3$), 1-propyl (n-propyl; n-Pr; —CH$_2$CH$_2$CH$_3$), 2-propyl (i-Pr; iso-propyl; —CH(CH$_3$)$_2$), 1-butyl (n-butyl; n-Bu; —CH$_2$CH$_2$CH$_2$CH$_3$), 2-methyl-1-propyl (iso-butyl; i-Bu; —CH$_2$CH(CH$_3$)$_2$), 2-butyl (sec-butyl; sec-Bu; —CH(CH$_3$)CH$_2$CH$_3$), 2-methyl-2-propyl (tert-butyl; t-Bu; —C(CH$_3$)$_3$), 1-pentyl (n-pentyl; —CH$_2$CH$_2$CH$_2$CH$_2$CH$_3$), 2-pentyl (—CH(CH$_3$) CH$_2$CH$_2$CH$_3$), 3-pentyl (—CH(CH$_2$CH$_3$)$_2$), 3-methyl-1-butyl (iso-pentyl; —CH$_2$CH$_2$CH(CH$_3$)$_2$), 2-methyl-2-butyl (—C(CH$_3$)$_2$CH$_2$CH$_3$), 3-methyl-2-butyl (—CH(CH$_3$)CH (CH$_3$)$_2$), 2,2-dimethyl-1-propyl (neo-pentyl; —CH$_2$C (CH$_3$)$_3$), 2-methyl-1-butyl (—CH$_2$CH(CH$_3$)CH$_2$CH$_3$).

By the terms propyl, butyl, pentyl, etc. without any further definition are meant saturated hydrocarbon groups with the corresponding number of carbon atoms, wherein all isomeric forms are included.

The above definition for alkyl also applies if alkyl is a part of another group such as for example $C_{x-y}$-alkylamino or $C_{x-y}$-alkyloxy or $C_{x-y}$-alkoxy, wherein $C_{x-y}$-alkyloxy and $C_{x-y}$-alkoxy indicate the same group.

The term alkylene can also be derived from alkyl. Alkylene is bivalent, unlike alkyl, and requires two binding partners. Formally, the second valency is produced by removing a hydrogen atom in an alkyl. Corresponding groups are for example —CH$_3$ and —CH$_2$—, —CH$_2$CH$_3$ and —CH$_2$CH$_2$— or >CHCH$_3$ etc.

The term "$C_{1-4}$-alkylene" includes for example —(CH$_2$)—, —(CH$_2$—CH$_2$)—, —(CH(CH$_3$))—, —(CH$_2$—CH$_2$—CH$_2$)—, —(C(CH$_3$)$_2$)—, —(CH(CH$_2$CH$_3$))—, —(CH(CH$_3$)—CH$_2$)—, —(CH$_2$—CH(CH$_3$))—, —(CH$_2$—CH$_2$—CH$_2$—CH$_2$)—, —(CH$_2$—CH$_2$—CH(CH$_3$))—, —(CH(CH$_3$)—CH$_2$—CH$_2$)—, —(CH$_2$—CH(CH$_3$)—CH$_2$)—, —(CH$_2$—C(CH$_3$)$_2$)—, —(C(CH$_3$)$_2$—CH$_2$)—, —(CH(CH$_3$)—CH(CH$_3$))—, —(CH$_2$—CH(CH$_2$CH$_3$))—, —(CH(CH$_2$CH$_3$)—CH$_2$)—, —(CH(CH$_2$CH$_2$CH$_3$))—, —(CHCH(CH$_3$)$_2$)— and —C(CH$_3$)(CH$_2$CH$_3$)—.

Other examples of alkylene are methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene, etc.

By the generic terms propylene, butylene, pentylene, hexylene etc. without any further definition are meant all the conceivable isomeric forms with the corresponding number of carbon atoms, i.e. propylene includes 1-methylethylene and butylene includes 1-methylpropylene, 2-methylpropylene, 1,1-dimethylethylene and 1,2-dimethylethylene.

The above definition for alkylene also applies if alkylene is part of another group such as for example in HO—$C_{x-y}$-alkylenamino or H$_2$N—$C_{x-y}$-alkylenoxy.

Unlike alkyl, alkenyl consists of at least two carbon atoms, wherein at least two adjacent carbon atoms are joined together by a C—C double bond. If in an alkyl as hereinbefore defined having at least two carbon atoms, two hydrogen atoms on adjacent carbon atoms are formally removed and the free valencies are saturated to form a second bond, the corresponding alkenyl is formed.

Examples of alkenyl are vinyl (ethenyl), prop-1-enyl, allyl (prop-2-enyl), isopropenyl, but-1-enyl, but-2-enyl, but-3-enyl, 2-methyl-prop-2-enyl, 2-methyl-prop-1-enyl, 1-methyl-prop-2-enyl, 1-methyl-prop-1-enyl, 1-methylidenepropyl, pent-1-enyl, pent-2-enyl, pent-3-enyl, pent-4-enyl, 3-methyl-but-3-enyl, 3-methyl-but-2-enyl, 3-methyl-but-1-enyl, hex-1-enyl, hex-2-enyl, hex-3-enyl, hex-4-enyl, hex-5-enyl, 2,3-dimethyl-but-3-enyl, 2,3-dimethyl-but-2-enyl, 2-methylidene-3-methylbutyl, 2,3-dimethyl-but-1-enyl, hexa-1,3-dienyl, hexa-1,4-dienyl, penta-1,4-dienyl, penta-1,3-dienyl, buta-1,3-dienyl, 2,3-dimethylbuta-1,3-diene etc.

By the generic terms propenyl, butenyl, pentenyl, hexenyl, butadienyl, pentadienyl, hexa-dienyl, heptadienyl, octadienyl, nonadienyl, decadienyl etc. without any further definition are meant all the conceivable isomeric forms with the corresponding number of carbon atoms, i.e. propenyl includes prop-1-enyl and prop-2-enyl, butenyl includes but-1-enyl, but-2-enyl, but-3-enyl, 1-methyl-prop-1-enyl, 1-methyl-prop-2-enyl etc.

Alkenyl may optionally be present in the cis or trans or E or Z orientation with regard to the double bond(s).

The above definition for alkenyl also applies when alkenyl is part of another group such as for example in $C_{x-y}$-alkenylamino or $C_{x-y}$-alkenyloxy.

Unlike alkylene, alkenylene consists of at least two carbon atoms, wherein at least two adjacent carbon atoms are joined together by a C—C double bond. If in an alkylene as hereinbefore defined having at least two carbon atoms, two hydrogen atoms at adjacent carbon atoms are formally removed and the free valencies are saturated to form a second bond, the corresponding alkenylene is formed.

Examples of alkenylene are ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene, hexenylene etc.

By the generic terms propenylene, butenylene, pentenylene, hexenylene etc. without any further definition are meant all the conceivable isomeric forms with the corresponding number of carbon atoms, i.e. propenylene includes 1-methylethenylene and butenylene includes 1-methylpropenylene, 2-methylpropenylene, 1,1-dimethylethenylene and 1,2-dimethylethenylene.

Alkenylene may optionally be present in the cis or trans or E or Z orientation with regard to the double bond(s).

The above definition for alkenylene also applies when alkenylene is a part of another group as in for example HO—$C_{x-y}$-alkenylenamino or H$_2$N—$C_{x-y}$-alkenylenoxy.

Unlike alkyl, alkynyl consists of at least two carbon atoms, wherein at least two adjacent carbon atoms are joined together by a C—C triple bond. If in an alkyl as hereinbefore defined having at least two carbon atoms, two hydrogen atoms in each case at adjacent carbon atoms are formally removed and the free valencies are saturated to form two further bonds, the corresponding alkynyl is formed.

Examples of alkynyl are ethynyl, prop-1-ynyl, prop-2-ynyl, but-1-ynyl, but-2-ynyl, but-3-ynyl, 1-methyl-prop-2-ynyl, pent-1-ynyl, pent-2-ynyl, pent-3-ynyl, pent-4-ynyl, 3-methyl-but-1-ynyl.

By the generic terms propynyl, butynyl, pentynyl, etc. without any further definition are meant all the conceivable isomeric forms with the corresponding number of carbon atoms, i.e. propynyl includes prop-1-ynyl and prop-2-ynyl, butynyl includes but-1-ynyl, but-2-ynyl, but-3-ynyl, 1-methyl-prop-1-ynyl, 1-methyl-prop-2-ynyl.

If a hydrocarbon chain carries both at least one double bond and also at least one triple bond, by definition it belongs to the alkynyl subgroup.

The above definition for alkynyl also applies if alkynyl is part of another group, as in $C_{x-y}$-alkynylamino or $C_{x-y}$-alkynyloxy, for example.

Unlike alkylene, alkynylene consists of at least two carbon atoms, wherein at least two adjacent carbon atoms are joined together by a C—C triple bond. If in an alkylene as hereinbefore defined having at least two carbon atoms, two hydrogen atoms in each case at adjacent carbon atoms are formally removed and the free valencies are saturated to form two further bonds, the corresponding alkynylene is formed.

Examples of alkynylene are ethynylene, propynylene, 1-methylethynylene, butynylene, 1-methylpropynylene, 1,1- dimethylethynylene, 1,2-dimethylethynylene, pentynylene, 1,1-dimethylpropynylene, 2,2-dimethylpropynylene, 1,2-dimethylpropynylene, 1,3-dimethylpropynylene, hexynylene etc.

By the generic terms propynylene, butynylene, pentynylene, ect. without any further definition are meant all the conceivable isomeric forms with the corresponding number of carbon atoms, i.e. propynylene includes 1-methylethynylene and butynylene includes 1-methylpropynylene, 2-methylpropynylene, 1,1-dimethylethynylene and 1,2-dimethylethynylene.

The above definition for alkynylene also applies if alkynylene is part of another group, as in HO—$C_{x-y}$-alkynyleneamino or $H_2N$—$C_{x-y}$-alkynyleneoxy, for example.

By heteroatoms are meant oxygen, nitrogen and sulphur atoms.

Haloalkyl (haloalkenyl, haloalkynyl) is derived from the previously defined alkyl (alkenyl, alkynyl) by replacing one or more hydrogen atoms of the hydrocarbon chain independently of one another by halogen atoms, which may be identical or different. If a haloalkyl (haloalkenyl, haloalkynyl) is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —$CF=CF_2$, —$CCl=CH_2$, —$CBr=CH_2$, —$CI=CH_2$, —$C\equiv C$—$CF_3$, —$CHFCH_2CH_3$, —$CHFCH_2CF_3$ etc.

From the previously defined haloalkyl (haloalkenyl, haloalkynyl) are also derived the terms haloalkylene (haloalkenylene, haloalkynylene). Haloalkylene (haloalkenyl, haloalkynyl), unlike haloalkyl, is bivalent and requires two binding partners. Formally, the second valency is formed by removing a hydrogen atom from a haloalkyl.

Corresponding groups are for example —$CH_2F$ and —CHF—, —$CHFCH_2$ and —CHFCHF— or >$CFCH_2F$ etc.

The above definitions also apply if the corresponding halogen groups are part of another group.

Halogen relates to fluorine, chlorine, bromine and/or iodine atoms.

Cycloalkyl is made up of the subgroups monocyclic hydrocarbon rings, bicyclic hydrocarbon rings and spiro-hydrocarbon rings. The systems are saturated. In bicyclic hydrocarbon rings two rings are joined together so that they have at least two carbon atoms together. In spiro-hydrocarbon rings a carbon atom (spiroatom) belongs to two rings together. If a cycloalkyl is to be substituted, the substitutions may take place independently of one another, in the form of mono- or polysubstitutions in each case, on all the hydrogen-carrying carbon atoms. Cycloalkyl itself may be linked as a substituent to the molecule via every suitable position of the ring system.

Examples of cycloalkyl are cyclopropyl, cyclobutyl, cyclopentyl, cyclohexyl, cycloheptyl, bicyclo[2.2.0]hexyl, bicyclo[3.2.0]heptyl, bicyclo[3.2.1]octyl, bicyclo[2.2.2]octyl, bicyclo[4.3.0]nonyl (octahydroindenyl), bicyclo[4.4.0]decyl (decahydronaphthalene), bicyclo[2.2.1]heptyl (norbornyl), bicyclo[4.1.0]heptyl (norcaranyl), bicyclo-[3.1.1]heptyl (pinanyl), spiro[2.5]octyl, spiro[3.3]heptyl etc.

The above definition for cycloalkyl also applies if cycloalkyl is part of another group as in $C_{x-y}$-cycloalkylamino or $C_{x-y}$-cycloalkyloxy, for example.

If the free valency of a cycloalkyl is saturated, then an alicyclic group is obtained.

The term cycloalkylene can thus be derived from the previously defined cycloalkyl. Cycloalkylene, unlike cycloalkyl, is bivalent and requires two binding partners. Formally, the second valency is obtained by removing a hydrogen atom from a cycloalkyl. Corresponding groups are for example cyclohexyl and

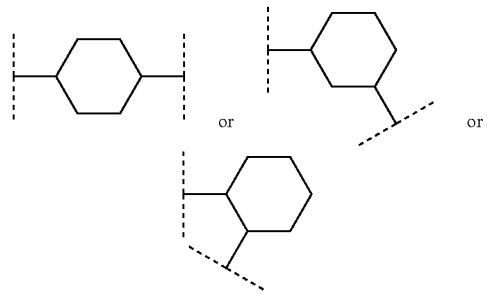

(cyclohexylene).

The above definition for cycloalkylene also applies if cycloalkylene is part of another group as in HO—$C_{x-y}$-cycloalkyleneamino or $H_2N$—$C_{x-y}$-cycloalkyleneoxy, for example.

Cycloalkenyl is also made up of the subgroups monocyclic hydrocarbon rings, bicyclic hydrocarbon rings and spiro-hydrocarbon rings. However, the systems are unsaturated, i.e. there is at least one C—C double bond but no aromatic system. If in a cycloalkyl as hereinbefore defined two hydrogen atoms at adjacent cyclic carbon atoms are formally removed and the free valencies are saturated to form a second bond, the corresponding cycloalkenyl is obtained. If a cycloalkenyl is to be substituted, the substitutions may take place independently of one another, in the form of mono- or polysubstitutions in each case, on all the hydrogen-carrying carbon atoms. Cycloalkenyl itself may be linked as a substituent to the molecule via every suitable position of the ring system.

Examples of cycloalkenyl are cycloprop-1-enyl, cycloprop-2-enyl, cyclobut-1-enyl, cyclobut-2-enyl, cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, cyclobuta-1,3-dienyl, cyclopenta-1,4-dienyl, cyclopenta-1,3-dienyl, cyclopenta-2,4-dienyl, cyclohexa-1,3-dienyl, cyclohexa-1,5-dienyl, cyclohexa-2,4-dienyl, cyclohexa-1,4-dienyl, cyclohexa-2,5-dienyl, bicyclo[2.2.1]hepta-2,5-dienyl (norborna-2,5-dienyl), bicyclo[2.2.1]hept-2-enyl (norbornenyl), spiro[4.5]dec-2-ene etc.

The above definition for cycloalkenyl also applies when cycloalkenyl is part of another group as in $C_{x-y}$-cycloalkenylamino or $C_x$-cycloalkenyloxy, for example.

If the free valency of a cycloalkenyl is saturated, then an unsaturated alicyclic group is obtained.

The term cycloalkenylene can thus be derived from the previously defined cycloalkenyl. Cycloalkenylene, unlike cycloalkenyl, is bivalent and requires two binding partners. Formally the second valency is obtained by removing a hydrogen atom from a cycloalkenyl. Corresponding groups are for example cyclopentenyl and

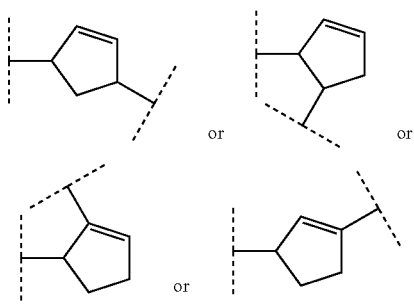

(cyclopentenylene) etc.

The above definition for cycloalkenylene also applies when cycloalkenylene is part of another group as in HO—$C_{x-y}$-cycloalkenyleneamino or $H_2N$—$C_{x-y}$-cycloalkenyleneoxy, for example.

Aryl denotes a mono-, bi- or tricyclic group with at least one aromatic carbocycle. Preferably it denotes a monocyclic group with six carbon atoms (phenyl) or a bicyclic group with nine or ten carbon atoms (two six-membered rings or one six-membered ring with a five-membered ring), wherein the second ring may also be aromatic or, however, may also be saturated or partially saturated. If an aryl is to be substituted, the substitutions may take place independently of one another, in the form of mono- or polysubstitutions in each case, on all the hydrogen-carrying carbon atoms. Aryl itself may be linked as a substituent to the molecule via every suitable position of the ring system.

Examples of aryl are phenyl, naphthyl, indanyl (2,3-dihydroindenyl), indenyl, anthracenyl, phenanthrenyl, tetrahydronaphthyl (1,2,3,4-tetrahydronaphthyl, tetralinyl), dihydronaphthyl (1,2-dihydronaphthyl), fluorenyl etc.

The above definition of aryl also applies when aryl is part of another group as in arylamino or aryloxy, for example.

If the free valency of an aryl is saturated, then an aromatic group is obtained.

The term arylene can also be derived from the previously defined aryl. Arylene, unlike aryl, is bivalent and requires two binding partners. Formally, the second valency is formed by removing a hydrogen atom from an aryl. Corresponding groups are e.g.

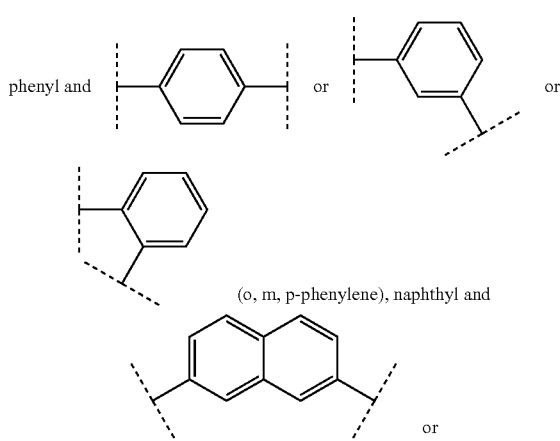

phenyl and (o, m, p-phenylene), naphthyl and

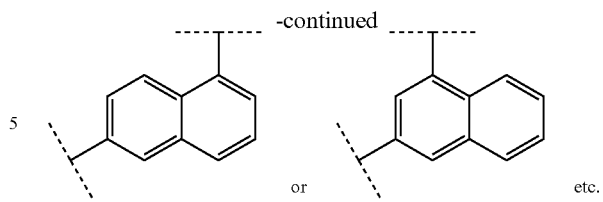

or etc.

The above definition for arylene also applies when arylene is part of another group as in HO-aryleneamino or $H_2N$-aryleneoxy for example.

Heterocyclyl denotes ring systems, which are derived from the previously defined cycloalkyl, cycloalkenyl and aryl by replacing one or more of the groups —$CH_2$-independently of one another in the hydrocarbon rings by the groups —O—, —S— or —NH— or by replacing one or more of the groups =CH— by the group =N—, wherein a total of not more than five heteroatoms may be present, at least one carbon atom may be present between two oxygen atoms and between two sulphur atoms or between one oxygen and one sulphur atom and the ring as a whole must have chemical stability. Heteroatoms may optionally be present in all the possible oxidation stages (sulphur→sulphoxide —SO, sulphone —$SO_2$—; nitrogen→N-oxide). In a heterocyclyl there is no heteroaromatic ring, i.e. no heteroatom is part of an aromatic system.

A direct result of the derivation from cycloalkyl, cycloalkenyl and aryl is that heterocyclyl is made up of the subgroups monocyclic heterorings, bicyclic heterorings, tricyclic heterorings and spiro-heterorings, which may be present in saturated or unsaturated form. By unsaturated is meant that there is at least one double bond in the ring system in question, but no heteroaromatic system is formed. In bicyclic heterorings two rings are linked together so that they have at least two (hetero)atoms in common. In spiro-heterorings a carbon atom (spiroatom) belongs to two rings together. If a heterocyclyl is substituted, the substitutions may take place independently of one another, in the form of mono- or polysubstitutions in each case, on all the hydrogen-carrying carbon and/or nitrogen atoms. Heterocyclyl itself may be linked as a substituent to the molecule via every suitable position of the ring system. When the heterocyclyl has a nitrogen atom, the preferred position to bind the heterocyclyl substituent to the molecule is the nitrogen atom.

Examples of heterocyclyl are tetrahydrofuryl, pyrrolidinyl, pyrrolinyl, imidazolidinyl, thiazolidinyl, imidazolinyl, pyrazolidinyl, pyrazolinyl, piperidinyl, piperazinyl, oxiranyl, aziridinyl, azetidinyl, 1,4-dioxanyl, azepanyl, diazepanyl, morpholinyl, thiomorpholinyl, homomorpholinyl, homopiperidinyl, homopiperazinyl, homothiomorpholinyl, thiomorpholinyl-5-oxide, thiomorpholinyl-S,S-dioxide, 1,3-dioxolanyl, tetrahydropyranyl, tetrahydrothiopyranyl, [1.4]-oxazepanyl, tetrahydrothienyl, homothiomorpholinyl-S,S-dioxide, oxazolidinonyl, dihydropyrazolyl, dihydropyrrolyl, dihydropyrazinyl, dihydropyridyl, dihydro-pyrimidinyl, dihydrofuryl, dihydropyranyl, tetrahydrothienyl-S-oxide, tetrahydrothienyl-S,S-dioxide, homothiomorpholinyl-5-oxide, 2,3-dihydroazet, 2H-pyrrolyl, 4H-pyranyl, 1,4-dihydropyridinyl, 8-azabicyclo[3.2.1]octyl, 8-azabicyclo[5.1.0]octyl, 2-oxa-5-azabicyclo[2.2.1]heptyl, 8-oxa-3-aza-bicyclo[3.2.1]octyl, 3,8-diaza-bicyclo[3.2.1]octyl, 2,5-diazabicyclo-[2.2.1]heptyl, 1-aza-bicyclo[2.2.2]octyl, 3,8-diazabicyclo[3.2.1]octyl, 3,9-diaza-bicyclo[4.2.1]nonyl, 2,6-diaza-bicyclo[3.2.2]nonyl, 1,4-dioxa-spiro[4.5]decyl, 1-oxa-3.8-diaza-spiro[4.5]decyl, 2,6-diaza-spiro[3.3]heptyl, 2,7-diaza-spiro[4.4]nonyl, 2,6-diaza-spiro[3.4]octyl, 3,9-diaza-spiro[5.5]undecyl, 2.8-diaza-spiro[4.5]decyl etc.

Further examples are the structures illustrated below, which may be attached via each hydrogen-carrying atom (exchanged for hydrogen):
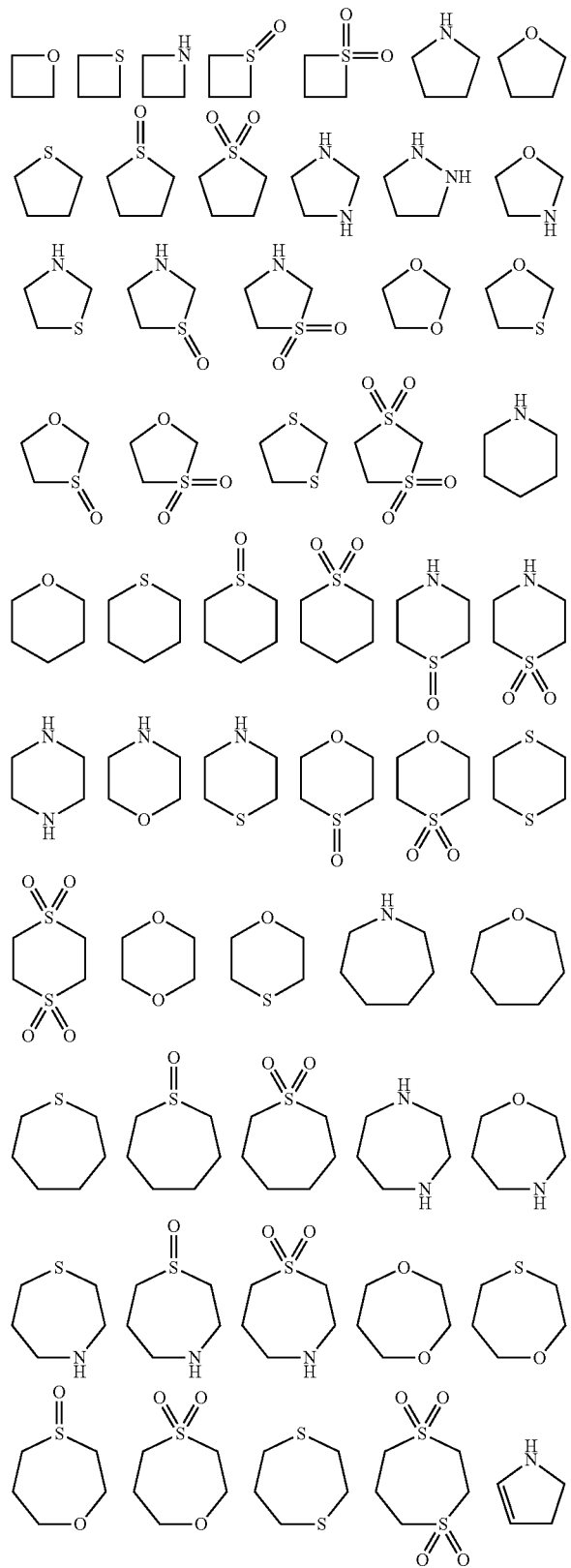
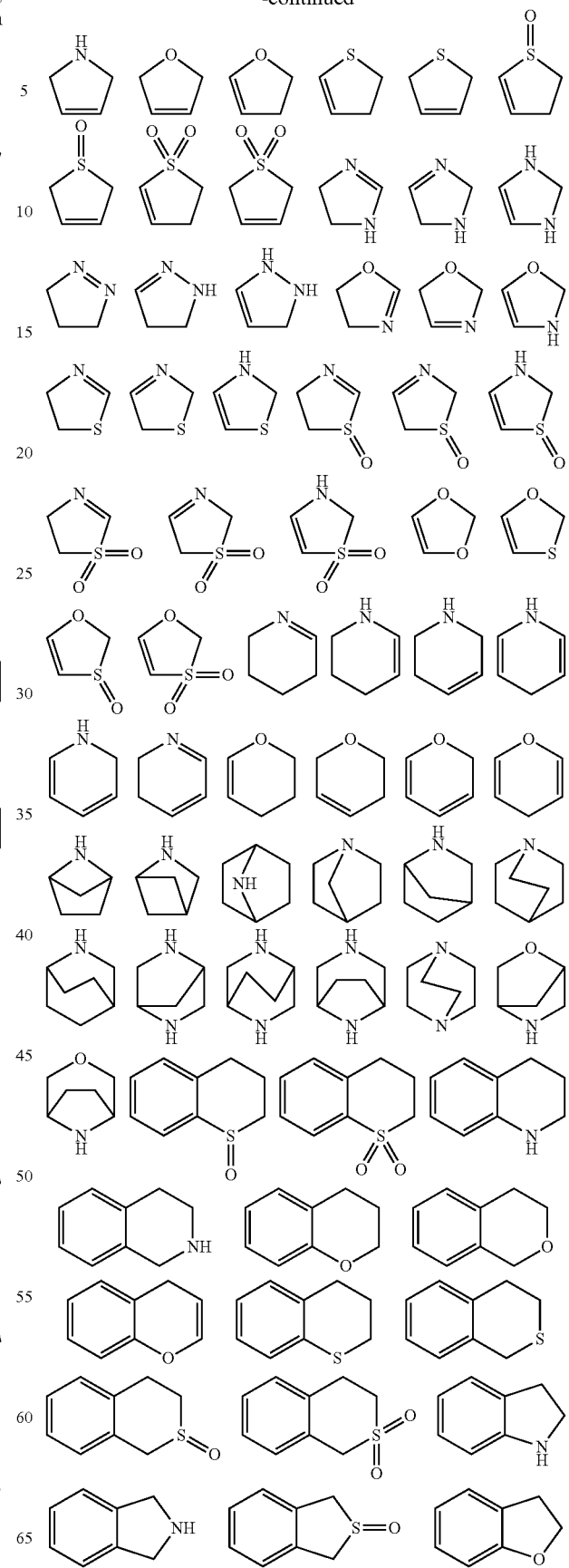

-continued

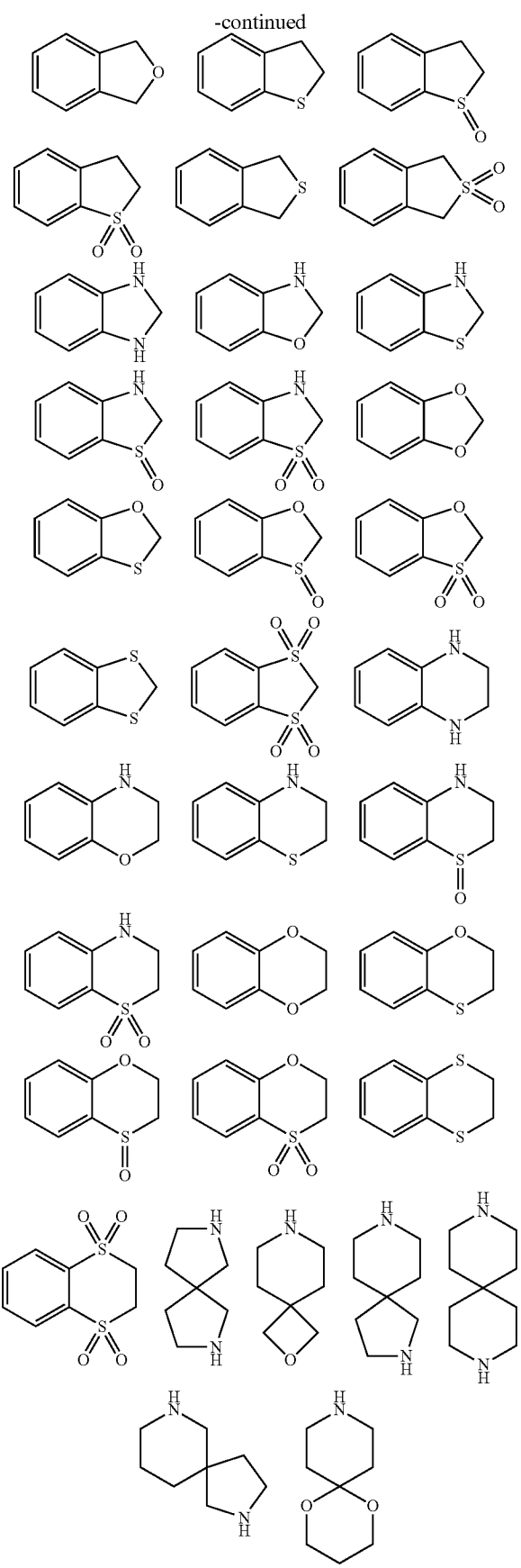

The above definition of heterocyclyl also applies if heterocyclyl is part of another group as in heterocyclylamino or heterocyclyloxy for example.

If the free valency of a heteroyclyl is saturated, then a heterocyclic group is obtained. The term heterocyclylene is also derived from the previously defined heterocyclyl. Heterocyclylene, unlike heterocyclyl, is bivalent and requires two binding partners. Formally, the second valency is obtained by removing a hydrogen atom from a heterocyclyl. Corresponding groups are for example piperidinyl and

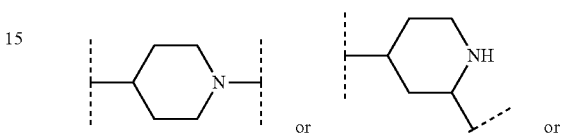

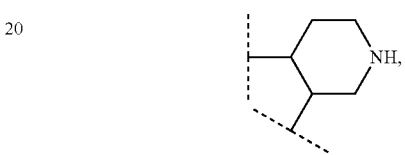

2,3-dihydro-1H-pyrrolyl and

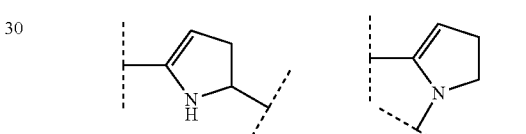

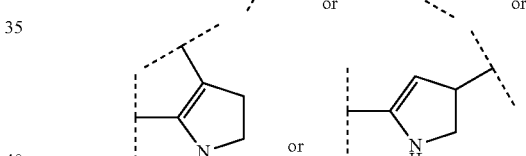

etc.

The above definition of heterocyclylene also applies if heterocyclylene is part of another group as in HO-heterocyclyleneamino or $H_2N$-heterocyclyleneoxy for example.

Heteroaryl denotes monocyclic heteroaromatic rings or polycyclic rings with at least one heteroaromatic ring, which compared with the corresponding aryl or cycloalkyl (cycloalkenyl) contain, instead of one or more carbon atoms, one or more identical or different heteroatoms, selected independently of one another from among nitrogen, sulphur and oxygen, wherein the resulting group must be chemically stable. The prerequisite for the presence of heteroaryl is a heteroatom and a heteroaromatic system. If a heteroaryl is to be substituted, the substitutions may take place independently of one another, in the form of mono- or polysubstitutions in each case, on all the hydrogen-carrying carbon and/or nitrogen atoms. Heteroaryl itself may be linked as a substituent to the molecule via every suitable position of the ring system, both carbon and nitrogen.

Examples of heteroaryl are furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl, triazinyl, pyridyl-N-oxide, pyrrolyl-N-oxide, pyrimidinyl-N-oxide, pyridazinyl-N-oxide, pyrazinyl-N-oxide, imidazolyl-N-oxide, isoxazolyl-N-oxide, oxazolyl-N-oxide, thiazolyl-N-oxide, oxadiazolyl-N-oxide, thiadiazolyl-N-oxide, triazolyl-N-oxide, tetrazolyl-N-oxide, indolyl, isoindolyl, benzofuryl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl, benzotriazinyl, indolizinyl, oxazolopyridyl, imidazopyridyl, naphthyridinyl, benzoxazolyl, pyridopyridyl, purinyl, pteridinyl, benzothiazolyl, imidazopyridyl, imidazothiazolyl, quinolinyl-N-oxide, indolyl-N-oxide, isoquinolyl-N-oxide, quinazolinyl-N-oxide, quinoxalinyl-N-oxide, phthalazinyl-N-oxide, indolizinyl-N-oxide, indazolyl-N-oxide, benzothiazolyl-N-oxide, benzimidazolyl-N-oxide etc.

Further examples are the structures illustrated below, which may be attached via each hydrogen-carrying atom (exchanged for hydrogen):

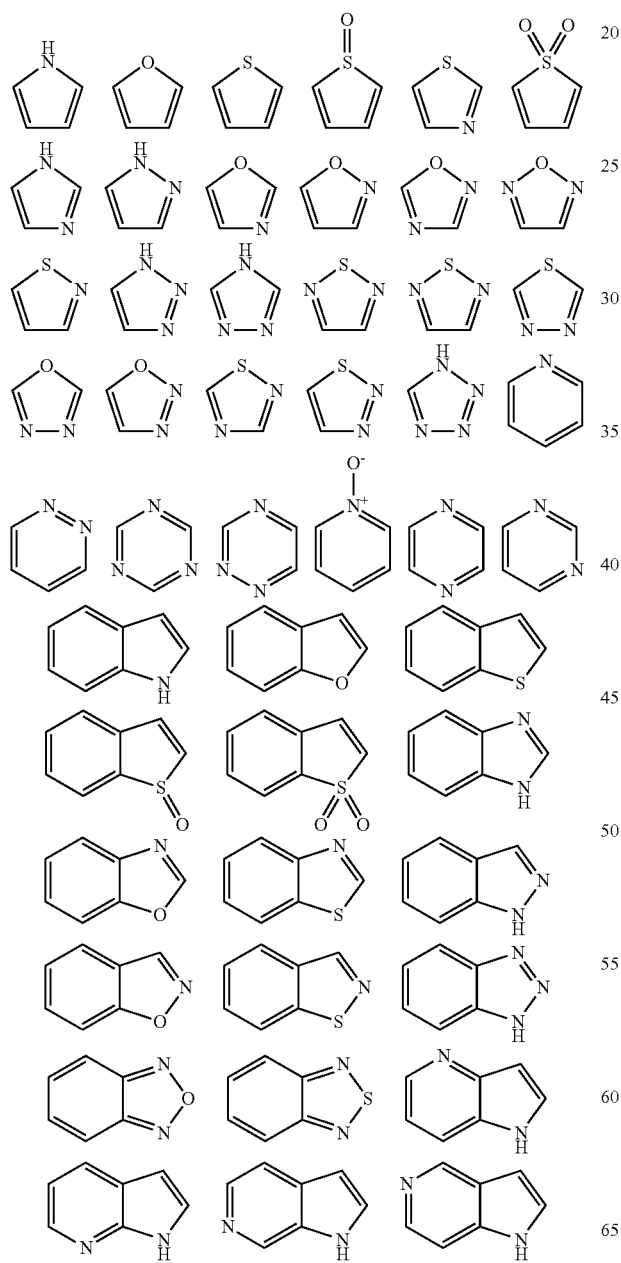

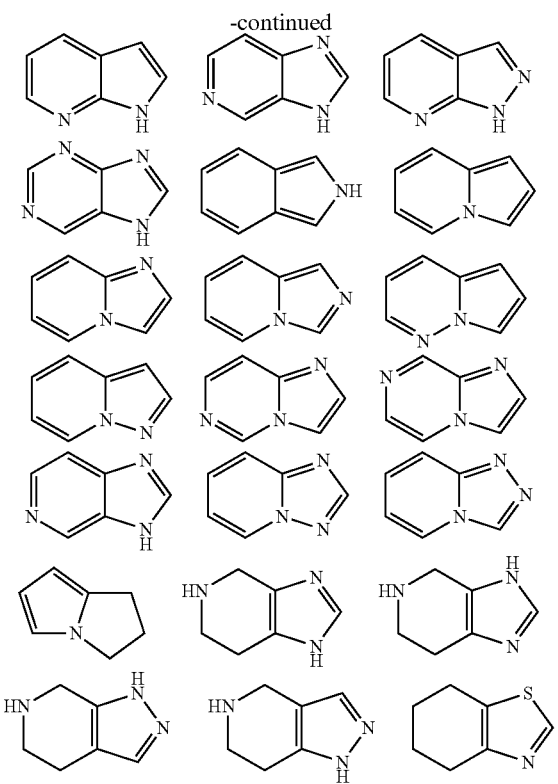

The above definition of heteroaryl also applies when heteroaryl is part of another group as in heteroarylamino or heteroaryloxy, for example.

If the free valency of a heteroaryl is saturated, a heteroaromatic group is obtained.

The term heteroarylene can therefore be derived from the previously defined heteroaryl. Heteroarylene, unlike heteroaryl, is bivalent and requires two binding partners. Formally, the second valency is obtained by removing a hydrogen atom from a heteroaryl. Corresponding groups are for example pyrrolyl and

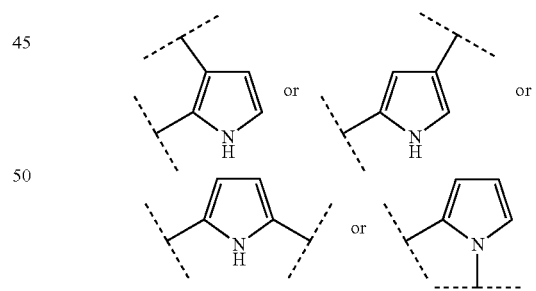

The above definition of heteroarylene also applies when heteroarylene is part of another group as in HO-heteroaryleneamino or $H_2N$-heteroaryleneoxy, for example.

The bivalent groups mentioned above (alkylene, alkenylene, alkynylene etc.) may also be part of composite groups (e.g. $H_2N$—$C_{1-4}$alkylene- or HO—$C_{1-4}$alkylene-). In this case one of the valencies is saturated by the attached group (here: —$NH_2$, —OH), so that a composite group of this kind written in this way is only a monovalent substituent over all.

By substituted is meant that a hydrogen atom which is bound directly to the atom under consideration, is replaced by another atom or another group of atoms (substituent). Depending on the starting conditions (number of hydrogen atoms) mono- or polysubstitution may take place on one atom. Substitution with a particular substituent is only possible if the permitted valencies of the substituent and of the atom that is to be substituted correspond to one another and the substitution leads to a stable compound (i.e. to a compound which is not converted spontaneously, e.g. by rearrangement, cyclisation or elimination).

In a preferred embodiment, "one or more substituents" refers to "one, two or three substituents", more preferably, "one or two substituents".

Bivalent substituents such as =S, =NR, =NOR, =NNRR, =NN(R)C(O)NRR, =N$_2$ or the like, may only be substituted at carbon atoms, wherein the bivalent substituent =O may also be a substituent at sulphur. Generally, substitution may be carried out by a bivalent substituent only at ring systems and requires replacement by two geminal hydrogen atoms, i.e. hydrogen atoms that are bound to the same carbon atom that is saturated prior to the substitution. Substitution by a bivalent substituent is therefore only possible at the group —CH$_2$— or sulphur atoms of a ring system.

Stereochemistry/Solvates/Hydrates: Unless stated otherwise a structural formula given in the description or in the claims or a chemical name refers to the corresponding compound itself, but also encompasses the tautomers, stereoisomers, optical and geometric isomers (e.g. enantiomers, diastereomers, E/Z isomers, etc.), racemates, mixtures of separate enantiomers in any desired combinations, mixtures of diastereomers, mixtures of the forms mentioned hereinbefore (if such forms exist) as well as salts, particularly pharmaceutically acceptable salts thereof. The compounds and salts according to the invention may be present in solvated form (e.g. with pharmaceutically acceptable solvents such as e.g. water, ethanol etc.) or in unsolvated form. Generally, for the purposes of the present invention the solvated forms, e.g. hydrates, are to be regarded as of equal value to the unsolvated forms.

Salts: The term "pharmaceutically acceptable" is used herein to denote compounds, materials, compositions and/or formulations which are suitable, according to generally recognised medical opinion, for use in conjunction with human and/or animal tissue and do not have or give rise to any excessive toxicity, irritation or immune response or lead to other problems or complications, i.e. correspond overall to an acceptable risk/benefit ratio.

The term "pharmaceutically acceptable salts" relates to derivatives of the chemical compounds disclosed in which the parent compound is modified by the addition of acid or base. Examples of pharmaceutically acceptable salts include (without being restricted thereto) salts of mineral or organic acids in relation to basic functional groups such as for example amines, alkali metal or organic salts of acid functional groups such as for example carboxylic acids, etc. These salts include in particular acetate, ascorbate, benzenesulphonate, benzoate, besylate, bicarbonate, bitartrate, bromide/hydrobromide, Ca-edetate/edetate, camsylate, carbonate, chloride/hydrochloride, citrate, edisylate, ethane disulphonate, estolate, esylate, fumarate, gluceptate, gluconate, glutamate, glycolate, glycollylarsnilate, hexylresorcinate, hydrabamine, hydroxymaleate, hydroxynaphthoate, iodide, isothionate, lactate, lactobionate, malate, maleate, mandelate, methanesulphonate, mesylate, methylbromide, methylnitrate, methylsulphate, mucate, napsylate, nitrate, oxalate, pamoate, pantothenate, phenyl acetate, phosphate/diphosphate, polygalacturonate, propionate, salicylate, stearate, subacetate, succinate, sulphamide, sulphate, tannate, tartrate, teoclate, toluenesulphonate, triethiodide, ammonium, benzathine, chloroprocaine, choline, diethanolamine, ethylenediamine, meglumin and procaine. Other pharmaceutically acceptable salts may be formed with cations of metals such as aluminium, calcium, lithium, magnesium, potassium, sodium, zinc, etc. (cf. also Pharmaceutical salts, Birge, S. M. et al., J. Pharm. Sci., (1977), 66, 1-19).

The pharmaceutically acceptable salts of the present invention may be prepared starting from the parent compound which carries a basic or acidic functionality, by conventional chemical methods. Generally, such salts may be synthesised by reacting the free acid or base form of these compounds with a sufficient amount of the corresponding base or acid in water or an organic solvent such as for example ether, ethyl acetate, ethanol, isopropanol, acetonitrile (or mixtures thereof).

Salts of acids other than those mentioned above, which are useful for example for purifying or isolating the compounds from the reaction mixtures (e.g. trifluoroacetates), are also to be regarded as part of the invention.

In a representation such as for example

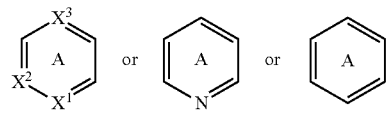

the letter A has the function of a ring designation in order to make it easier, for example, to indicate the attachment of the ring in question to other rings.

For bivalent groups in which it is crucial to determine which adjacent groups they bind and with which valency, the corresponding binding partners are indicated in brackets, where necessary for clarification purposes, as in the following representations:

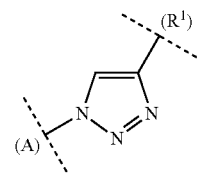

or (R$^2$)—C(O)NH— or (R$^2$)—NHC(O)—;

Groups or substituents are frequently selected from among a number of alternative groups/substituents with a corresponding group designation (e.g. R$^a$, R$^b$ etc). If such a group is used repeatedly to define a compound according to the invention in different molecular parts, it must always be borne in mind that the various uses are to be regarded as totally independent of one another.

By a therapeutically effective amount for the purposes of this invention is meant a quantity of substance that is capable of obviating symptoms of illness or of preventing or alleviating these symptoms, or which prolong the survival of a treated patient.

LIST OF ABBREVIATIONS

| bu | butyl | tert | tertiary |
|---|---|---|---|
| d | day(s) | THF | tetrahydrofuran |
| DC | thin layer chromatography | LiHMDS | Lithium hexamethyl disilazide |

-continued

| | | | |
|---|---|---|---|
| DCM | dichloromethane | iPr | isopropyl |
| DMF | N,N-dimethylformamide | MTBE | tertiary butylmethylether |
| DMSO | dimethylsulphoxide | NP | normal phase |
| et | ethyl | CDI | carbonyl diimidazole |
| h | hour(s) | ACN | acetonitrile |
| HPLC | high performance liquid chromatography | BINAP | 2R,3S,2,2'-bis-(diphenyl-phosphino)-1,1'-binapthyl |
| M | molar | DIPEA | diisopropylethyl amine |
| me | methyl | NP | normal phase |
| min | minute(s) | DCE | 1,2-dichloroethane |
| mL | millilitre | NMP | N-methylpyrrolindinone |
| MS | mass spectrometry | prep | preparative |
| N | normal | conc. | concentrated |
| NMR | nuclear resonance spectroscopy | TFA | trifluoroacetic acid |
| ppm | part per million | HATU | N-[(dimethylamino)-(1H-1,2,3-triazolo[4,5-b]pyridin-1-yl)-methylene]-N-methylmethan-aminium hexafluorophosphate N-oxide |
| $R_f$ | retention factor | DMA | N,N-dimethylacetamide |
| RP | reversed phase | m.p. | melting point |
| RT | room temperature | DBU | 1,8-diazabicyclo[5.4.0]undec-7-ene |
| tR | retention time | DMAP | dimethyl-pyridin-4-yl-amine |

Other features and advantages of the present invention will become apparent from the following more detailed Examples which exemplary illustrate the principles of the invention without restricting its scope.

General

Unless stated otherwise, all the reactions are carried out in commercially obtainable apparatus using methods that are commonly used in chemical laboratories. Starting materials that are sensitive to air and/or moisture are stored under protective gas and corresponding reactions and manipulations therewith are carried out under protective gas (nitrogen or argon).

The compounds are named according to the Beilstein rules using the Autonom software (Beilstein). If a compound is to be represented both by a structural formula and by its nomenclature, in the event of a conflict the structural formula is decisive.

Chromatography

Thin layer chromatography is carried out on ready-made TLC plates of silica gel 60 on glass (with fluorescence indicator F-254) made by Merck.

The preparative high pressure chromatography (HPLC) of the example compounds according to the invention is carried out with columns made by Waters (names: Sunfire C18, 5 μm, 30×100 mm Part. No. 186002572; X-Bridge C18, 5 μm, 30×100 mm Part. No. 186002982). The compounds are eluted using either different gradients of $H_2O$/acetonitrile or $H_2O$/MeOH, wherein 0.1% HCOOH is added to the water (acid conditions). For chromatography under basic conditions $H_2O$/acetonitrile gradients are also used, and the water is made basic according to the following recipe: 5 mL of ammonium hydrogen carbonate solution (158 g to 1 L $H_2O$) and 2 mL ammonia (7M in MeOH) are made up to 1 L with $H_2O$.

The normal-phase preparative high pressure chromatography (HPLC) of the example compounds according to the invention is carried out with columns made by Macherey & Nagel (name: Nucleosil, 50-7, 40×250 mm) and VDSoptilab (name: Kromasil 100 $NH_2$, 10 μM, 50×250 mm). The compounds are eluted using different gradients of DCM/MeOH, with 0.1% $NH_3$ added to the MeOH.

The analytical HPLC (reaction monitoring) of intermediate compounds is carried out with columns made by Agilent, Waters and Phenomenex. The analytical equipment is also provided with a mass detector in each case.

HPLC Mass Spectroscopy/UV Spectrometry

The retention times/MS-ESI⁺ for characterising the example compounds according to the invention are produced using an HPLC-MS apparatus (high performance liquid chromatography with mass detector) made by Agilent. Compounds that elute at the injection peak are given the retention time tR=0.

Analytical Method

| | | |
|---|---|---|
| HPLC: | Agilent 1100 Series | |
| MS: | Agilent LC/MSD SL | |
| Column: | Waters, XBridge ™ C18, 2.5 μm, 2.1 × 20 mm Part. No. 186003201 | |
| Solvent | A: 0.1% $NH_3$ (=pH 9-10) B: Acetonitrile HPLC grade | |
| Detection: | MS: | Positive and negative |
| | Mass range: | 120-800 m/z |
| | Fragmentor: | 70 |
| | Gain EMV: | 1 |
| | Threshold: | 150 |
| | Stepsize: | 0.25 |
| | UV: | 315 nm |
| | Bandwidth: | 170 nm |
| | Reference: | off |
| | Range: | 230-400 nm |
| | Range step: | 2.00 nm |
| | Peak width: | <0.01 min |
| | Slit: | 2 nm |
| Injection: | 5 μL | |
| Flow: | 1.00 mL/min | |
| Column temperature: | 60° C. | |
| Gradient: | 0.00 min | 5% B |
| | 0.00-2.50 min | 5% -> 95% B |
| | 2.50-2.80 min | 95% B |
| | 2.81-3.10 min | 95% -> 5% B |

Preparation of the Compounds According to the Invention

The compounds according to the invention are prepared by the methods of synthesis described hereinafter, in which the substituents of the general formulae have the meanings given hereinbefore. These methods are intended as an illustration of the invention, without restricting its subject matter and the scope of the compounds claimed to these examples. Where the preparation of starting compounds is not described, they are commercially obtainable or may be prepared analogously to known compounds or methods described herein. Substances described in the literature are prepared according to the published methods of synthesis.

Unless otherwise specified, the substituents $R^1$ through $R^6$ and n of the following reaction schemes are as defined above.

The compounds of formula I may be prepared according to the following schemes (1-5):

Scheme 1

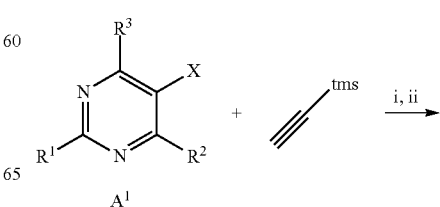

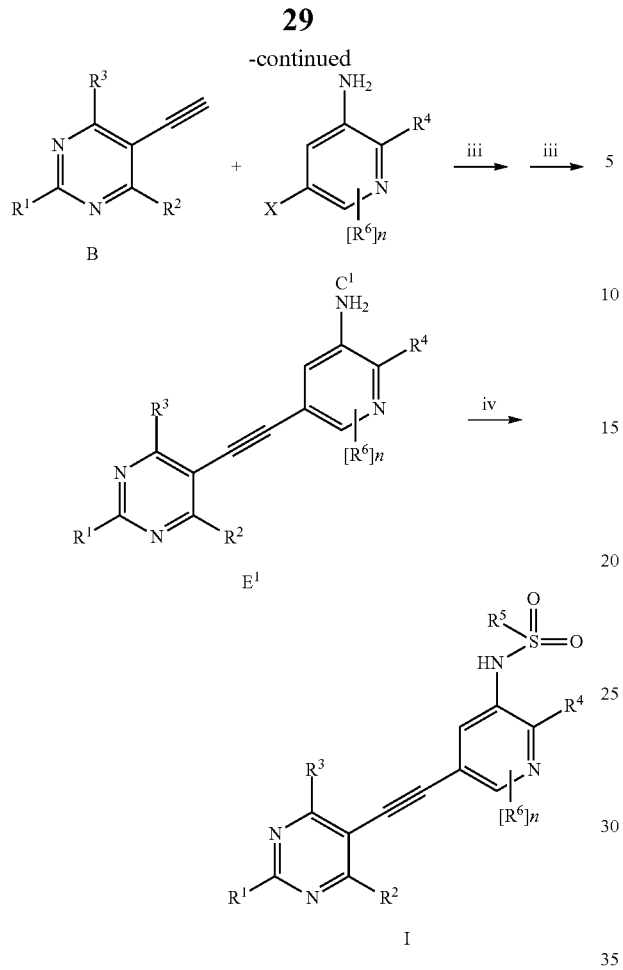

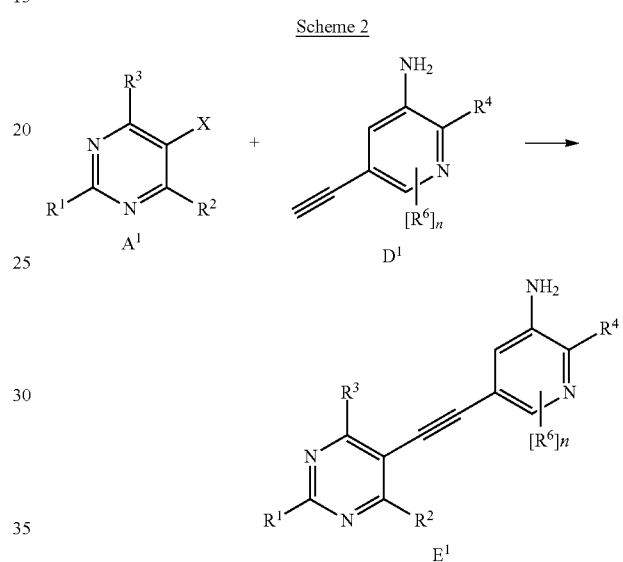

Scheme 2

One method for the preparation of compounds of formula I starts from intermediates of formula $A^1$ as depicted in scheme 1. Intermediates of formula $A^1$, wherein X is bromine or iodine, preferably iodine, are commercially available or may be prepared according to methods well known in the art. In step (i) intermediate $A^1$ is reacted with trimethylsilylacetylene in a solvent (for example THF, DMF, DMSO, 1,2-dimethoxyethane or dioxane, preferably DMF), containing a palladium catalyst, preferably bis(triphenylphosphine)palladium(II) chloride, a copper co-catalyst, preferably copper(I) iodide, and an excess of an organic base, preferably triethylamine. The reaction is carried out at elevated temperature, preferably 60° C., for about 1-16 h, preferably about 3 h. The product is isolated by conventional means and preferably purified by chromatography.

Intermediates of formula B are prepared in step (ii) by the reacting the products obtained in step (i) with base, preferably potassium carbonate, in a solvent, preferably MeOH, at RT for 3 h. Intermediates B are isolated by conventional means and used as such or are purified by chromatography.

Intermediates of formula $E^1$ are obtained in step (iii) by reacting intermediates B with intermediates of formula $C^1$, wherein X is bromide or iodide, preferably bromide. Intermediates of formula $C^1$ are commercially available or may be prepared according to methods well known in the art. In step (iii) intermediate B is reacted with intermediate $C^1$ in a solvent (for example THF, DMF, DMSO, 1,2-dimethoxyethane or dioxane, preferably DMF), containing a palladium catalyst, preferably bis(triphenylphosphine)palladium(II) chloride, a copper co-catalyst, preferably copper(I) iodide, and an excess of an organic base, preferably triethylamine. The reaction is carried out at elevated temperature, preferably 50° C. or 75° C., for several h, preferably over night. Intermediates $E^1$ are isolated by conventional means and preferably purified by chromatography.

Compounds of formula I are prepared by reacting intermediates $E^1$ with $R^5$-sulfonyl chlorides. $R^5$-sulfonyl chlorides are commercially available or may be prepared according to methods well known in the art. In step (iv) intermediate $E^1$ is reacted with an $R^5$-sulfonyl chloride in a solvent, preferably DCM, containing an excess of base, preferably pyridine, at RT overnight. Compounds I are isolated by conventional means and preferably purified by chromatography.

Another method for the preparation of intermediates $E^1$ is based on the reaction of intermediates $A^1$ with intermediates of formula $D^1$ as depicted in scheme 2. Intermediates $D^1$ may be prepared according to methods well known in the art. Intermediate $A^1$ is reacted with intermediate $D^1$ in a solvent (for example THF, DMF, DMSO, 1,2-dimethoxyethane or dioxane, preferably THF or DMSO), containing a palladium catalyst, preferably tetrakis(triphenylphosphine)palladium (0), a copper co-catalyst, preferably copper(I) iodide, and an excess of an organic base, preferably triethylamine or DIPEA. The reaction is carried out at elevated temperature, preferably 45-80° C., more preferably 75° C., for about several h, preferably overnight. Intermediate $E^1$ is isolated by conventional means and preferably purified by chromatography. Intermediates $E^1$ can be converted to compounds of formula I by the method described above.

Scheme 3

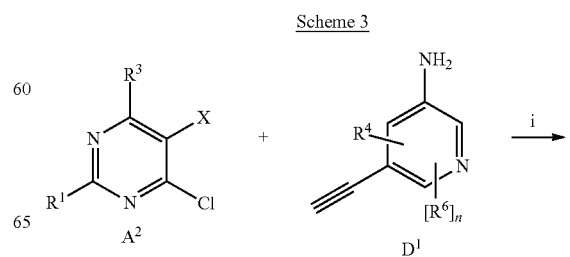

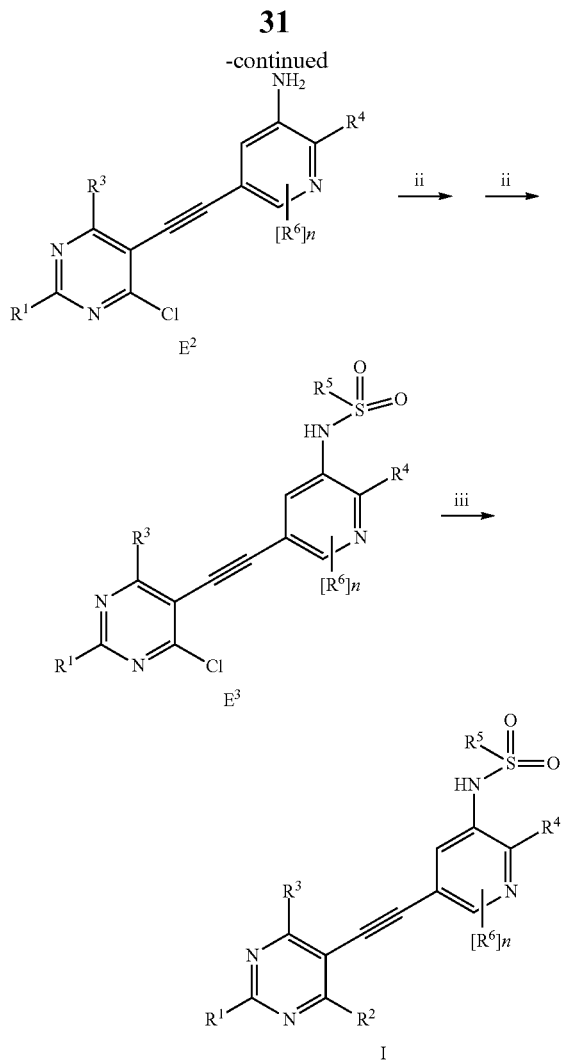

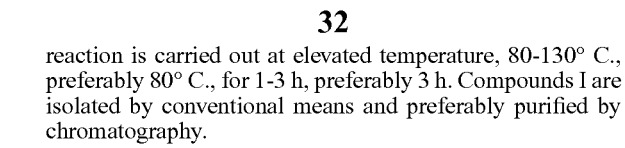

An alternative method for the preparation of compounds of formula I is depicted in scheme 3. Intermediates of formula $A^2$, wherein X is bromine or iodine, preferably iodine, are commercially available or may be prepared according to methods well known in the art. In step (i) intermediate $A^2$ is reacted with intermediate $D^1$ in a solvent (for example THF, DMF, DMSO, 1,2-dimethoxyethane or dioxane, preferably DMSO), containing a palladium catalyst, preferably tetrakis(triphenylphosphine)palladium(0), a copper co-catalyst, preferably copper(I) iodide, and an excess of an organic base, preferably diisopropylamine or triethylamine, to give intermediate $E^2$. The reaction is carried out at elevated temperature, preferably 60-65° C., for several h, preferably overnight. Intermediate $E^2$ is isolated by conventional means and preferably purified by chromatography.

Intermediates $E^3$ are obtained in step (ii) by reacting intermediates $E^2$ with $R^5$-sulfonyl chlorides in a solvent, preferably DCM, containing an excess of base, preferably pyridine or lutidine, at RT overnight. Intermediates $E^3$ are isolated by conventional means and preferably purified by chromatography.

Compounds of formula I are prepared by reacting intermediates $E^3$ with amines $R^2$. Amines $R^2$ are commercially available or may be prepared according to methods well known in the art. In step (iv) intermediate $E^3$ is reacted with an amine $R^2$ in a solvent, for example THF, NMP, dioxane and DMF, preferably dioxane, with or without an excess of base, preferably with triethylamine or diisopropylethylamine. The reaction is carried out at elevated temperature, 80-130° C., preferably 80° C., for 1-3 h, preferably 3 h. Compounds I are isolated by conventional means and preferably purified by chromatography.

Scheme 4

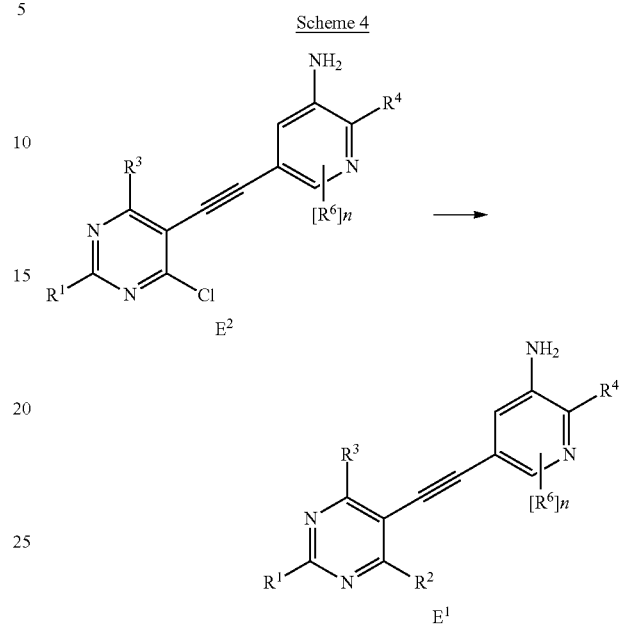

In an alternative method intermediates $E^2$ are converted in intermediates $E^1$ as depicted in scheme 4. Intermediate $E^2$ is reacted with an amine $R^2$ in a solvent, for example THF, NMP, dioxane and DMF, preferably dioxane, with an excess of base, preferably diisopropylethylamine. The reaction is carried out at elevated temperature, preferably 80° C., for several h, preferably overnight. Intermediates $E^1$ are isolated by conventional means and preferably purified by chromatography.

Scheme 5

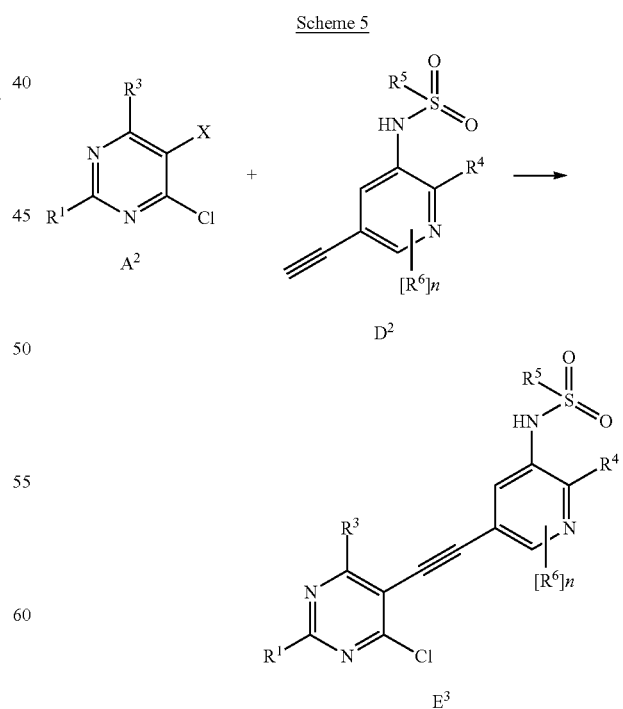

In yet another alternative method intermediates of formula $E^3$ are prepared by reacting intermediates $A^2$ with intermediates $D^2$ as depicted in scheme 5. Intermediates of formula $D^2$ may be prepared according to methods well known in the art. Intermediate $A^2$ is reacted with intermediate $D^2$ in a solvent (for example THF, DMF, DMSO, 1,2-dimethoxyethane or dioxane, preferably THF, DMF or DMSO), containing a palladium catalyst, preferably tetrakis(triphenylphosphine)palladium(0) or bis(triphenylphospine)palladium(II) chloride, a copper co-catalyst, preferably copper(I) iodide, and an excess of an organic base, preferably triethylamine or diisopropylamine. The reaction is carried out at elevated temperature, preferably 65° C., for about 1-16 h, preferably 4 h. Intermediate $E^3$ is isolated by conventional means and preferably purified by chromatography. Intermediates $E^3$ can be converted to compounds of formula I by the method described above.

Preparation of intermediates A

A-1) 6-Methyl-3H-pyrimidin-4-one

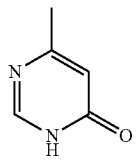

100 g (0.70 mol) 4-Hydroxy-2-mercapto-6-methyl-pyrimidine and 300 g Raney-Nickel are suspended in water (1000 mL) and the suspension is heated and stirred under reflux over night. The reaction mixture is filtered over celite and the filtrate is concentrated under reduced pressure to give crude product.

A-2) 5-Iodo-6-methyl-3H-pyrimidin-4-one

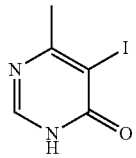

To 70 g (0.64 mol) A-1 in acetic acid is added 127 g (0.56 mol) NIS portion wise at RT within 15 min. The reaction is stirred at RT until all starting material is consumed (30 h). The reaction mixture is diluted with water and the solid product is filtered off, washed with an aqueous sodium thiosulfate solution to remove excess iodine and dried in vacuo. Yield: 90 g (60%).

A-3) 4-Chloro-5-iodo-6-methyl-pyrimidine

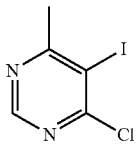

A mixture of 90 g (0.38 mol) A-2 in 600 mL POCl$_3$ is heated for 1 h at 90° C. The reaction mixture is concentrated under reduced pressure and the residue is poured into crushed ice. The precipitated solid is collected by filtration, washed with water and dried in vacuo. Yield: 90 g (93%). $^1$H NMR (CDCl$_3$) δ: 8.7 (s, 1H), 2.8 (s, 3H). TLC (silica, 10% MeOH in DCM): R$_f$=0.85.

A-4) 6-Ethyl-3H-pyrimidin-4-one

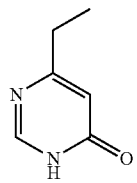

90 g (0.58 mol) 4-Hydroxy-2-mercapto-6-ethylpyrimidine and 270 g Raney-Nickel are suspended in water (1000 mL) and the suspension is heated and stirred under reflux over night. The reaction mixture is filtered over celite and the filtrate is concentrated under reduced pressure to give crude product. Yield: 70.0 g (98%).

A-5) 6-Ethyl-5-iodo-3H-pyrimidin-4-one

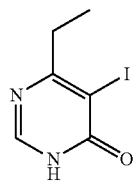

To 70 g (0.56 mol) A-4 in acetic acid is added 127 g (0.56 mol) NIS portion wise at RT within 15 min. The reaction is stirred at RT until all starting material is consumed (30 h). The reaction mixture is diluted with water and the solid product is filtered off, washed with an aqueous sodium thiosulfate solution to remove excess iodine and dried in vacuo. Yield: 90 g (64%).

A-6) 4-Chloro-6-ethyl-5-iodo-pyrimidine

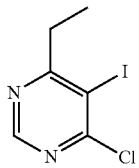

A suspension of 90 g (0.36 mol) A-5 in 600 mL POCl$_3$ is heated for 1 h at 90° C. The reaction mixture is concentrated under reduced pressure and the residue is poured into crushed ice. The precipitated product is collected by filtration, washed with water and dried in vacuo. Yield: 65 g (67%). $^1$H NMR (CDCl$_3$) δ: 8.7 (s, 1H), 3.0 (quart., 2H), 1.3 (tripl., 3H). TLC (silica, 10% MeOH in DCM): R$_f$=0.80.

A-7) 4-Chloro-5-iodo-6-methyl-pyrimidin-2-ylamine

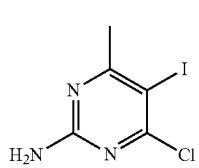

10.0 g (70 mmol) 4-Chloro-6-methyl-pyrimidin-2-ylamine in 200 mL acetic acid is cooled to 0° C., 15.7 g (70 mmol) NIS is added and the reaction mixture is stirred at RT until conversion of the starting material is completed (18 h). An aqueous solution of 5% $Na_2S_2O_3$ and 10% $NaHCO_3$ is added until the mixture decolorizes. The formed precipitate is filtered off, taken up with water and the resulting suspension is stirred at RT for 1 h. The product is filtered off and dried in vacuo at 40° C. Yield: 15.2 g (81%). $^1$H NMR ($CDCl_3$) δ: 5.2 (s, 2H), 2.6 (s, 3H). TLC (silica, 20% EtOAc in PE): $R_f$=0.50.

A-8) 4-Chloro-6-ethyl-5-iodo-pyrimidin-2-ylamine

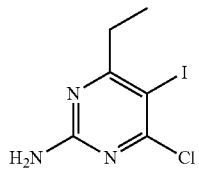

25.0 g (159 mmol) 4-Chloro-6-ethyl-pyrimidin-2-ylamine in 1.0 L acetic acid is cooled to 0° C. and 36.0 g (159 mmol) NIS is added in one portion. The reaction mixture is stirred at RT until conversion of the starting material is completed (18 h). An aqueous solution of 5% $Na_2S_2O_3$ and 10% $NaHCO_3$ is added until the mixture decolorizes. The formed precipitate is filtered off, taken up with water and the suspension stirred at RT for 60 minutes. The product is filtered off, washed with diethyl ether and dried in vacuo at 40° C. Yield: 40.3 g (90%). $^1$H NMR (DMSO-$d_6$) δ: 7.2 (s, 2H), 2.7 (quart., 2H), 1.1 (tripl., 3H). HPLC-MS: tR=1.62 min., (M+H)=284.

A-9) 4-(5-Iodo-6-methyl-pyrimidin-4-yl)-morpholine

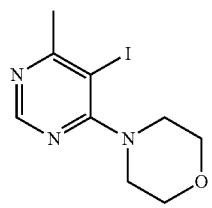

10 g (39 mmol) A-3, 4.1 mL (47 mmol) morpholine and 16 g (118 mmol) potassium carbonate are suspended in acetonitrile and stirred at 80° C. for three h. The reaction mixture is cooled to RT, filtered and the filtrate is concentrated under reduced pressure. Yield: 12 g (100%).

A-10) 4-(6-Ethyl-5-iodo-pyrimidin-4-yl)-morpholine

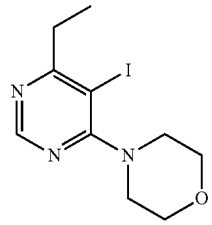

A mixture of 4.34 g (16.2 mmol) A-6, 1.69 mL (19.4 mL) morpholine and 6.70 g (48.5 mmol) potassium carbonate in 50 mL acetonitrile is stirred at 80° C. for 3 h. The reaction mixture is cooled to RT, filtered and the filtrate is concentrated under reduced pressure. Yield: 3.99 g (77%).

Preparation Of Intermediates B

B-1) 4-(6-Ethyl-5-trimethylsilanylethynyl-pyrimidin-4-yl)-morpholine

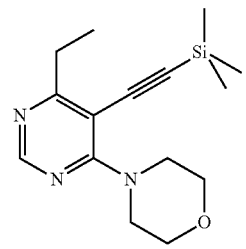 [SMILES: CCc1ncnc(N2CCOCC2)c1C#C[Si](C)(C)C]

Under argon atmosphere 0.25 g (1.3 mmol) copper(I) iodide and 0.39 g (0.55 mmol) bis(triphenylphospine)palladium(II) dichloride are added to a mixture of 3.90 g (11.0 mmol) A-10 in 15 mL dry DMF. Subsequently 15 mL (109 mmol) triethyl amine and 1.62 g (16.5 mmol) trimethylsilylacetylene are added and the reaction mixture is stirred for 3 h at 60° C. The reaction mixture is concentrated under reduced pressure and 200 mL water is added. The reaction mixture is extracted twice with 200 mL DCM and the combined organic phases are washed with water, dried over $MgSO_4$ and concentrated under reduced pressure. The product is purified by NP chromatography (silica gel, 2-18% MeOH containing 0.1% $NH_3$ in DCM). Yield: 2.44 g (77%).

B-2) 4-(6-Ethyl-5-ethynyl-pyrimidin-4-yl)-morpholine

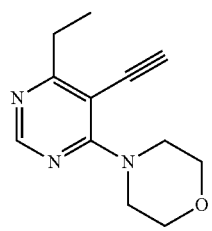 [SMILES: C#Cc1c(CC)ncnc1N1CCOCC1]

A mixture of 1.2 g (8.4 mmol) B-1 and 3.5 g (25 mmol) potassium carbonate in 10 mL MeOH and 40 mL THF is stirred for 3 h at RT. The reaction mixture is poured in water and extracted with DCM. The combined organic phases are dried over $MgSO_4$ and concentrated under reduced pressure. Yield: 0.90 g (49%).

B-3) 4-(6-Methyl-5-trimethylsilanylethynyl-pyrimidin-4-yl)-morpholine

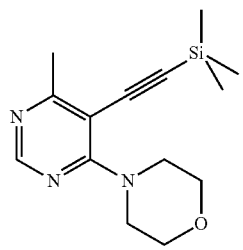 [SMILES: Cc1ncnc(N2CCOCC2)c1C#C[Si](C)(C)C]

Under argon atmosphere 0.18 g (0.94 mmol) copper(I) iodide and 0.33 g (0.47 mmol) bis(triphenylphospine)palladium(II) dichloride are added to a mixture of 3.20 g (9.44 mmol) A-9 in 15 mL dry DMF. Subsequently 13 mL (94 mmol) triethyl amine and 1.99 mL (14.2 mmol) trimethylsilylacetylene are added and the reaction mixture is stirred for 4 h at 60° C. and over night at 40° C. The reaction mixture is concentrated under reduced pressure and 200 mL water is added. The reaction mixture is extracted twice with 200 mL DCM and the combined organic phases are washed with water, dried over $MgSO_4$ and concentrated under reduced pressure. The product is purified by RP chromatography (C18, 10-80% acetonitrile in water 0.1% formic acid). Yield: 1.15 g (44%).

B-4) 4-(5-Ethynyl-6-methyl-pyrimidin-4-yl)-morpholine

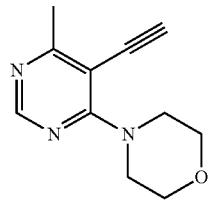

A mixture of 1.15 g (4.18 mmol) B-3 and 1.73 g (12.5 mmol) potassium carbonate in mL MeOH and 40 mL THF is stirred for 3 h at RT. The reaction mixture is poured in water and extracted with DCM. The combined organic phases are dried over $MgSO_4$ and concentrated under reduced pressure. The residue is purified by NP chromatography (silica gel, 1-15% MeOH containing 0.1% $NH_3$ in DCM) Yield: 0.85 g (100%).

Preparation of Intermediates C

C-1) 2-(5-Bromo-3-nitro-pyridin-2-yl)-malonic acid diethyl ester

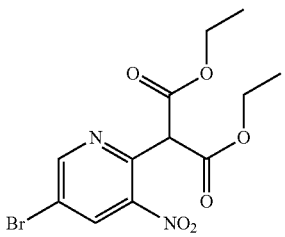 [SMILES: CCOC(=O)C(C(=O)OCC)c1ncc(Br)cc1[N+](=O)[O-]]

The title compound is prepared as described in WO 2006/103449 (intermediate 24).

A mixture of 20.2 g (842 mmol) sodium hydride in 500 mL dry THF is cooled to 0° C. and 33.7 g (211 mmol) diethyl malonate are added dropwise over 30 minutes. Subsequently, 2-chloro-5-bromo-3-nitro-pyridine (50.0 g, 211 mmol) is added in small portions so that the reaction temperature is kept at 0° C. After complete addition, the mixture is heated to 50° C. and stirred for 2 h. The reaction is poured into ice water and the product is extracted with EtOAc. The organic layer is separated, dried over $MgSO_4$ and the solvent is removed under reduced pressure. The product is purified by chromatography on silica gel. Yield: 50.0 g (66%).

C-2) 5-Bromo-2-methyl-3-nitro-pyridine

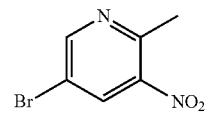

The title compound is prepared as described in WO 2006/103449 (intermediate 24).

C-1 (40.0 g, 111 mmol) is taken up in 110 mL 1N HCl and the reaction mixture is stirred under reflux for 3 h. After cooling to RT, the reaction mixture is extracted with DCM, the combined organic layers are washed with saturated aqueous $NaHCO_3$, dried over $MgSO_4$, filtered, and the solvent is removed under reduced pressure. Yield: 20.0 g (83%).

C-3) 5-Bromo-2-methyl-pyridin-3-yl-amine

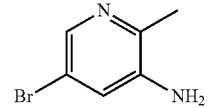

Iron powder (15.4 g, 276 mmol) and ammonium chloride (14.8 g, 276 mmol) are added to a solution of 20.0 g (92.2 mmol) C-2 in 180 mL EtOH. The mixture is stirred and heated until reflux for 3 h. The mixture is filtered through Celite and the solvent is evaporated under reduced pressure. The crude product is taken up with water and DCM, the organic phase is separated, dried over $MgSO_4$ and the solvent is removed under reduced pressure. The title compound is purified by chromatography on silica gel. Yield: 15.0 g (87%).

C-4) 5-Bromo-2-methoxy-3-nitro-pyridine

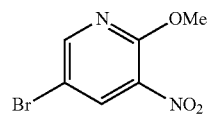

A solution of 20.0 g (84.2 mmol) 5-bromo-2-chloro-3-nitro-pyridine in 50 mL MeOH is cooled to 0° C. and 15.8 mL (84.2 mmol) of a NaOMe solution in MeOH (30%) is added drop wise. The mixture is stirred at RT over night and then stirred under reflux for 24 h. The precipitate is filtered off, suspended in water and the suspension is stirred for 1 h. The product is filtered off and dried und vacuum at 60° C. Yield: 18.7 g (95%).

C-5) 5-Bromo-2-methoxy-pyridin-3-yl-amine

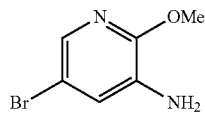

A solution of 985 mg (4.23 mmol) C-4 in 10 mL EtOAc is treated with 3.82 g (16.9 mmol) tin-II-chloride dihydrate. The mixture is stirred under reflux for 3 h. After cooling to RT, the solvent is removed under reduced pressure and the crude product is taken up in 9.5 mL aqueous 2 N NaOH. After stirring at RT for 1 h, DCM is added and the mixture is filtered over Celite. The aqueous phase is extracted with DCM, the combined organic layers are dried over MgSO$_4$ and the solvent is removed under reduced pressure. The crude product can be used without further purification. Yield: 647 mg (75%).

C-6) N-(5-Bromo-2-methyl-pyridin-3-yl)-methanesulfonamide

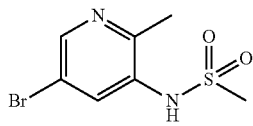

A mixture of 200 mg (1.1 mmol) C-3, 100 µL (1.3 mmol) methanesulfonyl chloride, 259 µL (3.2 mmol) pyridine and 5 mL DCM is stirred at RT for 3 h. The reaction mixture is filtered and the solvent is removed under reduced pressure. The crude product can be used without further purification. Yield: 200 mg (71%).

C-7) N-(5-Bromo-2-methyl-pyridin-3-yl)-2,4-difluoro-benzenesulfonamide

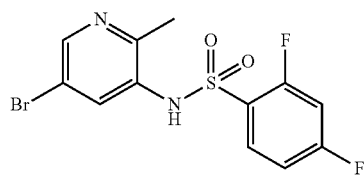 [SMILES: Cc1ncc(Br)cc1NS(=O)(=O)c1ccc(F)cc1F]

A mixture of 4.00 g (21.4 mmol) C-3, 4.3 mL (32 mmol) 2,4-difluorobenzenesulfonyl chloride, 5.2 mL (64 mmol) pyridine and 50 mL DCM is stirred at RT for 5 h. After completion of the reaction, the solvent is removed under reduced pressure, the crude product is taken up in 50 mL water and extracted twice with 100 mL DCM. The combined organic layers are dried over MgSO$_4$ and the solvent is removed under reduced pressure. The crude product can be used without further purification. Yield: 7.88 g (91%).

C-8) N-(5-Bromo-2-methoxy-pyridin-3-yl)-methanesulfonamide

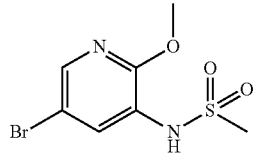

A mixture of 2.40 g (11.8 mmol) C-5, 1.1 mL (14 mmol) methanesulfonyl chloride, 2.9 mL (37 mmol) pyridine and 40 mL DCM is stirred under reflux for 1 h. After cooling to RT, 50 mL water is added and the mixture is stirred at RT for 10 min. The two phases are separated, the organic layer is extracted twice with 50 mL aqueous 5% citric acid and then concentrated under reduced pressure. The residue is purified by chromatography on silica gel. Yield: 2.5 g (75%).

C-9) N-(5-Bromo-2-methoxy-pyridin-3-yl)-2,4-difluoro-benzenesulfonamide

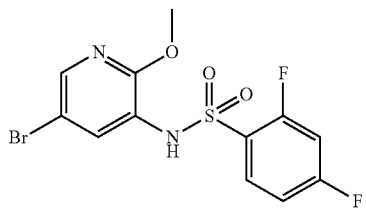 [SMILES: COc1ncc(Br)cc1NS(=O)(=O)c1ccc(F)cc1F]

A mixture of 1.80 g (8.8 mmol) C-5, 2.29 mL (17 mmol) 2,4-difluorobenzenesulphonyl chloride, 1.07 mL (13.3 mmol) pyridine and 20 mL DCM is stirred at RT over night. 100 mL DCM is added and the reaction mixture is extracted three times with 50 mL aqueous 1M HCl. The organic layer is dried over MgSO$_4$ and the solvent is removed under reduced pressure. The solid is dissolved in water/MeCN and further purified by RP-chromatograpy. Yield: 2.9 g (86%).

Preparation of Intermediates D

D-10) 2-Methyl-5-trimethylsilanylethynyl-pyridin-3-ylamine

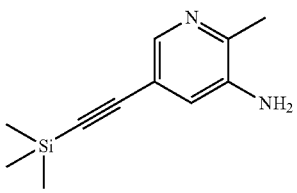

To a stirred solution of 22.0 g (118 mmol) C-3 in 500 mL diisopropylamine under argon atmosphere is added 2.2 g (12 mmol) CuI and 4.13 g (5.9 mmol) bis(triphenyl-phosphine) palladium(II) chloride. Then 48.8 mL (348 mmol) trimethylsilylacetylene are added and the mixture is heated at 100° C. over night. After conventional workup the crude product is purified by column chromatography on silica gel. Yield: 23 g (92%). ¹H NMR (CDCl₃) δ: 8.0 (s, 1H), δ 7.0 (s, 1H), 3.6 (s, 2H), 2.4 (s, 3H), 0.1 (s, 9H). TLC (silica, 50% EtOAc in PE): R_f=0.50.

D-2) 2,4-Difluoro-N-(2-methyl-5-trimethylsilanyl-ethynyl-pyridin-3-yl)-benzenesulfonamide

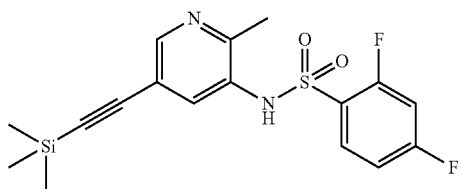 [SMILES: Cc1ncc(C#C[Si](C)(C)C)cc1NS(=O)(=O)c1ccc(F)cc1F]

To a stirred solution of 3.5 g (9.7 mmol) C-7 in 60 mL dry THF under argon atmosphere is added 56 mg (0.29 mmol) CuI, 205 mg (0.29 mmol) bis(triphenyl-phosphine)palladium (II) chloride, 255 mg (0.97 mmol) triphenylphosphine and 13.5 mL (97.4 mmol) triethylamin. Then 2.1 mL (15 mmol) trimethylsilylacetylene are added and the reaction is heated at 60° C. for three days. After cooling to RT, the solvent is removed under reduced pressure and the crude product is taken up with EtOAc and extracted twice with water. The combined organic layers are dried over MgSO₄ and the product is purified by chromatography on silica gel. Yield: 3.20 g (86%).

D-3) 5-Ethynyl-2-methyl-pyridin-3-ylamine

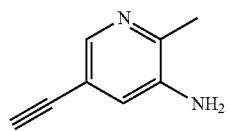

To a stirred solution of 23 g (113 mmol) D-1 in 230 mL methanol is added 31 g (225 mmol) potassium carbonate and the reaction mixture is stirred for three h at RT. The reaction mixture is filtered and the solvent is removed under reduced pressure. The crude product can be used without further purification. The Yield: 11 g (74%). ¹H NMR (CDCl₃) δ: 8.1 (s, 1H), 87.0 (s, 1H), 3.6 (s, 2H), 3.1 (s, 1H), 2.4 (s, 3H).

D-4) N-(5-Ethynyl-2-methyl-pyridin-3-yl)-methane-sulfonamide

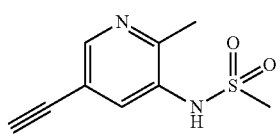

To a stirred solution of 26 g (0.197 mol) D-3 at 0° C. in 250 mL THF is added 48 mL (0.59 mol) pyridine. After 10 min 68.5 g (393.4 mmol) mesyl anhydride is added and the mixture is stirred at 0° C. for 30 min. The reaction mixture is poured in ice water and extracted with EtOAc. The organic layer is dried over MgSO₄ and the solvent is removed under reduced pressure. The obtained product is washed with ether. Yield: 20 g (48%).

D-5) N-(5-Ethynyl-2-methyl-pyridin-3-yl)-2,4-difluoro-benzenesulfonamide

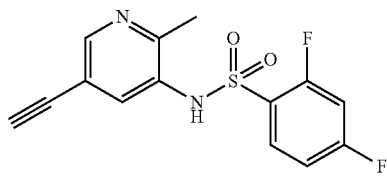 [SMILES: C#Cc1cnc(C)c(NS(=O)(=O)c2ccc(F)cc2F)c1]

A mixture of 3.20 g (8.4 mmol) D-2 and 1.81 g (8.4 mmol) potassium carbonate in 10 mL MeOH is stirred at RT for 5 h. The reaction mixture is concentrated under reduced pressure, the residue is taken up in EtOAc and washed with water, with aqueous 1 M HCl and with brine. The organic layer is dried over MgSO₄ and the product is purified by chromatography on silica gel. Yield: 1.8 g (69%).

D-6) N-(5-Ethynyl-2-methyl-pyridin-3-yl)-benzene-sulfonamide

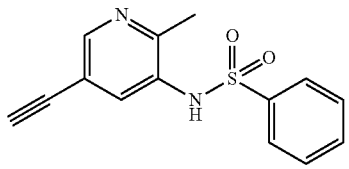 [SMILES: C#Cc1cnc(C)c(NS(=O)(=O)c2ccccc2)c1]

A mixture of 2.00 g (15.1 mmol) D-3, 4.00 mL (22.7 mmol) benzenesulfonyl chloride, 1.83 mL (22.7 mmol) pyridine and 45 mL DCM is stirred at RT over night. DCM (50 mL) is added and the mixture is extracted with 50 mL of a solution of KHSO₄ in water. During the extraction the product precipitates and is filtered off. The crude product can be used without further purification. Yield: 3.67 g (89%).

D-7) N-(5-Ethynyl-2-methyl-pyridin-3-yl)-2-fluoro-benzenesulfonamide

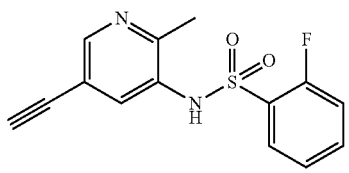 [SMILES: C#Cc1cnc(C)c(NS(=O)(=O)c2ccccc2F)c1]

A mixture of 2.00 g (15.1 mmol) D-3, 4.42 mL (22.6 mmol) 2-fluoro-benzenesulfonyl chloride, 1.83 mL (22.6 mmol) pyridine and 45 mL DCM is stirred at RT over night. DCM (50 mL) is added and the reaction mixture is extracted with 50 mL of a solution of KHSO₄ in water. During the extraction the product precipitates and is filtered off. The crude product can be used without further purification. Yield: 3.10 g (71%).

D-8) N-(5-Ethynyl-2-methyl-pyridin-3-yl)-4-fluoro-benzenesulfonamide

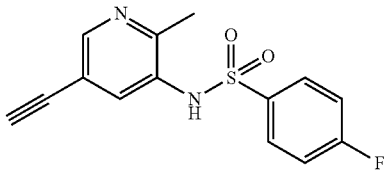 [SMILES: C#Cc1cnc(C)c(NS(=O)(=O)c2ccc(F)cc2)c1]

A mixture of 2.0 g (15.1 mmol) D-3, 4.00 mL (22.6 mmol) 4-fluoro-benzenesulfonyl chloride, 1.83 mL (22.6 mmol) pyridine and 45 mL DCM is stirred at RT over night. DCM (50 mL) is added and the reaction mixture is extracted with 50 mL of a solution of $KHSO_4$ in water. During the extraction the product precipitates and is filtered off. The crude product can be used without further purification. Yield: 2.12 g (48%).

D-9) 5-Trimethylsilanylethynyl-pyridin-3-ylamine

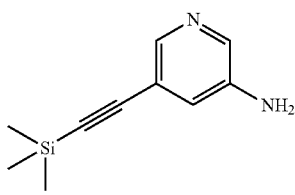

To a mixture of 7.23 g (41.8 mmol) 5-bromo-3-aminopyridine in 70 mL dry THF under argon atmosphere is added 239 mg (1.3 mmol) CuI, 880 mg (1.3 mmol) bis(triphenyl-phosphine)palladium(II) chloride, 1.1 g (4.2 mmol) triphenylphosphine and 70 mL (0.50 mol) triethylamin. Then 8.3 mL (59 mmol) trimethylsilylacetylene are added and the reaction mixture is heated at 75° C. over night. After cooling to RT, 100 mL DCM is added and the reaction mixture is extracted twice with 100 mL water. The organic layer is dried over $MgSO_4$ and the product is purified by chromatography on silica gel. Yield: 5.26 g (66%).

D-10) 5-Ethynyl-pyridin-3-ylamine

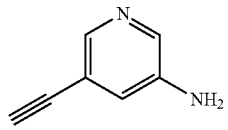

A mixture of 5.26 g (27.6 mmol) B-18 and 7.63 g (0.055 mol) potassium carbonate in 90 mL MeOH is stirred at RT for 30 min. The reaction mixture is concentrated under reduced pressure, the residue is taken up in 50 mL DCM and extracted with 50 mL water. The organic layer is dried over $MgSO_4$ and the solvent is removed under reduced pressure. The crude product can be used without further purification. Yield: 3.15 g (96%).

D-11) 2-Methoxy-5-trimethylsilanylethynyl-pyridin-3-ylamine

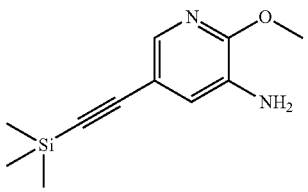

To a mixture of 1.00 g (4.93 mmol) C-5 in 15 mL dry THF under argon atmosphere is added 47 mg (0.25 mmol) CuI, 104 mg (0.13 mmol) bis(triphenylphosphine)-palladium(II) chloride and 6.83 mL (49.3 mmol) triethylamin. Then 1.74 mL (12.3 mmol) trimethylsilylacetylene are added and the reaction is heated at 80° C. over night. The reaction mixture is cooled to RT, filtered and concentrated under reduced pressure. The residue is taken up in DCM and water, acidified to pH 6 with aqueous 1N HCl and the phases are separated. The water phase is extracted twice with DCM and the combined organic phases are washed with water, dried over $MgSO_4$ and concentrated under reduced pressure. The product is purified by NP chromatography (silica gel, 2-20% MeOH containing 0.1% $NH_3$ in DCM). Yield: 0.69 g (64%).

D-12) 5-Ethynyl-2-methoxy-pyridin-3-ylamine

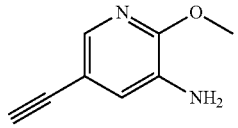

A mixture of 0.96 g (3.1 mmol) D-11 and 0.65 g (4.7 mmol) potassium carbonate in 7 mL MeOH is stirred at RT for 2 h. Next 1 mL of 4M HCl in dioxane is added and the reaction mixture is concentrated under reduced pressure. The residue is taken up in DCM and saturated aqueous $NaHCO_3$, the phases are separated and the water phase is extracted with DCM. The combined organic phases are dried over $MgSO_4$, 1 mL of a 4M HCl solution in dioxane is added and the solvent is removed under reduced pressure. Yield: 0.55 g (95%).

Preparation of Intermediates E

E-1) N-[5-(4-Chloro-6-ethyl-pyrimidin-5-ylethynyl)-2-methyl-pyridin-3-yl]-methanesulfonamide

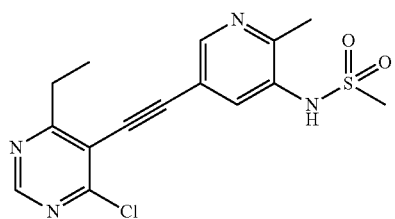 [SMILES: CCc1ncnc(Cl)c1C#Cc1cnc(C)c(NS(C)(=O)=O)c1]

To 5.00 g (18.6 mmol) A-6 in 40 mL dry THF under argon atmosphere is added 355 mg (1.8 mmol) copper(I) iodide, 2.15 g (1.8 mmol) tetrakis(triphenyl-phosphine)palladium(0) and 2.4 mL (16.7 mmol) triethylamin. Then 7.07 g (24.2 mmol) D-4 is added and the reaction is heated at 65° C. for 4 hours. The reaction mixture is cooled to RT, 50 mL water is added and the mixture is extracted with DCM. The organic layer is dried over MgSO$_4$ and concentrated under reduced pressure. The product is purified by chromatography on silica gel. Yield: 2.33 g (36%).

E-2) N-[5-(4-Chloro-6-ethyl-pyrimidin-5-ylethynyl)-2-methyl-pyridin-3-yl]-2,4-difluoro-benzenesulfonamide

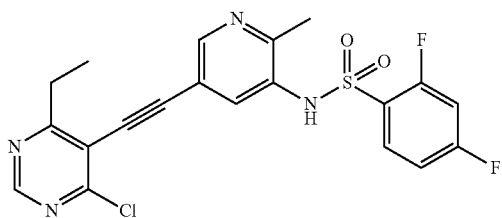 [SMILES: CCc1ncnc(Cl)c1C#Cc1cnc(C)c(NS(=O)(=O)c2ccc(F)cc2F)c1]

To 150 mg (0.56 mmol) A-6 in 2 mL dry THF under argon atmosphere is added 5.3 mg (0.028 mmol) copper iodide, 32 mg (028 μmol) tetrakistriphenylphosphinepalladium(0) and 74 μL (0.53 mmol) triethylamin. Then 189 mg (0.62 mmol) D-5 is added and the reaction is heated at 65° C. for 4 hours. The reaction mixture is cooled to RT, 50 mL water is added and the mixture is extracted with EtOAc. The organic layer is dried over MgSO$_4$ and concentrated under reduced pressure. The product is purified by chromatography on silica gel. Yield: 196 mg (78%).

E-3) 5-(4-Chloro-6-methyl-pyrimidin-5-ylethynyl)-2-methyl-pyridin-3-ylamine

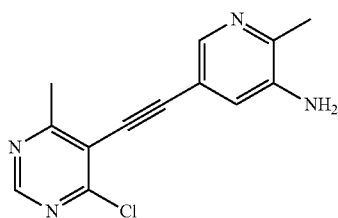 [SMILES: Cc1ncc(C#Cc2c(C)ncnc2Cl)cc1N]

Under argon atmosphere 1.14 g (0.98 mmol) tetrakis(triphenylphosphine)palladium(0) and 187 mg (0.98 mmol) copper(I) iodide are added to a mixture of 5.00 g (19.7 mmol) A-3, 3.38 g (25.5 mmol) D-3 and 14.2 mL (98.3 mmol) diisopropylamine in 100 mL DMSO and the reaction mixture is stirred overnight at 65° C. The reaction mixture is poured on 150 mL water and is extracted with DCM/MeOH. The combined organic phases are concentrated under reduced pressure and the residue is triturated with water. The crude product is purified by NP chromatography (silica gel, 2-20% MeOH containing 0.1% NH$_3$ in DCM). Yield: 3.71 g (73%).

E-4) N-[5-(4-Chloro-6-methyl-pyrimidin-5-ylethynyl)-2-methyl-pyridin-3-yl]-2,4-difluoro-benzenesulfonamide

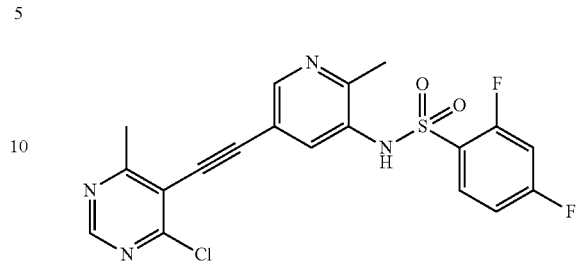

A mixture of 1.50 g (5.8 mmol) E-3, 3.08 mL (23.2 mmol) 2,4-difluoro-benzenesulfonyl chloride, 1.9 mL (24.4 mmol) pyridine and 40 mL DCM is stirred at RT over night. The reaction mixture is concentrated under reduced pressure and the residue is purified with RP-chromatograpy. Yield: 0.71 g (28%).

E-5) N-[5-(4-Chloro-6-methyl-pyrimidin-5-ylethynyl)-2-methyl-pyridin-3-yl]-benzenesulfonamide

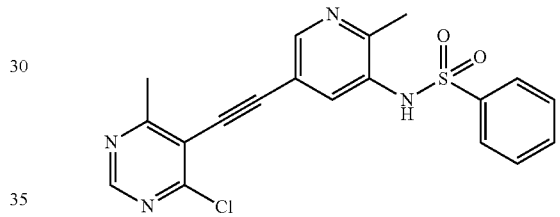

A mixture of 1.50 g (5.8 mmol) E-3, 1.48 mL (11.6 mmol) benzenesulfonyl chloride, 1.4 mL (17.4 mmol) pyridine and 50 mL DCM is stirred at RT over night. Water is added (100 mL) and the reaction mixture is extracted three times with DCM. The combined organic phases are washed with water, dried over MgSO$_4$ and concentrated under reduced pressure. The residue is purified with RP-chromatograpy (silica gel, 2-8% MeOH containing 0.1% NH$_3$ in DCM). Yield: 1.80 g (78%).

E-6) 5-(4-Methyl-6-morpholin-4-yl-pyrimidin-5-ylethynyl)-pyridin-3-ylamine

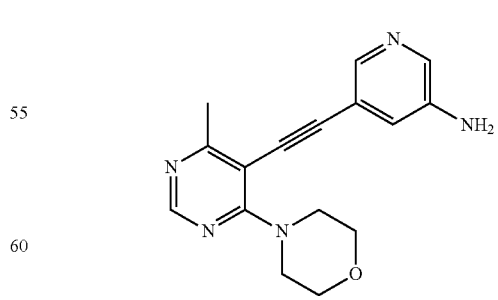

Under argon atmosphere, a mixture of 2.86 g (9.37 mmol) A-9, 1.55 g (13.1 mmol) D-10, 54 mg (0.28 mmol) copper(I) iodide, 0.25 g (0.94 mmol) triphenylphosphine, 0.20 g (0.28 mmol) bis(triphenylphosphine)palladium(II) chloride and 15.6 mL (112 mmol) triethylamine in 15 mL dry THF is stirred over night at 75° C. The reaction mixture is cooled to RT and 100 mL DCM and 100 mL water are added. The phases are separated and the organic phase is washed with water, dried over MgSO$_4$ and concentrated under reduced pressure. The residue is purified by RP chromatography (silica gel, 2-15% MeOH containing 0.1% NH$_3$ in DCM). Yield: 1.12 g (41%).

E-7) 5-(4-Ethyl-6-morpholin-4-yl-pyrimidin-5-yl-ethynyl)-2-methoxy-pyridin-3-ylamine

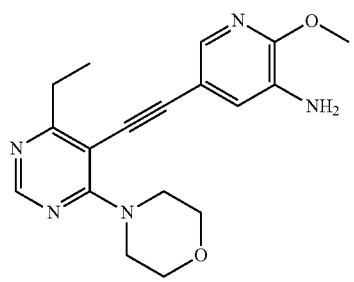 [SMILES: CCc1ncnc(N2CCOCC2)c1C#Cc1cnc(OC)c(N)c1]

Under argon atmosphere 78 mg (0.41 mmol) copper(I) iodide and 0.44 g (0.63 mmol) bis(triphenylphospine)palladium(II) dichloride are added to a mixture of 1.59 g (7.85 mmol) B-2 in 5 mL dry DMF. Subsequently 5.7 mL (41 mmol) triethyl amine and 0.90 g (4.1 mmol) C-5 are added and the reaction mixture is stirred over night at 50° C. The reaction mixture is poured on water and extracted twice with EtOAc. The combined organic phases are concentrated under reduced pressure and the product is purified chromatography. Yield: 0.15 g (11%).

E-8) N-[5-(4-Chloro-6-ethyl-pyrimidin-5-ylethynyl)-2-methyl-pyridin-3-yl]-4-fluoro-benzenesulfonamide

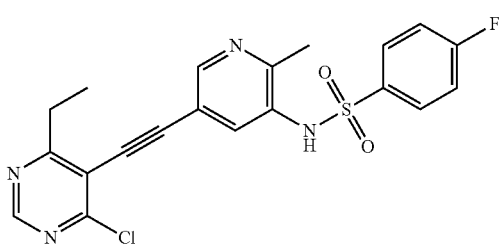 [SMILES: CCc1ncnc(Cl)c1C#Cc1cnc(C)c(NS(=O)(=O)c2ccc(F)cc2)c1]

Under argon atmosphere 0.34 g (0.48 mmol) bis(triphenylphosphin)palladium(II) chloride, 92 mg (0.48 mmol) copper(I) iodide and 6.7 mL (48 mmol) triethylamine are added to a mixture of 1.30 g (4.84 mmol) A-6 in ca. 10 mL DMF. Subsequently a mixture of 2.11 g (7.26 mmol) D-8 in ca. 5 mL DMF is added and the reaction mixture is stirred overnight at 65° C. Water is added and the reaction mixture is extracted with DCM. The combined organic phases are concentrated under reduced pressure and the residue is purified by NP chromatography. Yield: 0.88 g (42%).

E-9) 2-Methoxy-5-(4-methyl-6-morpholin-4-yl-pyrimidin-5-ylethynyl)-pyridin-3-ylamine

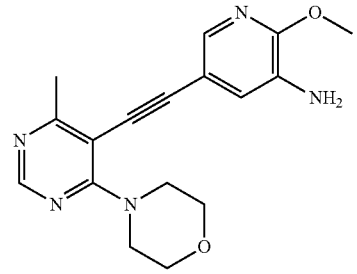 [SMILES: COc1ncc(C#Cc2c(C)ncnc2N2CCOCC2)cc1N]

Under Argon atmosphere 0.28 g (0.39 mmol) bis(triphenylphosphin)palladium(II) chloride, 75 mg (0.39 mmol) copper(I) iodide and 5.5 mL (39 mmol) triethylamine are added to a mixture of 1.04 g (5.12 mmol) B-4 in 5 mL DMF. Subsequently 0.80 g (3.9 mmol) C-5 is added and the reaction mixture is stirred overnight at 50° C. Water is added, the reaction mixture is neutralized with 2N aqueous NaOH and extracted twice with EtOAc. The combined organic phases are washed with water, dried over MgSO$_4$ and concentrated under reduced pressure. The residue is purified by RP chromatography (C18, 15-85% acetonitrile in water containing 0.1% formic acid). Yield: 0.59 g (content ca. 50%, 23%).

E-10) N-[5-(2-Amino-4-chloro-6-ethyl-pyrimidin-5-ylethynyl)-2-methyl-pyridin-3-yl]-methanesulfonamide

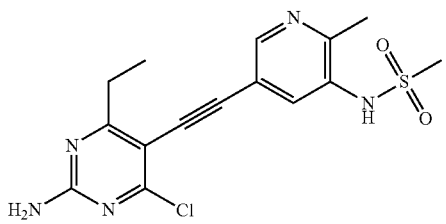 [SMILES: CCc1nc(N)nc(Cl)c1C#Cc1cnc(C)c(NS(C)(=O)=O)c1]

Under argon atmosphere 3.8 mL (26 mmol) diisopropylamine is added to a mixture of 0.43 g (0.31 mmol) tetrakis(triphenylphosphin)palladium(0), 71 mg (0.31 mmol) copper(I) iodide, 1.50 g (5.29 mmol) A-8 and 1.45 g (6.90 mmol) D-4 in 30 mL DMSO and the reaction mixture is stirred overnight at 65° C. Water is added and the reaction mixture is extracted with DCM/MeOH. The combined organic phases are concentrated under reduced pressure and the crude product is triturated with water and dried in vacuo at 40° C. Yield: 1.80 g (93%).

E-11) 2-Methyl-5-(4-methyl-6-morpholin-4-yl-pyrimidin-5-ylethynyl)-pyridin-3-ylamine

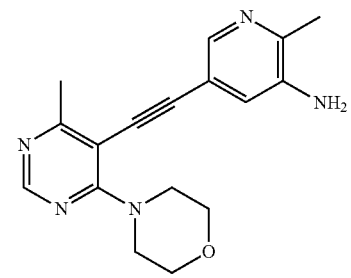 [SMILES: Cc1ncc(C#Cc2c(C)ncnc2N2CCOCC2)cc1N]

To 1.50 g (5.80 mmol) E-3 in 20 mL dioxane and 2.5 mL NMP is added 0.61 mL (7.0 mmol) morpholine and 3.0 mL (17 mmol) diisopropylethylamine and the reaction mixture is stirred over night at 80° C. The reaction mixture is cooled to RT and concentrated under reduced pressure. The residue is taken up in water and extracted with DCM. The combined organic phases are washed with water, dried over MgSO$_4$ and concentrated under reduced pressure. The crude product is purified by NP chromatography (silica gel, 2-20% MeOH containing 0.1% NH$_3$ in DCM). Yield: 1.53 g (85%).

Preparation of Final Compounds I

I-1) N-[2-Methoxy-5-(4-methyl-6-morpholin-4-yl-pyrimidin-5-ylethynyl)-pyridin-3-yl]-benzene-sulfonamide

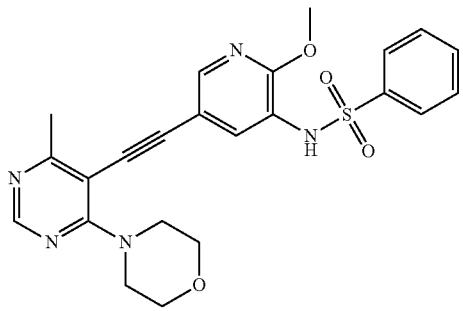 [SMILES: COc1ncc(C#Cc2c(C)ncnc2N2CCOCC2)cc1NS(=O)(=O)c1ccccc1]

A mixture of 200 mg (0.31 mmol) E-9, 77 μL (0.61 mmol) benzenesulfonyl chloride, 78 μL (0.97 mmol) pyridine and 5 mL DCM is stirred at RT over night. Water (5 mL) is added and the reaction mixture is extracted twice with 5 mL EtOAc. The organic layer is dried over MgSO$_4$ and the crude product is purified with RP chromatography (C18, 15-85% acetonitrile in water containing 0.1% formic acid). Yield: 21 mg (15%). HPLC-MS: M+H=466; tR=1.20 min.

I-2) 2-Fluoro-N-[2-methyl-5-(4-methyl-6-morpholin-4-yl-pyrimidin-5-ylethynyl)-pyridin-3-yl]-benzenesulfonamide

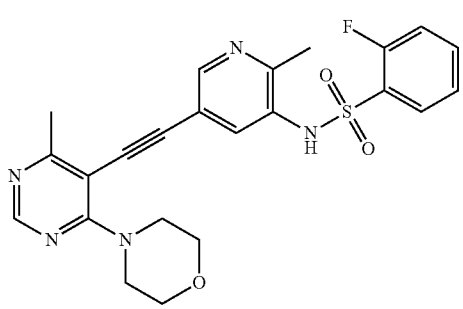 [SMILES: Cc1ncc(C#Cc2c(C)ncnc2N2CCOCC2)cc1NS(=O)(=O)c1ccccc1F]

A mixture of 100 mg (0.32 mmol) E-11, 90 μL (0.65 mmol) 2-fluorobenzenesulfonyl chloride, 78 μL (0.97 mmol) pyridine and 5 mL DCM is stirred at RT over night. Water (2 mL) is added and the reaction mixture is extracted twice with 4 mL DCM. The combined organic phases are concentrated under reduced pressure and the crude product purified with RP chromatography (C18, 25-85% acetonitrile in water containing 0.1% formic acid). Yield: 58 mg (39%). HPLC-MS: M+H=468; tR=1.08 min.

I-3) Propane-1-sulfonic acid [2-methyl-5-(4-methyl-6-morpholin-4-yl-pyrimidin-5-ylethynyl)-pyridin-3-yl]-amide

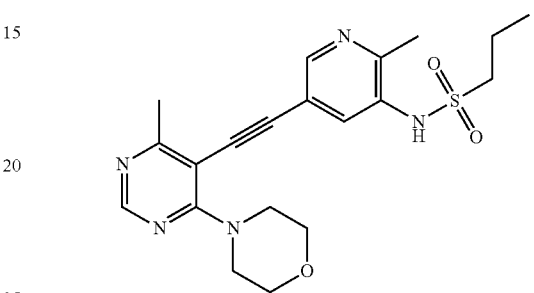

A mixture of 80 mg (0.26 mmol) E-11, 74 mg (0.52 mmol) 1-propanesulfonyl chloride, 63 μL (0.78 mmol) pyridine and 3 mL DCM is stirred at RT over night. Water (2 mL) is added and the reaction mixture is extracted twice with 4 mL DCM. The combined organic phases are concentrated under reduced pressure and the crude product purified with RP chromatography (C18, 20-80% acetonitrile in water containing 0.1% formic acid). Yield: 16 mg (15%). HPLC-MS: M+H=416; tR=0 min.

I-4) 3-Methoxy-N-[2-methyl-5-(4-methyl-6-morpholin-4-yl-pyrimidin-5-ylethynyl)-pyridin-3-yl]-benzenesulfonamide

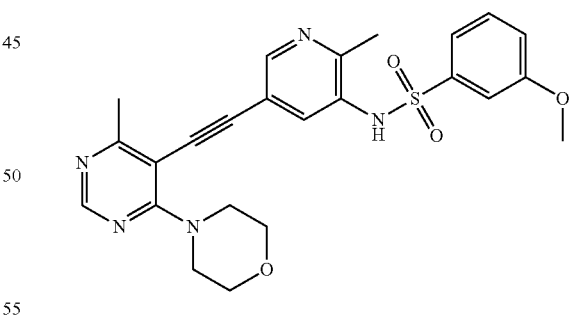

A mixture of 80 mg (0.26 mmol) E-11, 107 mg (0.52 mmol) 3-methoxybenzenesulfonyl chloride, 63 μL (0.78 mmol) pyridine and 3 mL DCM is stirred at RT over night. Water (2 mL) is added and the reaction mixture is extracted twice with 4 mL DCM. The combined organic phases are concentrated under reduced pressure and the crude product purified with RP chromatography (C18, 20-80% acetonitrile in water containing 0.1% formic acid). Yield: 59 mg (47%). HPLC-MS: M+H=480; tR=0 min.

I-5) 2-Chloro-N-[2-methyl-5-(4-methyl-6-morpholin-4-yl-pyrimidin-5-ylethynyl)-pyridin-3-yl]-benzenesulfonamide

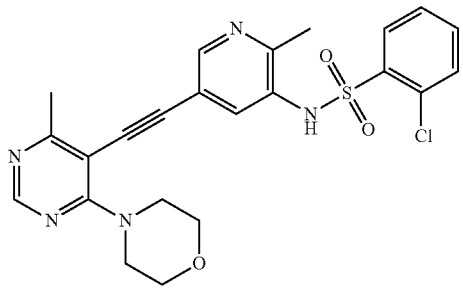

A mixture of 80 mg (0.26 mmol) E-11, 109 mg (0.52 mmol) 2-chlorobenzenesulfonyl chloride, 63 μL (0.78 mmol) pyridine and 3 mL DCM is stirred at RT over night. Water (2 mL) is added and the reaction mixture is extracted twice with 4 mL DCM. The combined organic phases are concentrated under reduced pressure and the crude product purified with RP chromatography (C18, 20-80% acetonitrile in water containing 0.1% formic acid). Yield: 31 mg (25%). HPLC-MS: M+H=484; tR=0 min.

I-6) 3-Fluoro-N-[2-methyl-5-(4-methyl-6-morpholin-4-yl-pyrimidin-5-ylethynyl)-pyridin-3-yl]-benzenesulfonamide

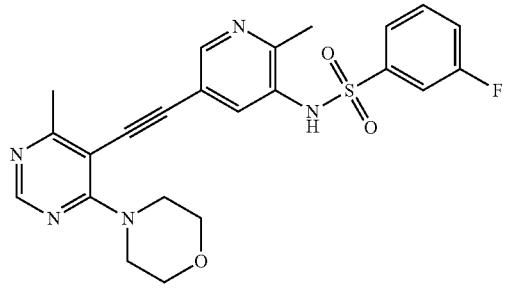 [SMILES: Cc1ncc(C#Cc2c(C)ncnc2N2CCOCC2)cc1NS(=O)(=O)c1cccc(F)c1]

A mixture of 80 mg (0.269 mmol) E-11, 101 mg (0.52 mmol) 3-fluorobenzenesulfonyl chloride, 63 μL (0.78 mmol) pyridine and 3 mL DCM is stirred at RT over night. Water (2 mL) is added and the reaction mixture is extracted twice with 4 mL DCM. The combined organic phases are concentrated under reduced pressure and the crude product purified with RP chromatography (C18, 20-80% acetonitrile in water containing 0.1% formic acid). Yield: 39 mg (33%). HPLC-MS: M+H=468; tR=0 min.

I-7) 2,6-Difluoro-N-[2-methyl-5-(4-methyl-6-morpholin-4-yl-pyrimidin-5-ylethynyl)-pyridin-3-yl]-benzenesulfonamide

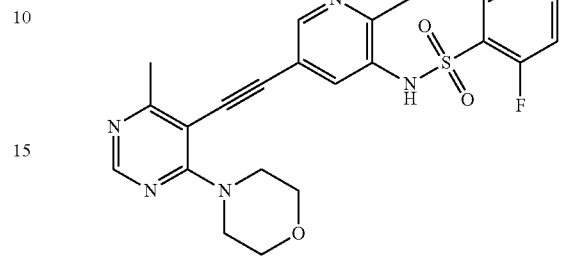

A mixture of 80 mg (0.26 mmol) E-11, 110 mg (0.52 mmol) 2,6-difluorobenzenesulfonyl chloride, 63 μL (0.78 mmol) pyridine and 3 mL DCM is stirred at RT over night. Water (2 mL) is added and the reaction mixture is extracted twice with 4 mL DCM. The combined organic phases are concentrated under reduced pressure and the crude product purified with RP chromatography (C18, 20-80% acetonitrile in water containing 0.1% formic acid). Yield: 14 mg (11%). HPLC-MS: M+H=486; tR=0 min.

I-8) 2-Bromo-N-[2-methyl-5-(4-methyl-6-morpholin-4-yl-pyrimidin-5-ylethynyl)-pyridin-3-yl]-benzenesulfonamide

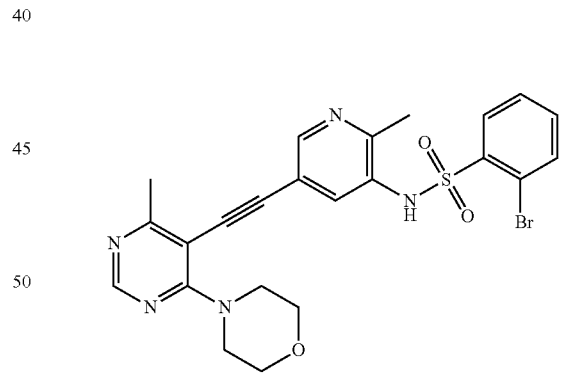

A mixture of 80 mg (0.26 mmol) E-11, 132 mg (0.52 mmol) 2-bromobenzenesulfonyl chloride, 63 μL (0.78 mmol) pyridine and 3 mL DCM is stirred at RT over night. Water (2 mL) is added and the reaction mixture is extracted twice with 4 mL DCM. The combined organic phases are concentrated under reduced pressure and the crude product purified with RP chromatography (C18, 20-80% acetonitrile in water containing 0.1% formic acid). Yield: 35 mg (26%). HPLC-MS: M+H=528/530; tR=0 min.

I-9) 1-Methyl-1H-imidazole-4-sulfonic acid [2-methyl-5-(4-methyl-6-morpholin-4-yl-pyrimidin-5-ylethynyl)-pyridin-3-yl]-amide

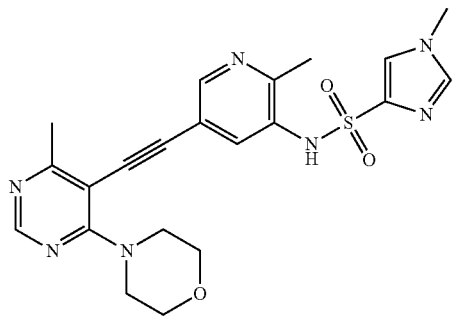 [SMILES: Cc1ncc(C#Cc2c(C)ncnc2N2CCOCC2)cc1NS(=O)(=O)c1cn(C)cn1]

A mixture of 80 mg (0.26 mmol) E-11, 94 mg (0.52 mmol) 1-methylimidazole-4-sulfonyl chloride, 63 μL (0.78 mmol) pyridine and 3 mL DCM is stirred at RT over night. Water (2 mL) is added and the reaction mixture is extracted twice with 4 mL DCM. The combined organic phases are concentrated under reduced pressure and the crude product purified with RP chromatography (C18, 20-80% acetonitrile in water containing 0.1% formic acid). Yield: 35 mg (30%). HPLC-MS: M+H=454; tR=0 min.

I-10) Thiophene-2-sulfonic acid [2-methyl-5-(4-methyl-6-morpholin-4-yl-pyrimidin-5-ylethynyl)-pyridin-3-yl]-amide

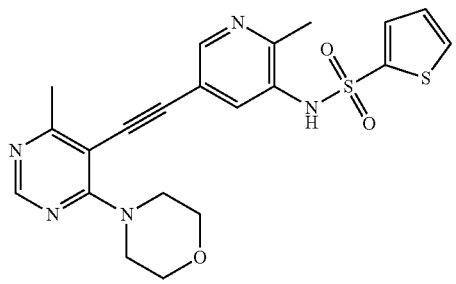

A mixture of 80 mg (0.26 mmol) E-11, 95 mg (0.52 mmol) 2-thiophenesulfonyl chloride, 63 μL (0.78 mmol) pyridine and 3 mL DCM is stirred at RT over night. Water (2 mL) is added and the reaction mixture is extracted twice with 4 mL DCM. The combined organic phases are concentrated under reduced pressure and the crude product purified with RP chromatography (C18, 20-80% acetonitrile in water containing 0.1% formic acid). Yield: 37 mg (32%). HPLC-MS: M+H=456; tR=0 min.

I-11) 2-Methyl-N-[2-methyl-5-(4-methyl-6-morpholin-4-yl-pyrimidin-5-ylethynyl)-pyridin-3-yl]-benzenesulfonamide

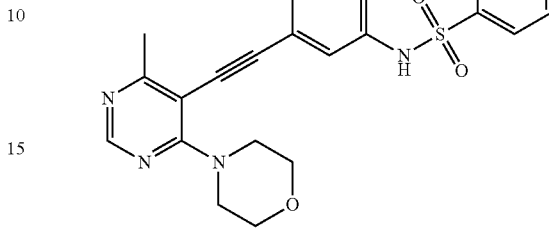

A mixture of 80 mg (0.26 mmol) E-11, 99 mg (0.52 mmol) o-toluenesulfonyl chloride, 63 μL (0.78 mmol) pyridine and 3 mL DCM is stirred at RT over night. Water (2 mL) is added and the reaction mixture is extracted twice with 4 mL DCM. The combined organic phases are concentrated under reduced pressure and the crude product purified with RP chromatography (C18, 20-80% acetonitrile in water containing 0.1% formic acid). Yield: 33 mg (27%). HPLC-MS: M+H=464; tR=0.97 min.

I-12) 2-Methoxy-ethanesulfonic acid [2-methyl-5-(4-methyl-6-morpholin-4-yl-pyrimidin-5-ylethynyl)-pyridin-3-yl]-amide

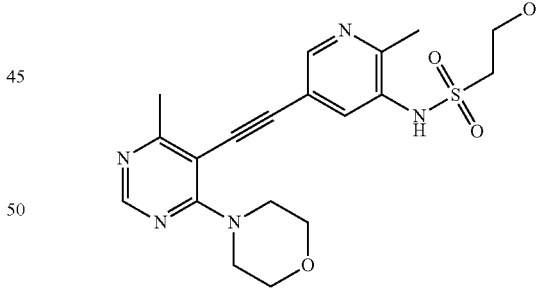

A mixture of 80 mg (0.26 mmol) E-11, 82 mg (0.52 mmol) 2-methoxyethane-1-sulfonyl chloride, 63 μL (0.78 mmol) pyridine and 3 mL DCM is stirred at RT over night. Water (2 mL) is added and the reaction mixture is extracted twice with 4 mL DCM. The combined organic phases are concentrated under reduced pressure and the crude product purified with RP chromatography (C18, 20-80% acetonitrile in water containing 0.1% formic acid). Yield: 19 mg (17%). HPLC-MS: M+H=432; tR=0 min.

I-13) N-[2-Methyl-5-(4-methyl-6-morpholin-4-yl-pyrimidin-5-ylethynyl)-pyridin-3-yl]-2-trifluoromethyl-benzenesulfonamide

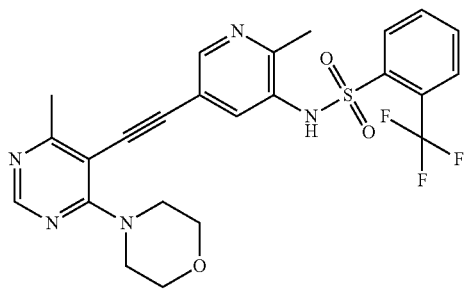 [SMILES: Cc1ncc(C#Cc2c(C)ncnc2N2CCOCC2)cc1NS(=O)(=O)c1ccccc1C(F)(F)F]

A mixture of 80 mg (0.26 mmol) E-11, 127 mg (0.52 mmol) 2-(trifluoromethyl)-benzenesulfonyl chloride, 63 μL (0.78 mmol) pyridine and 3 mL DCM is stirred at RT over night. Water (2 mL) is added and the reaction mixture is extracted twice with 4 mL DCM. The combined organic phases are concentrated under reduced pressure and the crude product purified with RP chromatography (C18, 20-80% acetonitrile in water containing 0.1% formic acid). Yield: 22 mg (16%). HPLC-MS: M+H=518; tR=0 min.

I-14) 2,4-Difluoro-N-[2-methyl-5-(4-methyl-6-piperidin-1-yl-pyrimidin-5-ylethynyl)-pyridin-3-yl]-benzenesulfonamide

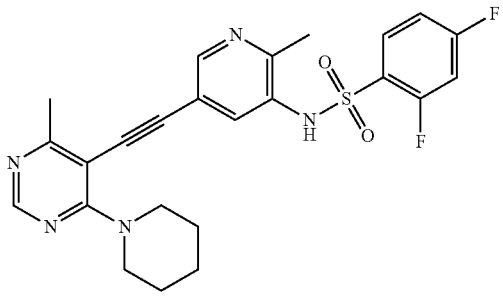 [SMILES: Cc1ncc(C#Cc2c(C)ncnc2N2CCCCC2)cc1NS(=O)(=O)c1ccc(F)cc1F]

A mixture of 63 mg (0.15 mmol) E-4, 17 μL (0.17 mmol) piperidine, 28 μL (0.174 mmol) diisopropylethylamine, 500 μL NMP and 1 mL dioxane is stirred at 80° C. for 1 h under microwave irradiation. The reaction mixture is purified with RP chromatography (C18, 20-90% acetonitrile in water containing 0.1% formic acid). Yield: 7 mg (10%). HPLC-MS M+H=484; tR=1.21 min.

I-15) 2,4-Difluoro-N-{5-[4-(isopropyl-methyl-amino)-6-methyl-pyrimidin-5-ylethynyl]-2-methyl-pyridin-3-yl}-benzenesulfonamide

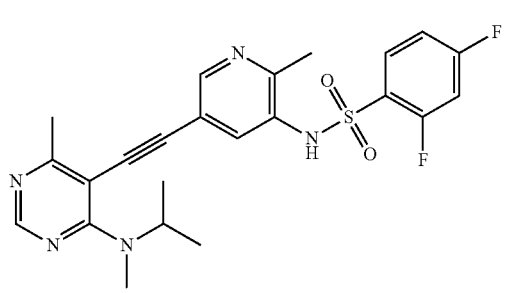 [SMILES: Cc1ncc(C#Cc2c(C)ncnc2N(C)C(C)C)cc1NS(=O)(=O)c1ccc(F)cc1F]

A mixture of 63 mg (0.15 mmol) E-4, 15 μL (0.15 mmol) isopropyl-methyl-amine, 500-μL NMP and 1 mL dioxane is stirred at 90° C. for 1 h. The reaction mixture is purified with RP chromatography (C18, 10-80% acetonitrile in water containing 0.1% formic acid). Yield: 5 mg (7%). HPLC-MS M+H=472; tR=1.21 min.

I-16) 2,4-Difluoro-N-(2-methyl-5-{4-methyl-6-[methyl-(tetrahydro-pyran-4-yl)-amino]-pyrimidin-5-ylethynyl}-pyridin-3-yl)-benzenesulfonamide

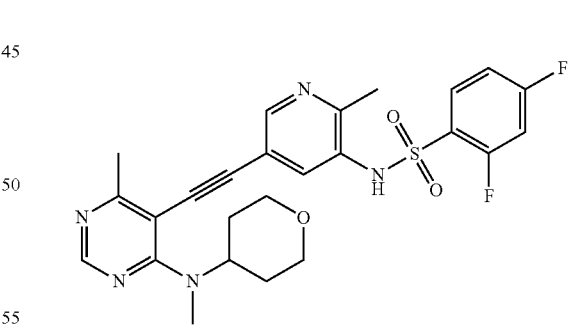

A mixture of 63 mg (0.15 mmol) E-4, 17 mg (0.15 mmol) methyl-(tetrahydro-pyran-4-yl)-amine, 500 μL NMP and 1 mL dioxane is stirred at 90° C. for 1 h. The reaction mixture is purified with RP chromatography (C18, 10-80% acetonitrile in water containing 0.1% formic acid). Yield: 12 mg (16%). HPLC-MS: M+H=514; tR=0 min.

I-17) N-{5-[4-(4-Acetyl-piperazin-1-yl)-6-methyl-pyrimidin-5-ylethynyl]-2-methyl-pyridin-3-yl}-2,4-difluoro-benzenesulfonamide

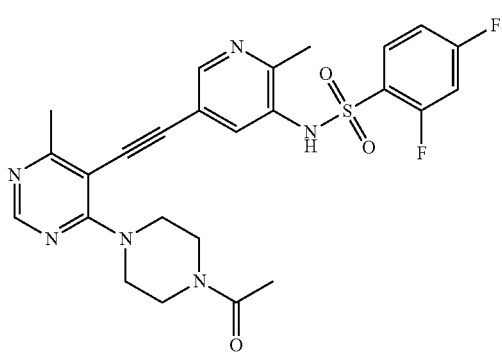 [SMILES: CC(=O)N1CCN(c2ncnc(C)c2C#Cc2cnc(C)c(NS(=O)(=O)c3ccc(F)cc3F)c2)CC1]

A mixture of 63 mg (0.15 mmol) E-4, 19 mg (0.15 mmol) 1-piperazin-1-yl-ethanone, 500 μL NMP and 1 mL dioxane is stirred at 90° C. for 1 h. The reaction mixture is purified with RP chromatography (C18, 10-80% acetonitrile in water containing 0.1% formic acid). Yield: 25 mg (33%). HPLC-MS: M+H=527; tR=1.08 min.

I-18) 2,4-Difluoro-N-{2-methyl-5-[4-methyl-6-(4-methyl-piperazin-1-yl)-pyrimidin-5-ylethynyl]-pyridin-3-yl}-benzenesulfonamide

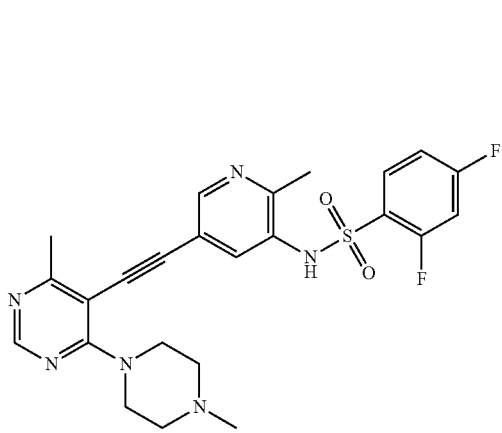 [SMILES: Cc1ncc(C#Cc2c(C)ncnc2N2CCN(C)CC2)cc1NS(=O)(=O)c1ccc(F)cc1F]

A mixture of 63 mg (0.15 mmol) E-4, 16 L (0.15 mmol) 1-methyl-piperazine, 500 μL NMP and 1 mL dioxane is stirred at 90° C. for 1 h. The reaction mixture is purified with RP chromatography (C18, 20-90% acetonitrile in water containing 0.1% formic acid). Yield: 17 mg (24%). HPLC-MS: M+H=499; tR=1.11 min.

I-19) N-[5-(4-Methyl-6-morpholin-4-yl-pyrimidin-5-ylethynyl)-pyridin-3-yl]-benzenesulfonamide

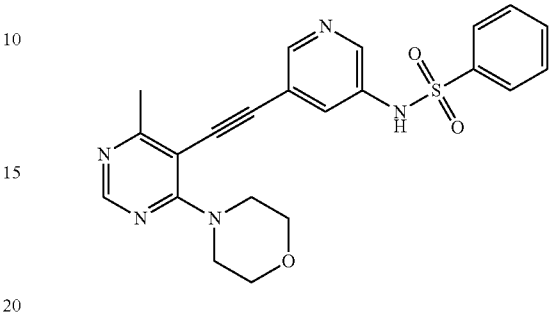

A mixture of 200 mg (0.68 mmol) E-6, 239 mg (1.4 mmol) benzenesulfonyl chloride, 164 μL (2.03 mmol) pyridine and 10 mL DCM is stirred at RT over night. After completion of the reaction the reaction mass was filtered to afford the crude compound. The crude product can be used without further purification. Yield: 0.22 g (75%). HPLC-MS: M+H=436; tR=1.01 min.

I-20) 2,4-Difluoro-N-[5-(4-methyl-6-morpholin-4-yl-pyrimidin-5-ylethynyl)-pyridin-3-yl]-benzenesulfonamide

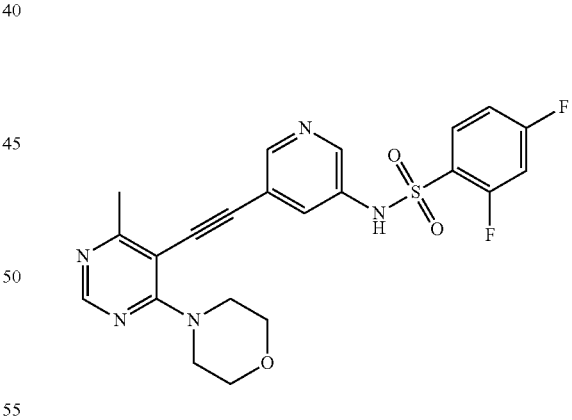

A mixture of 200 mg (0.68 mmol) E-6, 182 μL (1.4 mmol) 2,4-difluorobenzenesulfonyl chloride, 164 μL (2.03 mmol) pyridine and 10 mL DCM is stirred at RT over night. After completion of the reaction the reaction mass was filtered to afford the crude compound. The crude product is purified with NP chromatography (silica gel, 0-15% MeOH containing 0.1% NH₃ in DCM). Yield: 0.11 g (33%). HPLC-MS: M+H=472; tR=1.12 min.

I-21) Thiophene-2-sulfonic acid [5-(4-methyl-6-morpholin-4-yl-pyrimidin-5-ylethynyl)-pyridin-3-yl]-amide

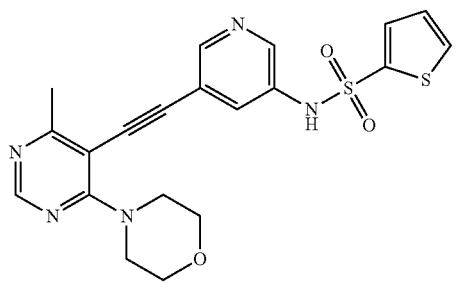 [SMILES: Cc1ncnc(N2CCOCC2)c1C#Cc1cncc(NS(=O)(=O)c2cccs2)c1]

A mixture of 160 mg (0.54 mmol) E-6, 198 mg (1.1 mmol) 2-thiophensulfonylchlorid, 131 μL (1.6 mmol) pyridine and 4 mL DCM is stirred at RT over night. After completion of the reaction the reaction mass was filtered to afford the crude compound. The crude product is purified with NP chromatography (silica gel, 0-15% MeOH containing 0.1% $NH_3$ in DCM). Yield: 0.11 g (47%). HPLC-MS: M+H=442; tR=0.97 min.

I-22) Pyridine-3-sulfonic acid [5-(4-methyl-6-morpholin-4-yl-pyrimidin-5-ylethynyl)-pyridin-3-yl]-amide

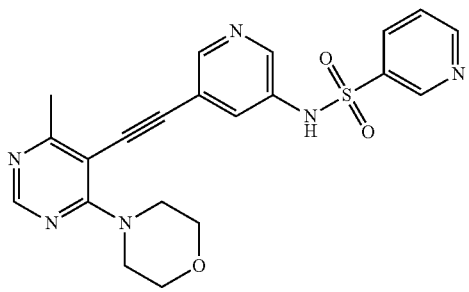 [SMILES: Cc1ncnc(N2CCOCC2)c1C#Cc1cncc(NS(=O)(=O)c2cccnc2)c1]

A mixture of 160 mg (0.54) E-6, 192 mg (1.1 mmol) pyridin-3-sulfonylchlorid, 131 μL (1.6 mmol) pyridine and 4 mL DCM is stirred at RT over night. After completion of the reaction the reaction mass was filtered to afford the crude compound. The crude product is purified with NP chromatography (silica gel, 0-15% MeOH containing 0.1% $NH_3$ in DCM). Yield: 0.48 g (content 50%, 100%). HPLC-MS: M+H=437; tR=0.87 min.

I-23) 1-Methyl-1H-pyrazole-4-sulfonic acid [5-(4-methyl-6-morpholin-4-yl-pyrimidin-5-ylethynyl)-pyridin-3-yl]-amide

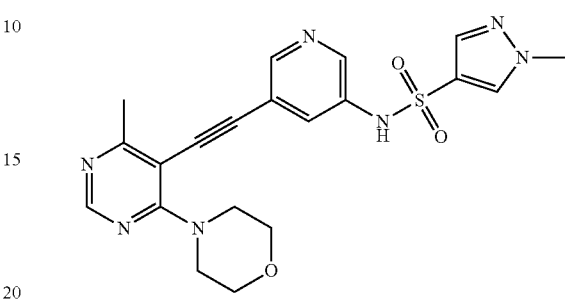

A mixture of 160 mg (0.54 mmol) E-6, 196 μL (1.1 mmol) 1-methyl-1H-pyrazol-4-sulfonylchlorid, 131 μL (1.6 mmol) pyridine and 10 mL DCM is stirred at RT over night. After completion of the reaction the reaction mass was filtered to afford the crude compound. Yield: 0.16 g (66%). HPLC-MS: M+H=440; tR=0.80 min.

I-24) N-[5-(4-Methyl-6-morpholin-4-yl-pyrimidin-5-ylethynyl)-pyridin-3-yl]-methanesulfonamide

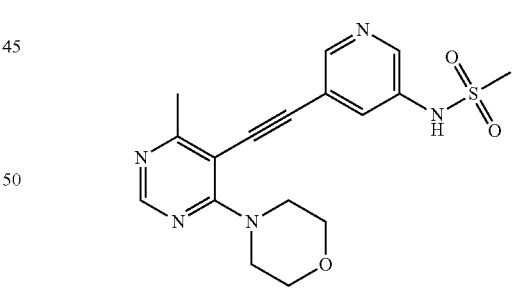

To a mixture of 0.20 g (0.68 mmol) E-6 in 10 mL DCM is added 0.16 mL (2.0 mmol) pyridine and the reaction mixture is stirred for 5 min. at RT. Methanesulfonyl chloride 0.10 mL (1.4 mmol) is added and the reaction mixture is stirred over night at RT. The precipitated product is filtered off and dried in vacuo at 40° C. Yield: 0.15 g (59%). HPLC-MS: M+H=374; tR=0.80 min.

I-25) N-[5-(4-Ethyl-6-morpholin-4-yl-pyrimidin-5-ylethynyl)-2-methoxy-pyridin-3-yl]-2,4-difluoro-benzenesulfonamide

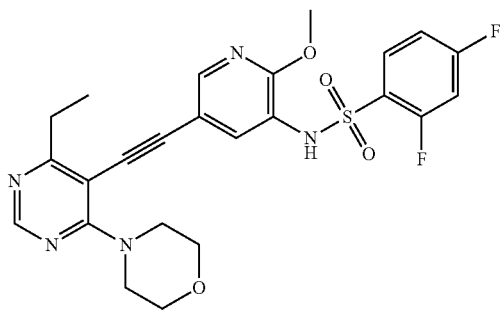 [SMILES: CCc1ncnc(N2CCOCC2)c1C#Cc1cnc(OC)c(NS(=O)(=O)c2ccc(F)cc2F)c1]

A mixture of 75 mg (0.22 mmol) E-7, 59 µL (0.44 mmol) 2,4-difluoro-benzenesulfonyl chloride and 56 µL (0.71 mmol) pyridine in 3 mL DCM is stirred over night at RT. The reaction mixture is concentrated under reduced pressure and the residue is purified by RP chromatography (C18, 20-90% acetonitrile in water containing 0.1% formic acid). Yield: 52 mg (46%). HPLC-MS: M+H=516; tR=1.17 min.

I-26) N-[5-(4-Ethyl-6-morpholin-4-yl-pyrimidin-5-ylethynyl)-2-methoxy-pyridin-3-yl]-benzenesulfonamide

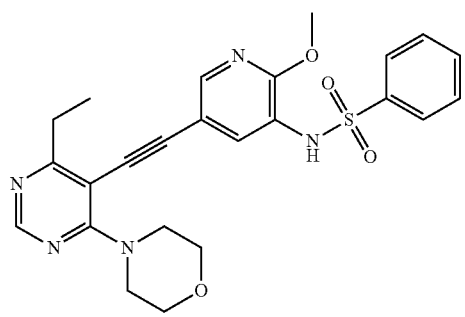 [SMILES: CCc1ncnc(N2CCOCC2)c1C#Cc1cnc(OC)c(NS(=O)(=O)c2ccccc2)c1]

A mixture of 75 mg (0.22 mmol) E-7, 55 µL (0.44 mmol) benzenesulfonyl chloride and 56 µL (0.71 mmol) pyridine in 3 mL DCM is stirred over night at RT. The reaction mixture is concentrated under reduced pressure and the residue is purified by RP chromatography (C18, 20-90% acetonitrile in water containing 0.1% formic acid). Yield: 64 mg (60%). HPLC-MS: M+H=480; tR=1.13 min.

I-27) N-[5-(4-Dimethylamino-6-ethyl-pyrimidin-5-ylethynyl)-2-methyl-pyridin-3-yl]-4-fluoro-benzenesulfonamide

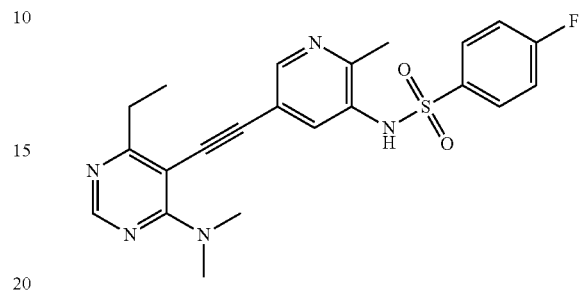

To 80 mg (0.19 mmol) E-8 in 1 mL dioxane is added 0.46 mL (0.93 mmol) of a 2.0 M solution of dimethylamine in THF and the reaction mixture is stirred for 3 h at 80° C. A 1/1 acetonitrile/water mixture is added and the reaction mixture is purified by RP chromatography (C18). Yield: 25 mg (31%). HPLC-MS: M+H=440; tR=1.12 min.

I-28) N-{5-[4-(4-Cyclopropyl-piperazin-1-yl)-6-ethyl-pyrimidin-5-ylethynyl]-2-methyl-pyridin-3-yl}-4-fluoro-benzenesulfonamide

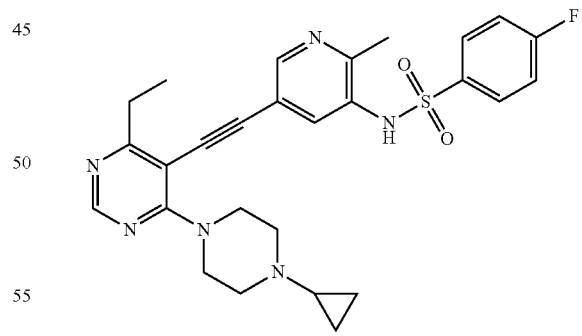

To 80 mg (0.19 mmol) E-8 in 1 mL dioxane is added 0.12 g (0.93 mmol) 1-cyclopropyl-piperazine and 26 L (0.19 mmol) triethylamine and the reaction mixture is stirred for 3 h at 80° C. A 1/1 acetonitrile/water mixture is added and the reaction mixture is purified by RP chromatography (C18). Yield: 49 mg (51%). HPLC-MS: M+H=521; tR=1.26 min.

I-29) 2,4-Difluoro-N-[2-methoxy-5-(4-methyl-6-morpholin-4-yl-pyrimidin-5-ylethynyl)-pyridin-3-yl]-benzenesulfonamide

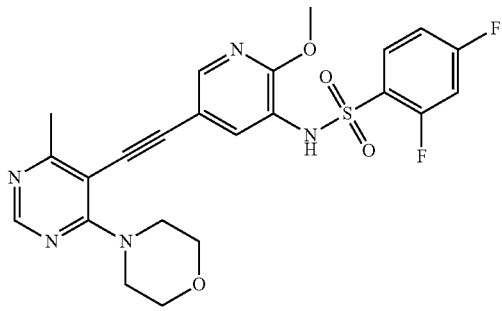 [SMILES: COc1ncc(C#Cc2c(C)ncnc2N2CCOCC2)cc1NS(=O)(=O)c1ccc(F)cc1F]

A mixture of 200 mg (content ca. 50%, 0.31 mmol) E-9, 82 µL (0.61 mmol) 2,4-difluorobenzenesulfonyl chloride, 78 µL (0.97 mmol) pyridine and 5 mL DCM is stirred at RT over night. Water (5 mL) is added and the reaction mixture is extracted three times with 8 mL EtOAc. The combined organic phases are concentrated under reduced pressure and the crude product is purified with RP-HPLC (C18, 25-85% acetonitrile in water containing 0.1% formic acid). Yield: 28 mg (18%). HPLC-MS: M+H=502; tR=1.21 min.

I-30) 4-Fluoro-N-[2-methyl-5-(4-methyl-6-morpholin-4-yl-pyrimidin-5-ylethynyl)-pyridin-3-yl]-benzenesulfonamide

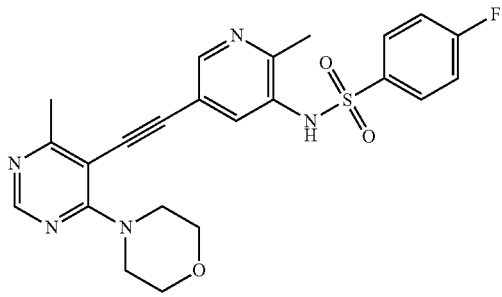 [SMILES: Cc1ncc(C#Cc2c(C)ncnc2N2CCOCC2)cc1NS(=O)(=O)c1ccc(F)cc1]

A mixture of 100 mg (0.32 mmol) E-11, 126 mg (0.65 mmol) 4-fluorobenzenesulfonyl chloride, 78 µL (0.97 mmol) pyridine and 5 mL DCM is stirred at RT over night. Water (2 mL) is added and the reaction mixture is extracted three times with 4 mL DCM. The combined organic phases are concentrated under reduced pressure and the crude product is purified with RP-HPLC(C18, 25-85% acetonitrile in water containing 0.1% formic acid). Yield: 100 mg (67%). HPLC-MS: M+H=468; tR=1.12 min.

I-31) 3,5-Difluoro-N-[2-methyl-5-(4-methyl-6-morpholin-4-yl-pyrimidin-5-ylethynyl)-pyridin-3-yl]-benzenesulfonamide

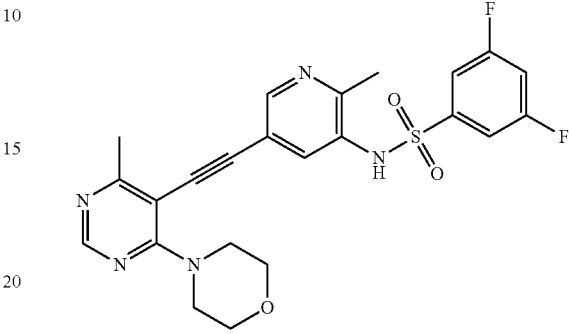

A mixture of 100 mg (0.32 mmol) E-11, 137 mg (0.65 mmol) 3,5-difluorobenzenesulfonyl chloride, 78 L (0.97 mmol) pyridine and 5 mL DCM is stirred at RT over night. Water (2 mL) is added and the reaction mixture is extracted three times with 4 mL DCM. The combined organic phases are concentrated under reduced pressure and the crude product is purified with RP-HPLC (C18, 25-85% acetonitrile in water containing 0.1% formic acid). Yield: 99 mg (64%). HPLC-MS: M+H=486; tR=1.18 min.

I-32) N-[5-(4-Dimethylamino-6-ethyl-pyrimidin-5-ylethynyl)-2-methyl-pyridin-3-yl]-methanesulfonamide

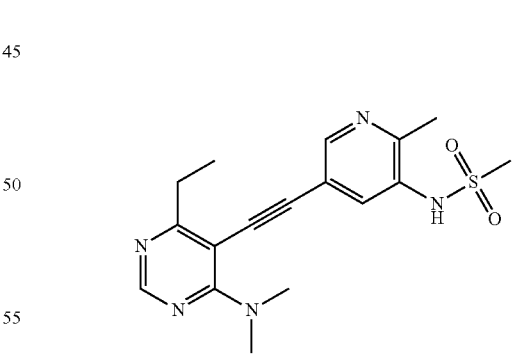

To 75 mg (0.21 mmol) E-1 in 1 mL dioxane is added 1.6 mL (3.2 mmol) of a 2.0 M solution of dimethylamine in THF and the reaction mixture is stirred for 3 h at 80° C. A 1/1 acetonitrile/water mixture is added and the reaction mixture is purified by RP chromatography (C18). Yield: 33 mg (43%). HPLC-MS: M+H=360; tR=0.89 min.

I-33) N-[5-(4-Ethyl-6-methylamino-pyrimidin-5-ylethynyl)-2-methyl-pyridin-3-yl]-methanesulfonamide

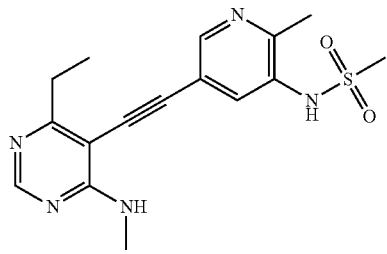 [SMILES: CCc1ncnc(NC)c1C#Cc1cnc(C)c(NS(C)(=O)=O)c1]

To 75 mg (0.21 mmol) E-1 in 1 mL dioxane is added 2.14 mL (4.28 mmol) of a 2.0 M solution of methylamine in THF and the reaction mixture is stirred for 3 h at 80° C. A 1/1 acetonitrile/water mixture is added and the reaction mixture is purified by RP chromatography (C18). Yield: 6 mg (8%). HPLC-MS: M+H=346; tR=0.77 min.

I-34) N-{5-[2-Amino-4-ethyl-6-(4-methoxy-piperidin-1-yl)-pyrimidin-5-ylethynyl]-2-methyl-pyridin-3-yl}-methanesulfonamide

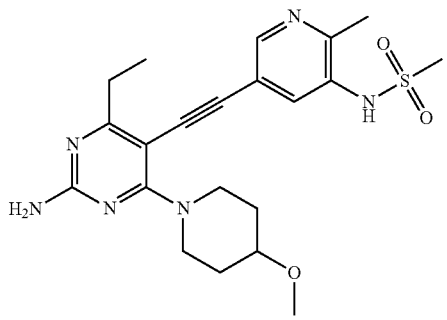 [SMILES: CCc1nc(N)nc(N2CCC(OC)CC2)c1C#Cc1cnc(C)c(NS(C)(=O)=O)c1]

To 80 mg (0.22 mmol) E-10 in 2 mL dioxane and 1 mL DMF is added 28 mg (0.24 mmol) 4-methoxypiperidine and 45 µL (0.26 mmol) diisopropylethylamin and the reaction mixture is stirred for 1 h at 130° C. in a microwave oven. The reaction mixture is purified by RP chromatography (C18, 5-70% acetonitrile in water containing 0.1% formic acid). Yield: 29 mg (30%). HPLC-MS: M+H=445, tR=0.95 min.

I-35) N-{5-[2-Amino-4-ethyl-6-(4-hydroxy-piperidin-1-yl)-pyrimidin-5-ylethynyl]-2-methyl-pyridin-3-yl}-methanesulfonamide

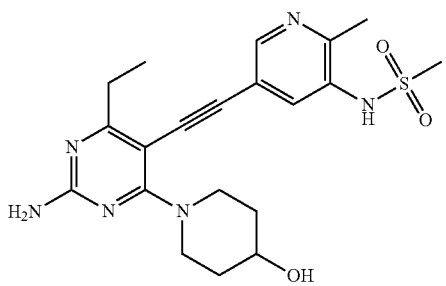 [SMILES: CCc1nc(N)nc(N2CCC(O)CC2)c1C#Cc1cnc(C)c(NS(C)(=O)=O)c1]

To 80 mg (0.22 mmol) E-10 in 2 mL dioxane and 1 mL DMF is added 24 mg (0.24 mmol) 4-hydroxypiperidine and 45 µL (0.26 mmol) diisopropylethylamin and the reaction mixture is stirred for 1 h at 130° C. in a microwave oven. The reaction mixture is purified by RP chromatography (C18, 5-70% acetonitrile in water containing 0.1% formic acid). Yield: 23 mg (24%). HPLC-MS: M+H=431; tR=0.81 min.

I-36) N-[5-(2-Amino-4-ethyl-6-piperidin-1-yl-pyrimidin-5-ylethynyl)-2-methyl-pyridin-3-yl]-methanesulfonamide

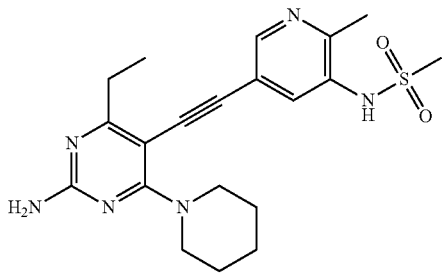 [SMILES: CCc1nc(N)nc(N2CCCCC2)c1C#Cc1cnc(C)c(NS(C)(=O)=O)c1]

To 80 mg (0.22 mmol) E-10 in 2 mL dioxane and 1 mL DMF is added 20 mg (0.24 mmol) piperidine and 45 µL (0.26 mmol) diisopropylethylamin and the reaction mixture is stirred for 1 h at 130° C. in a microwave oven. The reaction mixture is purified by RP chromatography (C18, 5-80% acetonitrile in water containing 0.1% formic acid). Yield: 19 mg (21%). HPLC-MS: M+H=415; tR=1.01 min.

I-37) N-[2-Methyl-5-(4-methyl-6-morpholin-4-yl-pyrimidin-5-ylethynyl)-pyridin-3-yl]-methanesulfonamide

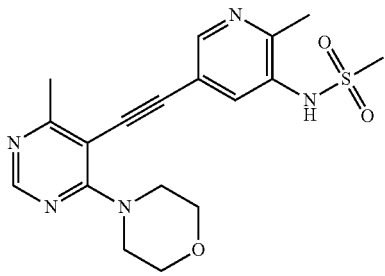 [SMILES: Cc1ncc(C#Cc2c(C)ncnc2N2CCOCC2)cc1NS(C)(=O)=O]

To 100 mg (0.32 mmol) E-11 in 5 mL DCM is added 49 µL (0.65 mmol) methanesulfonyl chloride and 78 µL (0.97 mmol) pyridine and the reaction mixture is stirred over night at RT. Water (5 mL) is added and the reaction mixture is extracted twice with 5 mL EtOAc. The combined organic phases are dried over MgSO$_4$ and concentrated under reduced pressure. The crude product is purified by RP chromatography (C18, 5-70% acetonitrile in water containing 0.1% formic acid). Yield: 44 mg (35%). HPLC-MS: M+H=388; tR=0.91 min.

I-38) Propane-2-sulfonic acid [2-methyl-5-(4-methyl-6-morpholin-4-yl-pyrimidin-5-ylethynyl)-pyridin-3-yl]-amide

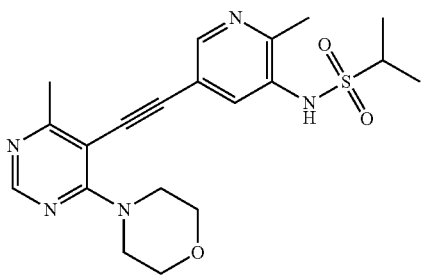 [SMILES: Cc1ncc(C#Cc2c(C)ncnc2N2CCOCC2)cc1NS(=O)(=O)C(C)C]

To 100 mg (0.32 mmol) E-11 in 5 mL DCM is added 71 µL (0.65 mmol) isopropylsulfonyl chloride and 78 µL (0.97 mmol) pyridine and the reaction mixture is stirred over night at RT. Water (5 mL) is added and the reaction mixture is extracted twice with 5 mL EtOAc. The combined organic phases are dried over MgSO$_4$ and concentrated under reduced pressure. The crude product is purified by RP chromatography (C18, 5-70% acetonitrile in water containing 0.1% formic acid). Yield: 8 mg (6%). HPLC-MS: M+H=416; tR=1.08 min.

I-39) Cyclohexanesulfonic acid [2-methyl-5-(4-methyl-6-morpholin-4-yl-pyrimidin-5-ylethynyl)-pyridin-3-yl]-amide

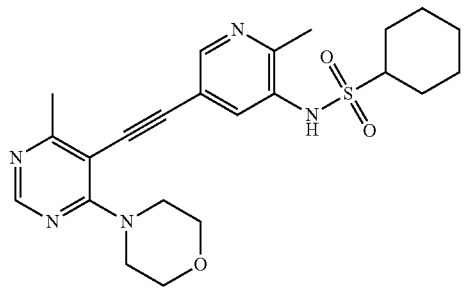 [SMILES: Cc1ncc(C#Cc2c(C)ncnc2N2CCOCC2)cc1NS(=O)(=O)C1CCCCC1]

To 100 mg (0.32 mmol) E-11 in 5 mL DCM is added 118 µL (0.65 mmol) cyclohexanesulfonyl chloride and 78 µL (0.97 mmol) pyridine and the reaction mixture is stirred over night at RT. Water (5 mL) is added and the reaction mixture is extracted twice with 5 mL EtOAc. The combined organic phases are dried over MgSO$_4$ and concentrated under reduced pressure. The crude product is purified by RP chromatography (C18, 5-70% acetonitrile in water containing 0.1% formic acid). Yield: 24 mg (16%). HPLC-MS: M+H=456; tR=1.28 min.

I-40) N-[2-Methyl-5-(4-methyl-6-morpholin-4-yl-pyrimidin-5-ylethynyl)-pyridin-3-yl]-benzenesulfonamide

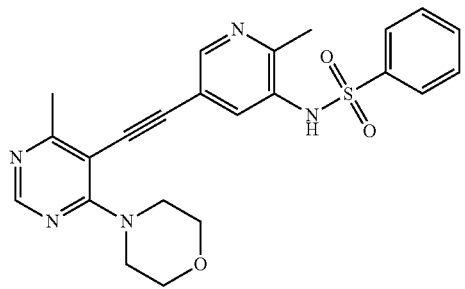 [SMILES: Cc1ncc(C#Cc2c(C)ncnc2N2CCOCC2)cc1NS(=O)(=O)c1ccccc1]

To 100 mg (0.32 mmol) E-11 in 5 mL DCM is added 81 µL (0.65 mmol) benzenesulfonyl chloride and 78 µL (0.97 mmol) pyridine and the reaction mixture is stirred over night at RT. Water (2 mL) is added and the reaction mixture is extracted three times with 4 mL DCM. The combined organic phases are dried over MgSO$_4$ and concentrated under reduced pressure. The crude product is purified by RP chromatography (C18, 25-85% MeOH in water containing 2.5% NH$_3$OH and 2.5% NH$_4$HCO$_3$). Yield: 96 mg (66%). HPLC-MS: M+H=450; tR=1.05 min.

I-41) 2,4-Difluoro-N-[2-methyl-5-(4-methyl-6-morpholin-4-yl-pyrimidin-5-ylethynyl)-pyridin-3-yl]-benzenesulfonamide I-43) N-{5-[2-Amino-4-ethyl-6-(4-hydroxy-4-methyl-piperidin-1-yl)-pyrimidin-5-ylethynyl]-2-methyl-pyridin-3-yl}-methanesulfonamide

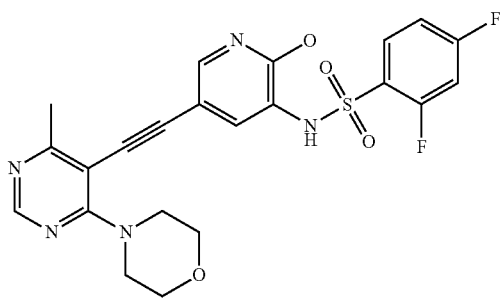 [SMILES: Cc1ncnc(N2CCOCC2)c1C#Cc1cnc(O)c(NS(=O)(=O)c2ccc(F)cc2F)c1]

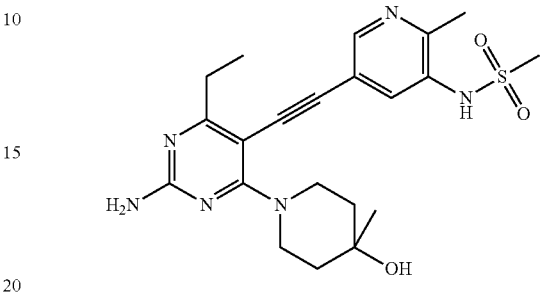

To 100 mg (0.32 mmol) E-11 in 5 mL DCM is added 86 μL (0.65 mmol) 2,4-difluorobenzenesulfonyl chloride and 78 μL (0.97 mmol) pyridine and the reaction mixture is stirred over night at RT. Water (2 mL) is added and the reaction mixture is extracted three times with 4 mL DCM. The combined organic phases are dried over MgSO$_4$ and concentrated under reduced pressure. The crude product is purified by RP chromatography (C18, 25-85% MeOH in water containing 2.5% NH$_3$OH and 2.5% NH$_4$HCO$_3$). Yield: 35 mg (22%). HPLC-MS: M+H=486; tR=1.14 min.

To 80 mg (0.22 mmol) E-10 in 2 mL dioxane and 1 mL DMF is added 28 mg (0.24 mmol) 4-methyl-piperidin-4-ol and 45 μL (0.26 mmol) diisopropylethylamin and the reaction mixture is stirred for 1 h at 130° C. in a microwave oven. The reaction mixture is purified by RP chromatography (C18, 5-70% acetonitrile in water containing 0.1% formic acid). Yield: 45 mg (46%). HPLC-MS: M+H=445; tR=0.91 min.

I-42) N-{5-[4-Ethyl-6-(4-hydroxy-4-methyl-piperidin-1-yl)-pyrimidin-5-ylethynyl]-2-methyl-pyridin-3-yl}-methanesulfonamide I-44) N-[5-(4-Ethyl-6-piperidin-1-yl-pyrimidin-5-ylethynyl)-2-methyl-pyridin-3-yl]-methanesulfonamide

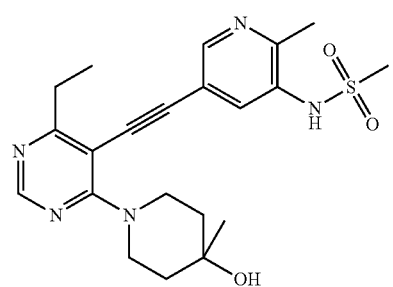 [SMILES: CCc1ncnc(N2CCC(C)(O)CC2)c1C#Cc1cnc(C)c(NS(C)(=O)=O)c1]

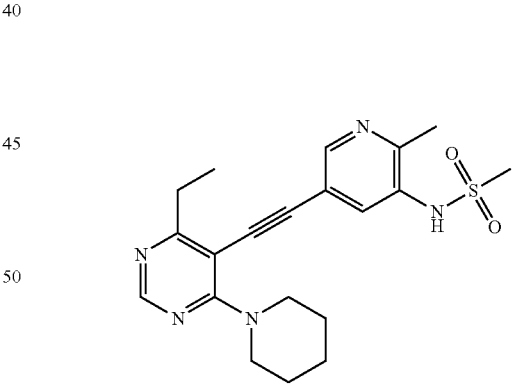

To 80 mg (0.23 mmol) E-1 in 2 mL dioxane and 1 mL DMF is added 29 mg (0.25 mmol) 4-methyl-piperidin-4-ol and 47 μL (0.27 mmol) diisopropylethylamin and the reaction mixture is stirred for 1 h at 130° C. in a microwave oven. The reaction mixture is purified by RP—(C18, 5-70% acetonitrile in water containing 0.1% formic acid) followed by NP chromatography (NH$_2$ capped silica, 1-20% MeOH in DCM). Yield: 2 mg (2%). HPLC-MS: M+H=430; tR=0.96 min.

To 80 mg (0.23 mmol) E-1 in 2 mL dioxane and 1 mL DMF is added 21 mg (0.25 mmol) piperidine and 47 μL (0.27 mmol) diisopropylethylamin and the reaction mixture is stirred for 1 h at 130° C. in a microwave oven. The reaction mixture is purified by RP—(C18, 5-70% acetonitrile in water containing 0.1% formic acid) followed by NP chromatography (NH$_2$ capped silica, 1-20% MeOH in DCM). Yield: 3 mg (3%). HPLC-MS: M+H=400; tR=1.16 min.

I-45) N-{5-[4-Ethyl-6-(4-methoxy-piperidin-1-yl)-pyrimidin-5-ylethynyl]-2-methyl-pyridin-3-yl}-methanesulfonamide I-46) N-{5-[4-Ethyl-6-(4-hydroxy-piperidin-1-yl)-pyrimidin-5-ylethynyl]-2-methyl-pyridin-3-yl}-methanesulfonamide

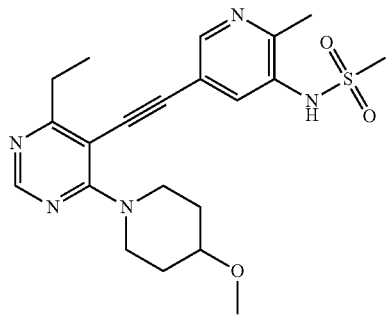 [SMILES: CCc1ncnc(N2CCC(OC)CC2)c1C#Cc1cnc(C)c(NS(C)(=O)=O)c1]

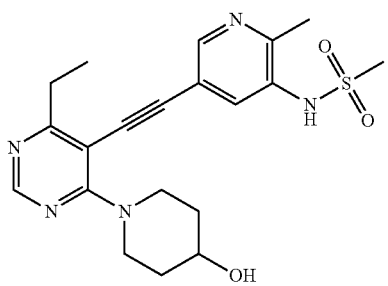 [SMILES: CCc1ncnc(N2CCC(O)CC2)c1C#Cc1cnc(C)c(NS(C)(=O)=O)c1]

To 80 mg (0.23 mmol) E-1 in 2 mL dioxane and 1 mL DMF is added 29 mg (0.25 mmol) 4-methoxypiperidine and 47 μL (0.27 mmol) diisopropylethylamin and the reaction mixture is stirred for 1 h at 130° C. in a microwave oven. The reaction mixture is purified by RP—(C18, 5-80% acetonitrile in water containing 0.1% formic acid) followed by NP chromatography (NH$_2$ capped silica, 1-20% MeOH in DCM). Yield: 3 mg (3%). HPLC-MS: M+H=430; tR=1.01 min.

To 80 mg (0.23 mmol) E-1 in 2 mL dioxane and 1 mL DMF is added 25 mg (0.25 mmol) 4-hydroxypiperidine and 47 μL (0.27 mmol) diisopropylethylamin and the reaction mixture is stirred for 1 h at 130° C. in a microwave oven. The reaction mixture is purified by RP—(C18, 5-70% acetonitrile in water containing 2.5% NH$_3$OH and 2.5% NH$_4$HCO$_3$) followed by NP chromatography. Yield: 2 mg (2%). HPLC-MS: M+H=414; tR=0.87 min.

TABLE 1

Examples 1-47 to 1-80

Compounds 1-47 to 1-80 found in the table below may be prepared starting from the suitable intermediates described above and following similar procedures as for compounds I-1 to 1-46.

| Ex. # | Molecular Structure | Name | HPLC-MS |
|---|---|---|---|
| 1-47 | 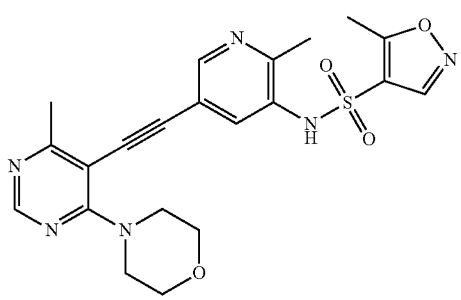 [SMILES: Cc1ncc(C#Cc2c(C)ncnc2N2CCOCC2)cc1NS(=O)(=O)c1cnoc1C] | 5-Methyl-isoxazole-4-sulfonic acid [2-methyl-5-(4-methyl-6-morpholin-4-yl-pyrimidin-5-ylethynyl)-pyridin-3-yl]-amide | M + H = 455; tR = 0.67 |
| 1-48 | | 2,5-Dimethyl-thiophene-3-sulfonic acid [2-methyl-5-(4-methyl-6-morpholin-4-yl-pyrimidin-5-ylethynyl)-pyridin-3-yl]-amide | M + H = 484; tR = 1.21 |

TABLE 1-continued

Examples 1-47 to 1-80
Compounds 1-47 to 1-80 found in the table below may be prepared starting from the suitable intermediates described above and following similar procedures as for compounds I-1 to 1-46.

| Ex. # | Molecular Structure | Name | HPLC-MS |
|---|---|---|---|
| I-49 | 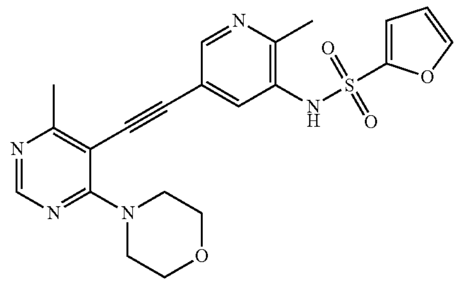 [SMILES: Cc1ncc(C#Cc2c(C)ncnc2N2CCOCC2)cc1NS(=O)(=O)c1ccco1] | Furan-2-sulfonic acid [2-methyl-5-(4-methyl-6-morpholin-4-yl-pyrimidin-5-ylethynyl)-pyridin-3-yl]-amide | M + H = 440; tR = 0.93; |
| I-50 | 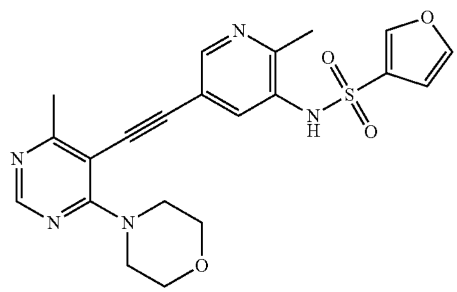 [SMILES: Cc1ncc(C#Cc2c(C)ncnc2N2CCOCC2)cc1NS(=O)(=O)c1ccoc1] | Furan-3-sulfonic acid [2-methyl-5-(4-methyl-6-morpholin-4-yl-pyrimidin-5-ylethynyl)-pyridin-3-yl]-amide | M + H = 440; tR = 1.01 |
| I-51 | 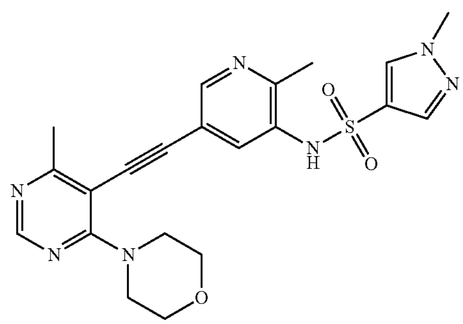 | 1-Methyl-1H-pyrazole-4-sulfonic acid [2-methyl-5-(4-methyl-6-morpholin-4-yl-pyrimidin-5-ylethynyl)-pyridin-3-yl]-amide | M + H = 554; tR = 1.04 |
| I-52 | 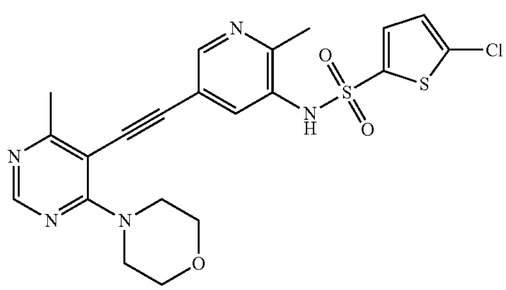 [SMILES: Cc1ncc(C#Cc2c(C)ncnc2N2CCOCC2)cc1NS(=O)(=O)c1ccc(Cl)s1] | 5-Chloro-thiophene-2-sulfonic acid [2-methyl-5-(4-methyl-6-morpholin-4-yl-pyrimidin-5-ylethynyl)-pyridin-3-yl]-amide | M + H = 490; tR = 1.22 |
| I-53 | 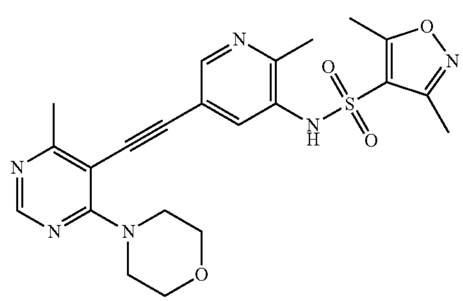 [SMILES: Cc1ncc(C#Cc2c(C)ncnc2N2CCOCC2)cc1NS(=O)(=O)c1c(C)noc1C] | 3,5-Dimethyl-isoxazole-4-sulfonic acid [2-methyl-5-(4-methyl-6-morpholin-4-yl-pyrimidin-5-ylethynyl)-pyridin-3-yl]-amide | M + H = 469; tR = 1.05 |

TABLE 1-continued

Examples 1-47 to 1-80

Compounds 1-47 to 1-80 found in the table below may be prepared starting from the suitable intermediates described above and following similar procedures as for compounds I-1 to 1-46.

| Ex. # | Molecular Structure | Name | HPLC-MS |
|---|---|---|---|
| I-54 | 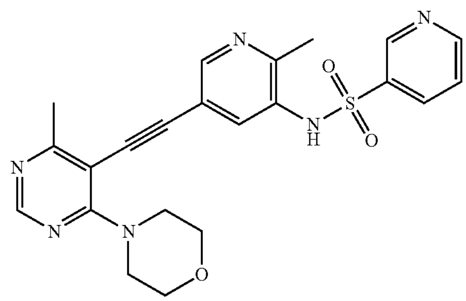 [SMILES: Cc1ncc(C#Cc2c(C)ncnc2N2CCOCC2)cc1NS(=O)(=O)c1cccnc1] | Pyridine-3-sulfonic acid [2-methyl-5-(4-methyl-6-morpholin-4-yl-pyrimidin-5-ylethynyl)-pyridin-3-yl]-amide | M + H = 451; tR = 1.01 |
| I-55 | 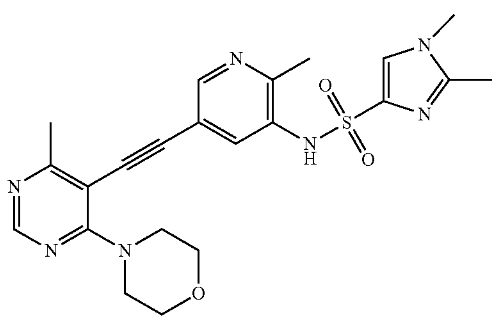 [SMILES: Cc1ncc(C#Cc2c(C)ncnc2N2CCOCC2)cc1NS(=O)(=O)c1cn(C)c(C)n1] | 1,2-Dimethyl-1H-imidazole-4-sulfonic acid [2-methyl-5-(4-methyl-6-morpholin-4-yl-pyrimidin-5-ylethynyl)-pyridin-3-yl]-amide | M + H = 468; tR = 0.92 |
| I-56 | 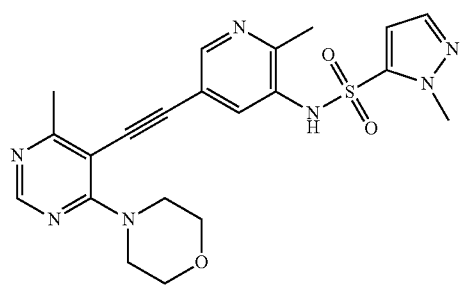 [SMILES: Cc1ncc(C#Cc2c(C)ncnc2N2CCOCC2)cc1NS(=O)(=O)c1ccnn1C] | 2-Methyl-2H-pyrazole-3-sulfonic acid [2-methyl-5-(4-methyl-6-morpholin-4-yl-pyrimidin-5-ylethynyl)-pyridin-3-yl]-amide | M + H = 454; tR = 0.97 |
| I-57 | 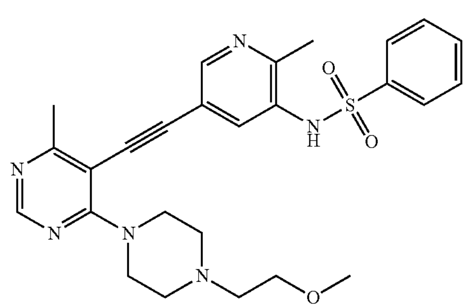 [SMILES: COCCN1CCN(c2ncnc(C)c2C#Cc2cnc(C)c(NS(=O)(=O)c3ccccc3)c2)CC1] | N-(5-{4-[4-(2-Methoxy-ethyl)-piperazin-1-yl]-6-methyl-pyrimidin-5-ylethynyl}-2-methyl-pyridin-3-yl)-benzenesulfonamide | M + H = 507; tR = 1.09 |

TABLE 1-continued

Examples 1-47 to 1-80

Compounds 1-47 to 1-80 found in the table below may be prepared starting from the suitable intermediates described above and following similar procedures as for compounds I-1 to 1-46.

| Ex. # | Molecular Structure | Name | HPLC-MS |
|---|---|---|---|
| I-58 | 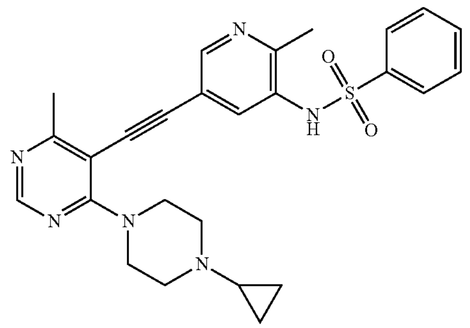 [SMILES: Cc1ncc(C#Cc2c(C)ncnc2N2CCN(C3CC3)CC2)cc1NS(=O)(=O)c1ccccc1] | N-{5-[4-(4-Cyclopropyl-piperazin-1-yl)-6-methyl-pyrimidin-5-ylethynyl]-2-methyl-pyridin-3-yl}-benzenesulfonamide | M + H = 489; tR = 1.16 |
| I-59 | 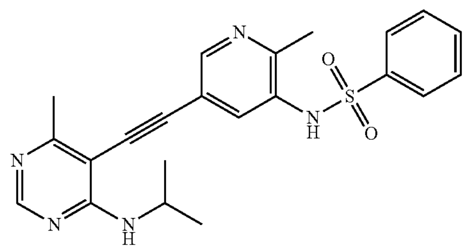 [SMILES: Cc1ncc(C#Cc2c(C)ncnc2NC(C)C)cc1NS(=O)(=O)c1ccccc1] | N-[5-(4-Isopropylamino-6-methyl-pyrimidin-5-ylethynyl)-2-methyl-pyridin-3-yl]-benzenesulfonamide | M + H = 422; tR = 1.10 |
| I-60 | 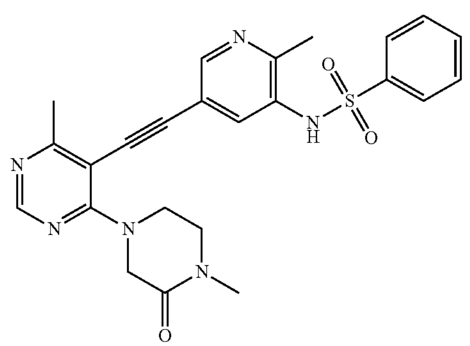 [SMILES: Cc1ncc(C#Cc2c(C)ncnc2N2CCN(C)C(=O)C2)cc1NS(=O)(=O)c1ccccc1] | N-{2-Methyl-5-[4-methyl-6-(4-methyl-3-oxo-piperazin-1-yl)-pyrimidin-5-ylethynyl]-pyridin-3-yl}-benzenesulfonamide | M + H = 477; tR = 0.98 |
| I-61 | 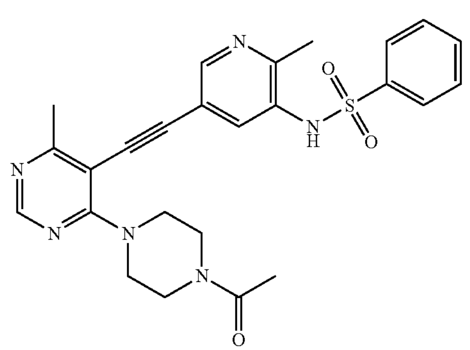 [SMILES: CC(=O)N1CCN(c2ncnc(C)c2C#Cc2cnc(C)c(NS(=O)(=O)c3ccccc3)c2)CC1] | N-{5-[4-(4-Acetyl-piperazin-1-yl)-6-methyl-pyrimidin-5-ylethynyl]-2-methyl-pyridin-3-yl}-benzenesulfonamide | M + H = 491; tR = 1.00 |

TABLE 1-continued

Examples 1-47 to 1-80
Compounds 1-47 to 1-80 found in the table below may be prepared starting from the suitable intermediates described above and following similar procedures as for compounds I-1 to 1-46.

| Ex. # | Molecular Structure | Name | HPLC-MS |
|---|---|---|---|
| I-62 | 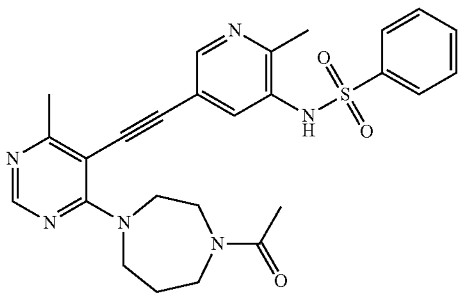 [SMILES: CC(=O)N1CCCN(c2ncnc(C)c2C#Cc2cnc(C)c(NS(=O)(=O)c3ccccc3)c2)CC1] | N-{5-[4-(4-Acetyl-[1,4]diazepan-1-yl)-6-methyl-pyrimidin-5-ylethynyl]-2-methyl-pyridin-3-yl}-benzenesulfonamide | M + H = 505; tR = 1.01 |
| I-63 | 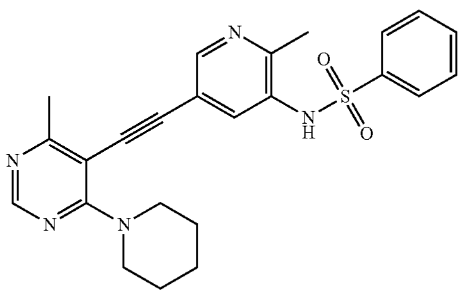 [SMILES: Cc1ncc(C#Cc2c(C)ncnc2N2CCCCC2)cc1NS(=O)(=O)c1ccccc1] | N-[2-Methyl-5-(4-methyl-6-piperidin-1-yl-pyrimidin-5-ylethynyl)-pyridin-3-yl]-benzenesulfonamide | M + H = 448; tR = 1.18 |
| I-64 | 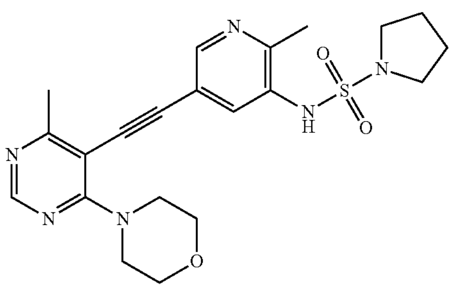 [SMILES: Cc1ncc(C#Cc2c(C)ncnc2N2CCOCC2)cc1NS(=O)(=O)N1CCCC1] | Pyrrolidine-1-sulfonic acid [2-methyl-5-(4-methyl-6-morpholin-4-yl-pyrimidin-5-ylethynyl)-pyridin-3-yl]-amide | M + H = 443; tR = 1.08 |
| I-65 | 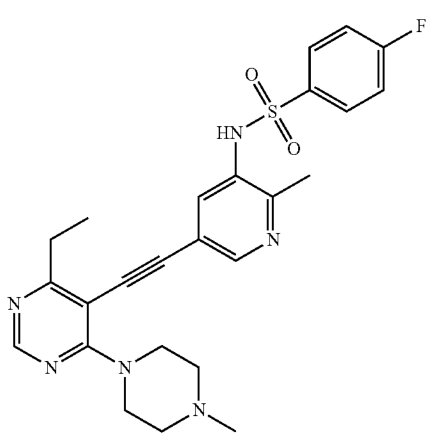 [SMILES: CCc1ncnc(N2CCN(C)CC2)c1C#Cc1cnc(C)c(NS(=O)(=O)c2ccc(F)cc2)c1] | N-{5-[4-Ethyl-6-(4-methyl-piperazin-1-yl)-pyrimidin-5-ylethynyl]-2-methyl-pyridin-3-yl}-4-fluoro-benzenesulfonamide | M + H = 495; tR = 1.14 |

TABLE 1-continued

Examples 1-47 to 1-80
Compounds 1-47 to 1-80 found in the table below may be prepared starting from the suitable intermediates described above and following similar procedures as for compounds I-1 to I-46.

| Ex. # | Molecular Structure | Name | HPLC-MS |
|---|---|---|---|
| I-66 | 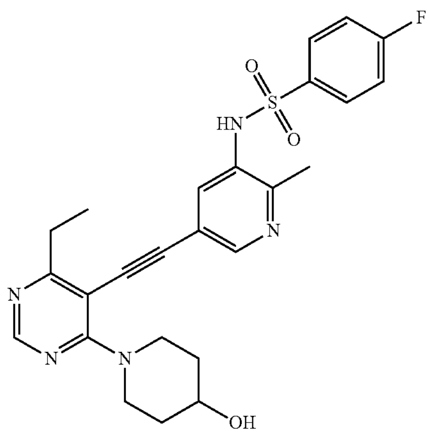 [SMILES: CCc1ncnc(N2CCC(O)CC2)c1C#Cc1cnc(C)c(NS(=O)(=O)c2ccc(F)cc2)c1] | N-{5-[4-Ethyl-6-(4-hydroxy-piperidin-1-yl)-pyrimidin-5-ylethynyl]-2-methyl-pyridin-3-yl}-4-fluoro-benzenesulfonamide | M + H = 496; tR = 1.09 |
| I-67 | 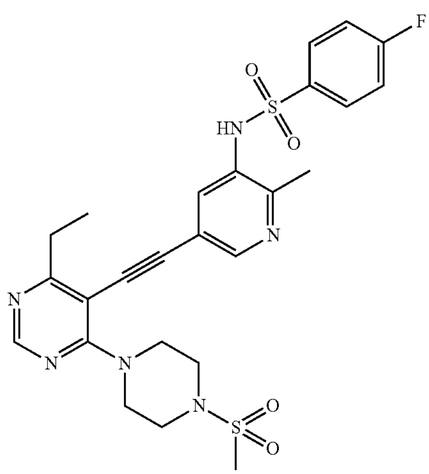 [SMILES: CCc1ncnc(N2CCN(S(C)(=O)=O)CC2)c1C#Cc1cnc(C)c(NS(=O)(=O)c2ccc(F)cc2)c1] | N-{5-[4-Ethyl-6-(4-methanesulfonyl-piperazin-1-yl)-pyrimidin-5-ylethynyl]-2-methyl-pyridin-3-yl}-4-fluoro-benzenesulfonamide | M + H = 559; tR = 1.16 |
| I-68 | 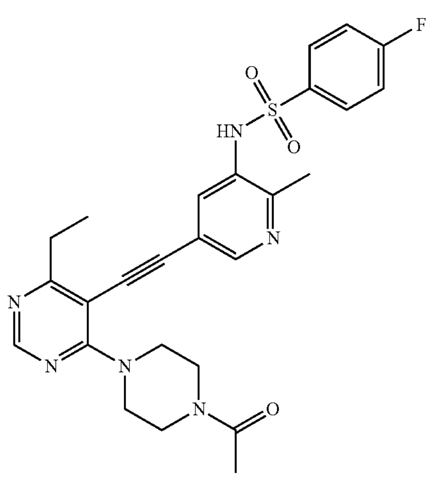 [SMILES: CCc1ncnc(N2CCN(C(C)=O)CC2)c1C#Cc1cnc(C)c(NS(=O)(=O)c2ccc(F)cc2)c1] | N-{5-[4-(4-Acetyl-piperazin-1-yl)-6-ethyl-pyrimidin-5-ylethynyl]-2-methyl-pyridin-3-yl}-4-fluoro-benzenesulfonamide | M + H = 523; tR = 1.10 |

TABLE 1-continued

Examples 1-47 to 1-80

Compounds 1-47 to 1-80 found in the table below may be prepared starting from the suitable intermediates described above and following similar procedures as for compounds I-1 to 1-46.

| Ex. # | Molecular Structure | Name | HPLC-MS |
|---|---|---|---|
| I-69 | 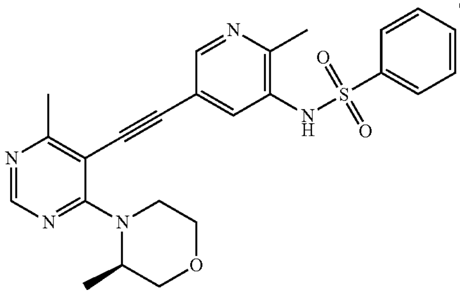 | Chiral N-{2-Methyl-5-[4-methyl-6-((R)-3-methyl-morpholin-4-yl)-pyrimidin-5-ylethynyl]-pyridin-3-yl}-benzenesulfonamide | M + H = 464; tR = 0 and 0.98 |
| I-70 | 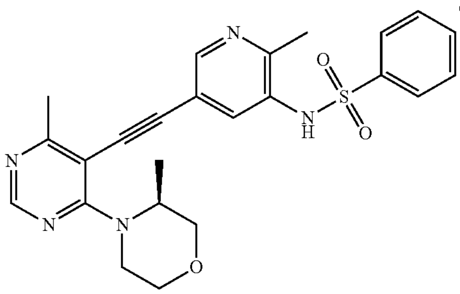 | Chiral N-{2-Methyl-5-[4-methyl-6-((S)-3-methyl-morpholin-4-yl)-pyrimidin-5-ylethynyl]-pyridin-3-yl}-benzenesulfonamide | M + H = 464; tR = 0 |
| I-71 | 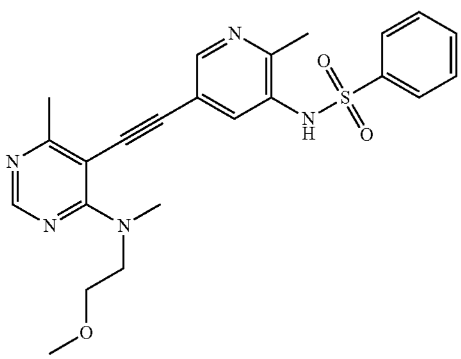 [SMILES: COCCN(C)c1ncnc(C)c1C#Cc1cnc(C)c(NS(=O)(=O)c2ccccc2)c1] | N-(5-{4-[(2-Methoxy-ethyl)-methyl-amino]-6-methyl-pyrimidin-5-ylethynyl}-2-methyl-pyridin-3-yl)-benzenesulfonamide | M + H = 452; tR = 0.84 und 0.87 |
| I-72 | 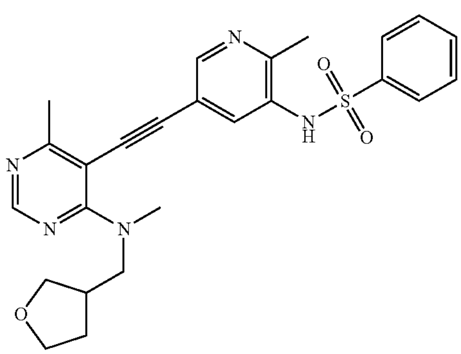 [SMILES: Cc1ncc(C#Cc2c(C)ncnc2N(C)CC2CCOC2)cc1NS(=O)(=O)c1ccccc1] | N-(2-Methyl-5-{4-methyl-6-[methyl-(tetrahydro-furan-3-ylmethyl)-amino]-pyrimidin-5-ylethynyl}-pyridin-3-yl)-benzenesulfonamide | M + H = 478; tR = 0 and 0.88; |

TABLE 1-continued

Examples 1-47 to 1-80

Compounds 1-47 to 1-80 found in the table below may be prepared starting from the suitable intermediates described above and following similar procedures as for compounds I-1 to 1-46.

| Ex. # | Molecular Structure | Name | HPLC-MS |
|---|---|---|---|
| I-73 | 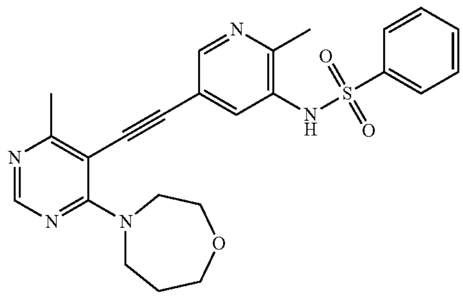 [SMILES: Cc1ncc(C#Cc2c(C)ncnc2N2CCCOCC2)cc1NS(=O)(=O)c1ccccc1] | N-[2-Methyl-5-(4-methyl-6-[1,4]oxazepan-4-yl-pyrimidin-5-ylethynyl)-pyridin-3-yl]-benzenesulfonamide | M + H = 464; tR = 0.80/0.86 |
| I-74 | 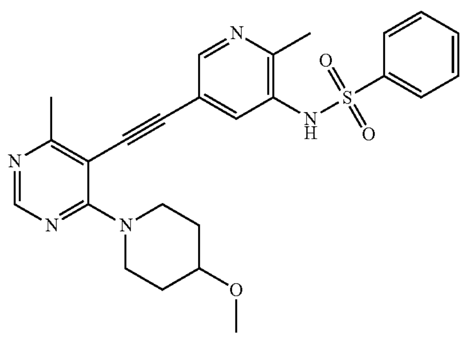 [SMILES: COC1CCN(c2ncnc(C)c2C#Cc2cnc(C)c(NS(=O)(=O)c3ccccc3)c2)CC1] | N-{5-[4-(4-Methoxy-piperidin-1-yl)-6-methyl-pyrimidin-5-ylethynyl]-2-methyl-pyridin-3-yl}-benzenesulfonamide | M + H = 478; tR = 0.91 |
| I-75 | 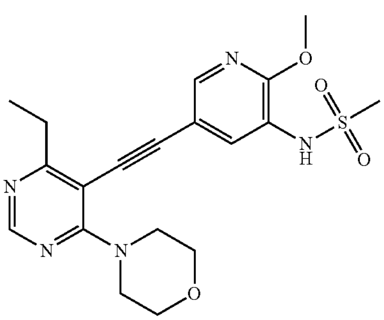 [SMILES: CCc1ncnc(N2CCOCC2)c1C#Cc1cnc(OC)c(NS(C)(=O)=O)c1] | N-[5-(4-Ethyl-6-morpholin-4-yl-pyrimidin-5-ylethynyl)-2-methoxy-pyridin-3-yl]-methanesulfonamide | M + H = 418; tR = 0 |
| I-76 | 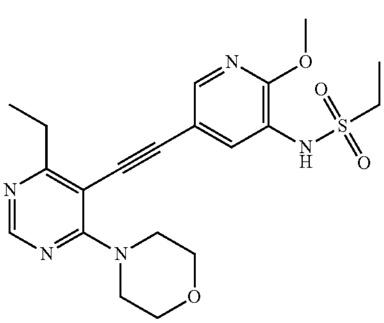 [SMILES: CCc1ncnc(N2CCOCC2)c1C#Cc1cnc(OC)c(NS(=O)(=O)CC)c1] | Ethanesulfonic acid [5-(4-ethyl-6-morpholin-4-yl-pyrimidin-5-ylethynyl)-2-methoxy-pyridin-3-yl]-amide | M + H = 432; tR = 0.83 und 0.89 |

TABLE 1-continued

Examples 1-47 to 1-80
Compounds 1-47 to 1-80 found in the table below may be prepared starting from the suitable intermediates described above and following similar procedures as for compounds I-1 to 1-46.

| Ex. # | Molecular Structure | Name | HPLC-MS |
|---|---|---|---|
| I-77 | 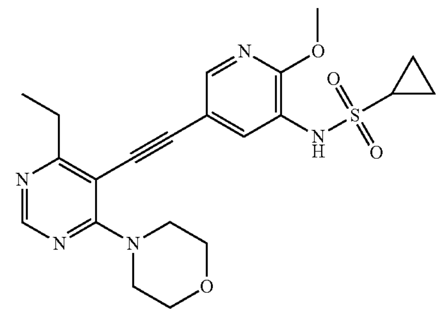 [SMILES: CCc1ncnc(N2CCOCC2)c1C#Cc1cnc(OC)c(NS(=O)(=O)C2CC2)c1] | Cyclopropanesulfonic acid [5-(4-ethyl-6-morpholin-4-yl-pyrimidin-5-ylethynyl)-2-methoxy-pyridin-3-yl]-amide | M + H = 444; tR = 0.90 |
| I-78 | 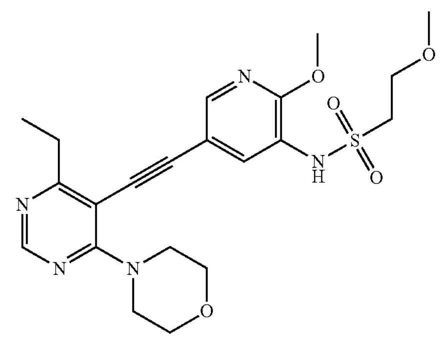 [SMILES: CCc1ncnc(N2CCOCC2)c1C#Cc1cnc(OC)c(NS(=O)(=O)CCOC)c1] | 2-Methoxy-ethanesulfonic acid [5-(4-ethyl-6-morpholin-4-yl-pyrimidin-5-ylethynyl)-2-methoxy-pyridin-3-yl]-amide | M + H = 462; tR = 0.91 und 0.96 |
| I-79 | 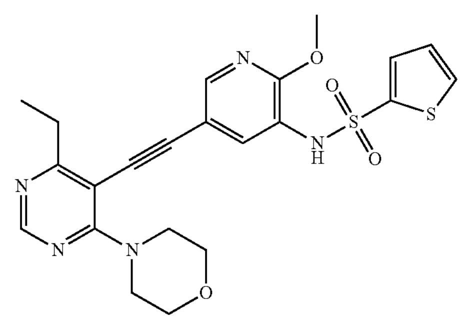 | Thiophene-2-sulfonic acid [5-(4-ethyl-6-morpholin-4-yl-pyrimidin-5-ylethynyl)-2-methoxy-pyridin-3-yl]-amide | M + H = 486; tR = 0.94 |
| I-80 | 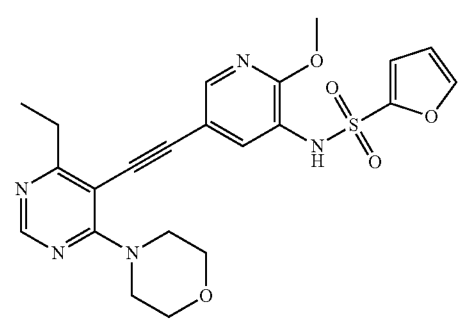 | Furan-2-sulfonic acid [5-(4-ethyl-6-morpholin-4-yl-pyrimidin-5-ylethynyl)-2-methoxy-pyridin-3-yl]-amide | M + H = 470; tR = 0, 0.55 und 0.89 |

I-81) N-[2-methoxy-5-(4-methyl-6-morpholin-4-yl-pyrimidin-5-ylethynyl)-pyridin-3-yl]-methylsulfonamide

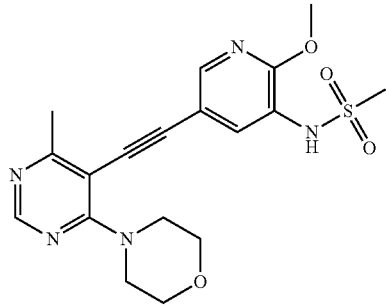 [SMILES: COc1ncc(C#Cc2c(C)ncnc2N2CCOCC2)cc1NS(C)(=O)=O]

To 100 mg (0.31 mmol) 2-Methoxy-5-(4-methyl-6-morpholin-4-yl-pyrimidin-5-ylethynyl)-pyridin-3-ylamine (E-9) in 5 mL DCM is added 70 mg (0.61 mmol) methanesulfonyl chloride and 72 µL (0.91 mmol) pyridine and the reaction mixture is stirred over night at RT. Water (2 mL) is added and the reaction mixture is extracted three times with 4 mL ethylacetate. The combined organic phases are dried over MgSO$_4$ and concentrated under reduced pressure. The crude product is purified by RP chromatography (C18, 20-80% ACN in water containing 1% formic acid). Yield: 32 mg (18%). HPLC-MS: M+H=404; tR=0.65 min.

I-82) 2-Trifluoromethoxy-N-[2-methoxy-5-(4-methyl-6-morpholin-4-yl-pyrimidin-5-ylethynyl)-pyridin-3-yl]-benzenesulfonamide

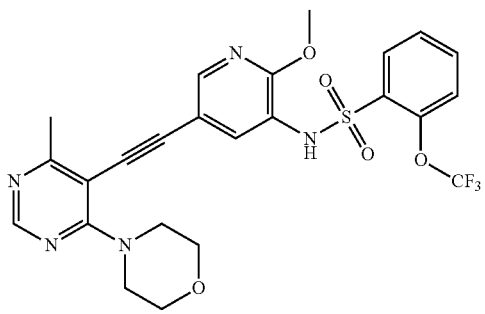 [SMILES: COc1ncc(C#Cc2c(C)ncnc2N2CCOCC2)cc1NS(=O)(=O)c1ccccc1OC(F)(F)F]

To 100 mg (0.31 mmol) 2-Methoxy-5-(4-methyl-6-morpholin-4-yl-pyrimidin-5-ylethynyl)-pyridin-3-ylamine (E-9) in 5 mL DCM is added 160 mg (0.61 mmol) 2,4-trifluoromethoxybenzenesulfonyl chloride and 72 µL (0.97 mmol) pyridine and the reaction mixture is stirred over night at RT. Water (2 mL) is added, the mixture is shaken for five minutes, the aqueous phase is separated and is extracted three times with 4 mL DCM. The combined organic phases are dried over MgSO$_4$ and concentrated under reduced pressure. The crude product is purified by RP chromatography (C18, 20-80% ACN in water containing 1% formic acid). Yield: 115 mg (68%). HPLC-MS: M+H=550; tR=0.92 min.

I-83) 2-Trifluoromethyl-N-[2-methoxy-5-(4-methyl-6-morpholin-4-yl-pyrimidin-5-ylethynyl)-pyridin-3-yl]-benzenesulfonamide

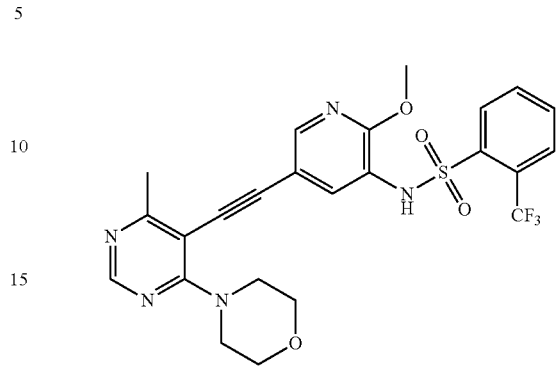

To 100 mg (0.31 mmol) 2-Methoxy-5-(4-methyl-6-morpholin-4-yl-pyrimidin-5-ylethynyl)-pyridin-3-ylamine (E-9) in 5 mL DCM is added 160 mg (0.61 mmol) 2,4-trifluoromethoxybenzenesulfonyl chloride and 72 µL (0.97 mmol) pyridine and the reaction mixture is stirred over night at RT. Water (2 mL) is added, the mixture is shaken for five minutes, the aqueous phase is separated and is extracted three times with 4 mL DCM. The combined organic phases are dried over MgSO$_4$ and concentrated under reduced pressure. The crude product is purified by RP chromatography (C18, 20-80% ACN in water containing 1% formic acid). Yield: 124 mg (76%). HPLC-MS: M+H=534; tR=0.89 min.

I-84) 4-Chloro-N-[2-methoxy-5-(4-methyl-6-morpholin-4-yl-pyrimidin-5-ylethynyl)-pyridin-3-yl]-benzenesulfonamide

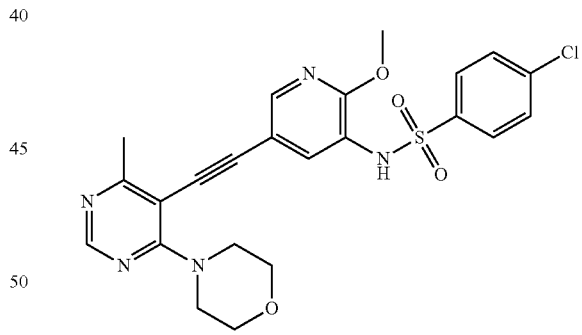

To 100 mg (0.31 mmol) 2-Methoxy-5-(4-methyl-6-morpholin-4-yl-pyrimidin-5-ylethynyl)-pyridin-3-ylamine (E-9) in 5 mL DCM is added 130 mg (0.61 mmol) 4-chlorobenzenesulfonyl chloride and 72 µL (0.97 mmol) pyridine and the reaction mixture is stirred over night at RT. Water (2 mL) is added, the mixture is shaken for five minutes, the aqueous phase is separated and is extracted three times with 4 mL DCM. The combined organic phases are dried over MgSO$_4$ and concentrated under reduced pressure. The crude product is purified by RP chromatography (C18, 20-80% ACN in water containing 1% formic acid). Yield: 105 mg (76%). HPLC-MS: M+H=500; tR=0.91 min.

I-85) 5-Chloro-N-[2-methoxy-5-(4-methyl-6-morpholin-4-yl-pyrimidin-5-ylethynyl)-pyridin-3-yl]-thiophene-2-sulfonamide

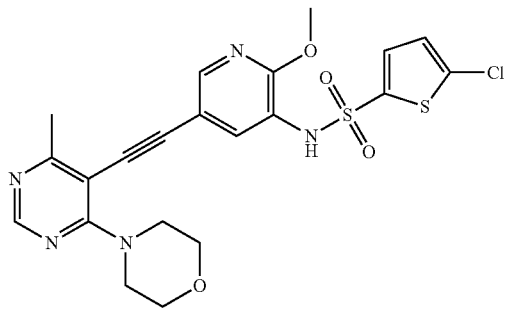 [SMILES: COc1ncc(C#Cc2c(C)ncnc2N2CCOCC2)cc1NS(=O)(=O)c1ccc(Cl)s1]

To 100 mg (0.31 mmol) 2-Methoxy-5-(4-methyl-6-morpholin-4-yl-pyrimidin-5-ylethynyl)-pyridin-3-ylamine (E-9) in 5 mL DCM is added 112 mg (0.61 mmol) 5-chloro-thiophen-2-sulfonyl chloride and 72 μL (0.97 mmol) pyridine and the reaction mixture is stirred over night at RT. Water (2 mL) is added, the mixture is shaken for five minutes, the aqueous phase is separated and is extracted three times with 4 mL DCM. The combined organic phases are dried over MgSO$_4$ and concentrated under reduced pressure. The crude product is purified by RP chromatography (C18, 20-80% ACN in water containing 1% formic acid). Yield: 101 mg (65%). HPLC-MS: M+H=506/508; tR=0.91 min.

I-86) N-[2-Methoxy-5-(4-methyl-6-morpholin-4-yl-pyrimidin-5-ylethynyl)-pyridin-3-yl]-thiophene-2-sulfonamide

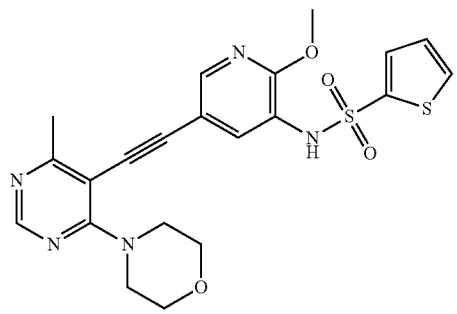 [SMILES: COc1ncc(C#Cc2c(C)ncnc2N2CCOCC2)cc1NS(=O)(=O)c1cccs1]

To 100 mg (0.31 mmol) 2-Methoxy-5-(4-methyl-6-morpholin-4-yl-pyrimidin-5-ylethynyl)-pyridin-3-ylamine (E-9) in 5 mL DCM is added 112 mg (0.61 mmol) thiophen-2-sulfonyl chloride and 72 μL (0.97 mmol) pyridine and the reaction mixture is stirred over night at RT. Water (2 mL) is added, the mixture is shaken for five minutes, the aqueous phase is separated and is extracted three times with 4 mL DCM. The combined organic phases are dried over MgSO$_4$ and concentrated under reduced pressure. The crude product is purified by RP chromatography (C18, 20-80% ACN in water containing 1% formic acid). Yield: 95 mg (65%). HPLC-MS: M+H=472; tR=0.82 min.

I-87) N-[2-methoxy-5-[2-(4-methyl-6-morpholin-4-ylpyrimidin-5-yl)ethynyl]pyridin-3-yl]-2-methylpyrazole-3-sulfonamide

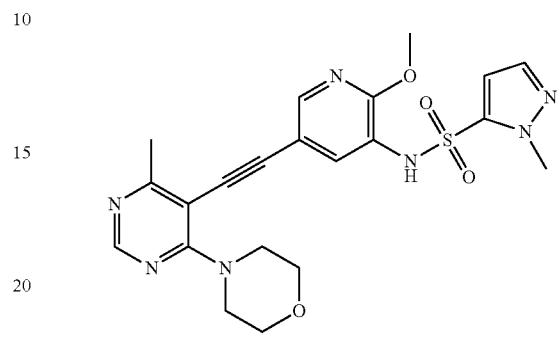

To 100 mg (0.31 mmol) 2-Methoxy-5-(4-methyl-6-morpholin-4-yl-pyrimidin-5-ylethynyl)-pyridin-3-ylamine (E-9) in 5 mL DCM is added 111 mg (0.61 mmol) 1-methyl-1H-pyrazole-5-sulfonyl chloride and 72 μL (0.97 mmol) pyridine and the reaction mixture is stirred over night at RT. Water (2 mL) is added, the mixture is shaken for five minutes, the aqueous phase is separated and is extracted three times with 4 mL DCM. The combined organic phases are dried over MgSO$_4$ and concentrated under reduced pressure. The crude product is purified by RP chromatography (C18, 20-80% ACN in water containing 1% formic acid). Yield: 32 mg (22%). HPLC-MS: M+H=470; tR=0.78 min.

I-88) N-[2-methoxy-5-[2-(4-methyl-6-morpholin-4-ylpyrimidin-5-yl)ethynyl]pyridin-3-yl]-1-methylpyrazole-4-sulfonamide

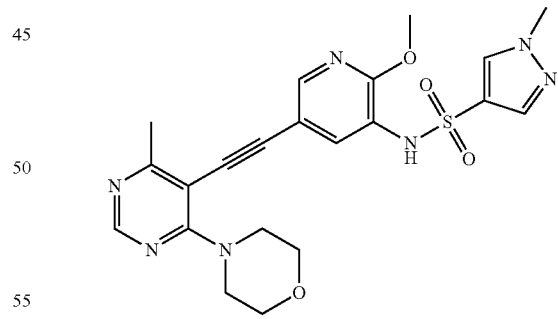

To 100 mg (0.31 mmol) 2-Methoxy-5-(4-methyl-6-morpholin-4-yl-pyrimidin-5-ylethynyl)-pyridin-3-ylamine (E-9) in 5 mL DCM is added 111 mg (0.61 mmol) 1-methyl-1H-pyrazole-4-sulfonyl chloride and 72 μL (0.97 mmol) pyridine and the reaction mixture is stirred over night at RT. Water (2 mL) is added, the mixture is shaken for five minutes, the aqueous phase is separated and is extracted three times with 4 mL DCM. The combined organic phases are dried over MgSO$_4$ and concentrated under reduced pressure. The crude product is purified by RP chromatography (C18, 20-80%

ACN in water containing 1% formic acid). Yield: 101 mg (70%). HPLC-MS: M+H=470; tR=0.72 min.

I-89) N-[2-methoxy-5-[2-(4-methyl-6-morpholin-4-ylpyrimidin-5-yl)ethynyl]pyridin-3-yl]-5-methylfuran-2-sulfonamide

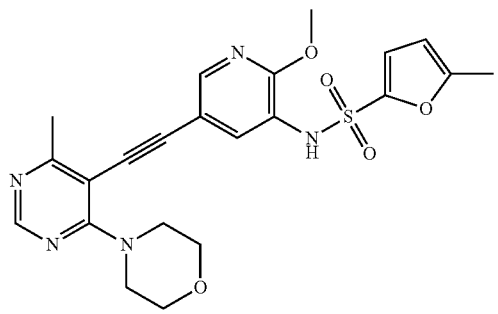 [SMILES: COc1ncc(C#Cc2c(C)ncnc2N2CCOCC2)cc1NS(=O)(=O)c1ccc(C)o1]

To 100 mg (0.31 mmol) 2-Methoxy-5-(4-methyl-6-morpholin-4-yl-pyrimidin-5-ylethynyl)-pyridin-3-ylamine (E-9) in 5 mL DCM is added 111 mg (0.61 mmol) 5-methylfuran-2-sulfonyl chloride and 72 µL (0.97 mmol) pyridine and the reaction mixture is stirred over night at RT. Water (2 mL) is added, the mixture is shaken for five minutes, the aqueous phase is separated and is extracted three times with 4 mL DCM. The combined organic phases are dried over MgSO$_4$ and concentrated under reduced pressure. The crude product is purified by RP chromatography (C18, 20-80% ACN in water containing 1% formic acid). Yield: 78 mg (54%). HPLC-MS: M+H=470; tR=0.83 min.

Biological Methods
Inhibition of PI3Kalpha-Induced PIP-2 Phosphorylation

This PI3Kalpha assay provides an IC$_{50}$ value indicative of the activity of the compounds to inhibit PI3 kinase alpha activity. Inhibition of PI3 kinase would be expected to be indicative of activity in treating conditions of excessive or anomalous cell proliferation, such as cancers. See also J. A. Engelman, Nature Reviews Cancer, 2009, 9, 550-562; A. Carnero, Expert Opin. Investig. Drugs, 2009, 18, 1265-1277 and P. Liu et al., Nature Reviews Drug Discovery, 2009, 8, 627-64.

Method Type: Filter-Binding-Assay
1. Materials
Assay buffer: 40 mM HEPES pH 7.5 SIGMA H-3375
   100 mM NaCl Merck 1.064.041.000
   1 mM EGTA SIGMA E-4378
   1 mM β-Glycerophosphate SIGMA G-6253
   7 mM MgCl 2 Merck 58.331.000
   1 mM DTT SIGMA D-0632
   (0.1% BSA only during preparation of Lipidmix after ultrasonication)
Phospholipid blend mix (=substrate) from Avanti Polar Lipids (#790770):
   Phosphatidylinositol-4,5-biphosphate (#840046) 3.665%
   Phosphatidylethanolamine (#83022) 39.26%
   Phosphatidylserine (#830032) 36.66%
   Sphingomyeline (#860062) 3.665%
   Phosphatidylcholine (#830053) 16.75%
Per aliquot lipid (16.6 mg): 26 ml assay buffer+520 µl BSA (5%)
PI3 Kinase alpha was expressed in SF9 insect cells, coinfected with viruses encoding p85alpha and His-p110alpha, purified by combined Ni-affinity and anion exchange chromatography). Aliquoted in desired amounts and stored at −80° C. Final assay concentration 25 ng/well
Phosphotyrosin PDGFRbeta-peptide H-CGG-pY-MDM-SKDESVD-pY-VPMLDM-NH2 was synthesized by Jerini Peptide Technologies (JPT) and used in a final conc. of 1.7 µM (stock 100 µM prepared in Assay buffer with DTT, aliquoted in desired amounts and stored at −80° C.)
Cold ATP (from Sigma; A-7699), 100 µM stock solution in H2O, use 1 µM final concentration in assay
[33P]-ATP, 370 MBq/ml from Amersham (#AH9968), use 0.5 µCi/well (10 mCi/ml)
Clear 96-well plates from Greiner (#655 162)
Filter plates: Perkin Elmer UniFilter GF/B #6005177
Microscint 0 (from Perkin Elmer, #6013611)
2. Assay Procedure The substrate-containing lipid vesicles are dissolved to a concentration of 0.637 mg lipid blend/ml assay buffer (with BSA, freshly added) in 50 ml Falcon->keep on ice, followed by ultrasonication (pulse of 15 sec followed by a pause of 10 sec, 4×). Compounds are serially diluted in assay buffer+6% DMSO and 10 l of each dilution is added per well of a 96-well plate (compounds are tested in duplicates) and mixed with 30 µl of the lipid vesicles containing PDGFR-Peptide (0.5 M final) and PI3K alpha (25 ng/well final). The mixture is then incubated for 20 minutes at room temperature. Subsequently, 20 µl of assay buffer containing 3 M cold ATP and 0.5 µCi/20 µl 33P-ATP are added. The plates are then incubated at room temperature for 120 minutes (shaking with 300 rpm).

The reaction mix is transferred onto filter plates using "filtermate harvester" from Packard: filter plates are rinsed with PBS, then the reaction mix is filtered onto the filter plate, washed 5 times with PBS and are allowed to dry for 30-60 minutes at 50° C.

The plate bottom is sealed with Perkin Elmer white adhesive foil and 25 µl/well Microscint( ) are added, the top is covered with transparent adhesive foil and the plate is measured with Wallac Trilux 1450 Microbeta Counter.

As positive control serve wells containing vehicle controls (1% DMSO in assay buffer), showing non-inhibited kinase activity (high values). Wells containing assay buffer instead of enzyme can serve as control for background activity (low values).

3. Evaluation
Calculate IC$_{50}$ values using the Smiley program (based on GrapPad Prism)

AlamarBlue—H460, MB453, U87, MCF7 and BT474 cell assay

The H460, MB453, U87, MCF7 and BT474 alamarBlue cell assays provide EC$_{50}$ values indicative of the antiproliferative or cytotoxic effects of the compounds to respectively the H460 (human non small cell line cancer), MB-453 (breast cancer cell line), U87 (glioblastoma cell line), MCF7 (breast cancer cell line) and BT474 (breast cancer cell line). As known in the field, antiproliferative or cytotoxic effect against this cell lines would be expected to be indicative of activity in treating lung, breast and brain cancers. See R. Marone R et al. Biochim. Biophys. Acta. 2008 January; 1784(1):159-85. S. Yaguchi et al., J. Natl. Cancer Inst. 2006 Apr. 19; 98(8):545-56.

Method Type: Antiproliferative/Cytotoxicity
1. Description
alamarBlue® is designed to provide a rapid and sensitive measure of cell proliferation and cytotoxicity in various human and animal cell lines. The assay is based on the reduction of alamarBlue in the reducing environment of living (metabolically active) cells. In the presence of added cytotoxic or antiproliferative compounds, the innate metabolic activity ceases.

AlamarBlue is soluble and stable in culture medium. Measurements are made fluorometrically by exciting at 530-560 nm and measuring emission at 590 nm. In reporting percent alamarBlue reduction by monitoring fluorescence, data are expressed as fluorescence emission intensity units as a function of time of incubation.

2. Cells and Reagents

| | |
|---|---|
| H460 cells | Human lung carcinoma cells (ATCC HTB-177) |
| alamarBlue | Serotec Ltd |
| PBS (w/o Ca, Mg) | Life Technologies, Gibco BRL (Cat. No. 4190-094) |
| RPMI1640 Medium | Life Technologies, Gibco BRL (Cat. No. 61870-010) |
| Fetal calf serum | Life Technologies, Gibco BRL (Cat. No. 10270-106) |
| BT-474 cells | Human Breast Cancer Cell Line (ATCC HTB-20) |
| alamarBlue | Serotec Ltd |
| IMDM Medium | Cambrex Biowhittaker (Cat. No. BE-12-722F) |
| NEAA | |
| Sodiumpyruvat | |
| PBS (w/o Ca, Mg) | Life Technologies, Gibco BRL (Cat. No. 4190-094) |
| Fetal calf serum | Life Technologies, Gibco BRL (Cat. No. 10270-106) |
| MCF7 cells | Human Breast Cancer Cell Line |
| alamarBlue | Serotec Ltd |
| IMDM Medium | Cambrex Biowhittaker (Cat. No. BE-12-722F) |
| NEAA | |
| Sodiumpyruvat | |
| PBS (w/o Ca, Mg) | Life Technologies, Gibco BRL (Cat. No. 4190-094) |
| Fetal calf serum | Life Technologies, Gibco BRL (Cat. No. 10270-106) |
| U-87MG cells | Human glioblastoma cells (ATCC HTB-14) |
| CyQuant NF assay | Invitrogen Cat.# C35006 |
| PBS (w/o Ca, Mg) | Life Technologies, Gibco BRL (Cat. No. 4190-094) |
| RPMI1640 Medium | Life Technologies, Gibco BRL (Cat. No. 61870-010) |
| Fetal calf serum | Life Technologies, Gibco BRL (Cat. No. 10270-106) |
| MB453 cells | MDA MB 453 cells (ATCC HTB-131) |
| Alamar Blue | Serotec BUF012B |
| RPMI | |
| Fetal calf serum | Life Technologies, Gibco BRL (Cat. No. 10270-106) (w/o PhenolRed, L-Glutamin) |

3. Equipment
   96-well plates, flat bottom (Falcon, Cat. No.: 353072)
   96-well plates, U-shaped (Costar, Cat. No.: 3799)
   $CO_2$-Incubator
   Microplate Reader, Spectramax Plus, Molecular Devices 4. Typical Procedure
   Day 0: Seed 3000 BT-474 cells (IMDM/5% FCS, 1% NEAA, 1% Sodiumpyruvat) in 150 µl medium into a 96-well plate, flat bottom (include mediumblank). Incubate plates at 37° C. in a $CO_2$ incubator overnight.
   Day 1: Dilute compounds to a concentration 40 µM->1:3 in medium, 10 dilution steps, in 96-well plates.
      Add 50 µl per well of each dilution (total volume per well 200 µl; final conc. of cpds: 10 µM->1:3). If required, test further dilutions.
      All concentrations are tested in duplicates.
      Controls: Cells w/o cpd. (+50 µl medium/DMSO).
      Cells are incubated with compounds for 5-6 days.
   Day 6 or 7: Add 25 µl of alamarBlue solution to each well and incubate for 8 hours at 37° C. Measure fluorescence by exciting at 530-560 nm and measuring emission at 590 nm.

5. Evaluation
   Subtract average value for medium blank from sample readings
   Calculate $EC_{50}$ using GraphPad Prism (Fifty)

TABLE 2

Biological Data for Examples I-1 to I-89
The $IC_{50}$ and $EC_{50}$ values representing the biological activity of the compounds of the examples are listed in the table below.
All $IC_{50}$ and $EC_{50}$ values are reported in nM.

| Example | $IC_{50}$ PI3Kα | $EC_{50}$ H460 | $EC_{50}$ MB453 | $EC_{50}$ U87 | $EC_{50}$ MCF7 | $EC_{50}$ BT474 |
|---|---|---|---|---|---|---|
| I-1 | 0.4 | 19 | 47 | 55 | 4 | 14 |
| I-2 | 0.65 | 234 | 168 | 342 | 43 | 148 |
| I-3 | 5 | 315 | 777 | 529 | 451 | 1035 |
| I-4 | 1 | 114 | 294 | 467 | 296 | 246 |
| I-5 | 1 | 64 | 202 | 271 | 61 | 152 |
| I-6 | 1 | 130 | 259 | 368 | 75 | 194 |
| I-7 | 0.8 | 108 | 146 | 223 | 38 | 82 |
| I-8 | 1 | 47 | 143 | 205 | 46 | 134 |
| I-9 | 1 | 1459 | 1069 | 1447 | 748 | 856 |
| I-10 | 0.72 | 42 | 113 | 126 | 67 | 116 |
| I-11 | 1 | 56 | 298 | 466 | 190 | 271 |
| I-12 | 4 | 486 | 839 | 1286 | 464 | 684 |
| I-13 | 0.63 | 23 | 63 | 108 | 18 | 69 |
| I-14 | 0.85 | 245 | 444 | 615 | 114 | 252 |
| I-15 | 0.74 | 376 | 898 | 1674 | 163 | 318 |
| I-16 | 0.86 | 226 | 397 | 839 | 118 | 309 |
| I-17 | 0.79 | 965 | 521 | 1887 | 73 | 354 |
| I-18 | 1 | 269 | 418 | 358 | 72 | 221 |
| I-19 | 0.46 | 319 | 387 | 707 | 56 | 373 |
| I-20 | 0.46 | 391 | 281 | 521 | 22 | 153 |
| I-21 | 0.53 | 357 | 155 | 340 | 40 | 196 |
| I-22 | 0.8 | 4502 | 1416 | 10000 | 1378 | 3407 |
| I-23 | 0.66 | 2185 | 1035 | 1748 | 214 | 3504 |
| I-24 | 4 | | | | 1107 | 2356 |
| I-25 | 0.63 | 15 | 46 | 104 | 11 | 22 |
| I-26 | 0.59 | 21 | 61 | 97 | 9 | 28 |
| I-27 | 1 | 791 | 1222 | 1617 | 10000 | 10000 |
| I-28 | 5 | 756 | 1854 | 14440 | 10000 | 10000 |
| I-29 | 0.44 | 11 | 28 | 84 | 3 | 10 |
| I-30 | 0.43 | 230 | 148 | 385 | 21 | 122 |
| I-31 | 0.97 | 509 | 245 | 609 | 50 | 178 |
| I-32 | 8 | 1207 | 656 | 1294 | 617 | 1883 |
| I-33 | 49 | | | | | |
| I-34 | 2 | | | | 74 | 433 |
| I-35 | 5 | 25000 | | | | |
| I-36 | 5 | | | | | |
| I-37 | 1 | 903 | 318 | 966 | 134 | 416 |
| I-38 | 2 | 829 | 642 | 836 | 304 | 1221 |
| I-39 | 5 | 1848 | 1788 | 2912 | 1292 | 2769 |
| I-40 | 0.28 | 120 | 145 | 386 | 49 | 147 |
| I-41 | 0.51 | 146 | 102 | 287 | 19 | 69 |
| I-42 | 0.55 | 295 | | | | |
| I-43 | 3 | 3672 | | | | |
| I-44 | 2 | 117 | | | | |
| I-45 | 4 | 141 | | | 62 | 284 |
| I-46 | 0.86 | 880 | | | 397 | 1268 |
| I-47 | 21 | 25000 | 25000 | 25000 | 10000 | 10000 |
| I-48 | 0.55 | 100 | 533 | 341 | 14 | 754 |
| I-49 | 2 | 356 | 393 | 512 | 49 | 444 |
| I-50 | 1 | 128 | 239 | 289 | 16 | 330 |
| I-51 | 0.56 | 196 | 199 | 315 | 12 | 311 |
| I-52 | 0.47 | 274 | 298 | 443 | 39 | 224 |
| I-53 | 2 | 793 | 915 | 1276 | 135 | 884 |
| I-54 | 1 | 553 | 274 | 581 | 44 | 949 |
| I-55 | 1 | 1176 | 1680 | 1979 | 208 | 1546 |
| I-56 | 0.44 | 756 | 239 | 779 | 125 | 487 |
| I-57 | 0.83 | 82 | 443 | 338 | 2 | 1296 |
| I-58 | 16 | 2992 | 4642 | 25000 | 1299 | 3000 |
| I-59 | 6 | 723 | 1926 | 1001 | | 5000 |
| I-60 | 2 | 1252 | 618 | 945 | 103 | 1545 |
| I-61 | 2 | 791 | 262 | 631 | 39 | 1119 |
| I-62 | 3 | 1742 | 969 | 1292 | 709 | 4053 |
| I-63 | 3 | 308 | 1331 | 1296 | 126 | 4319 |
| I-64 | 2 | 71 | 584 | 773 | 59 | 5953 |
| I-65 | 0.89 | 168 | 230 | 524 | 28 | 281 |
| I-66 | 0.48 | 444 | 175 | 540 | 145 | 91 |
| I-67 | 0.14 | 37 | 54 | 471 | 9 | 44 |
| I-68 | 0.47 | 542 | 116 | 545 | 36 | 117 |
| I-69 | 2 | | | | | 749 |
| I-70 | 0.2 | | | | | 615 |
| I-71 | 5 | 1622 | 2105 | 1193 | | 1500 |

TABLE 2-continued

Biological Data for Examples I-1 to I-89
The $IC_{50}$ and $EC_{50}$ values representing the biological activity of the compounds of the examples are listed in the table below.
All $IC_{50}$ and $EC_{50}$ values are reported in nM.

| Example | $IC_{50}$ PI3Kα | $EC_{50}$ H460 | $EC_{50}$ MB453 | $EC_{50}$ U87 | $EC_{50}$ MCF7 | $EC_{50}$ BT474 |
|---|---|---|---|---|---|---|
| I-72 | 8 | | | | | 5159 |
| I-73 | 2 | | | | | 1939 |
| I-74 | 2 | 703 | 987 | 557 | | 400 |
| I-75 | 1 | | | | | 247 |
| I-76 | 2 | | | | | 342 |
| I-77 | 1 | | | | | 263 |
| I-78 | 2 | | | | | 469 |
| I-79 | 0.75 | | | | | 20 |
| I-80 | 0.55 | | | | | 40 |
| I-81 | 0.64 | 181 | 233 | 510 | | 76 |
| I-82 | 0.5 | 24 | 27 | 50 | | 25 |
| I-83 | 0.44 | 6 | 7 | 18 | | 6 |
| I-84 | 0.3 | 41 | 49 | 24 | | 48 |
| I-85 | 0.38 | 47 | 40 | 64 | | 34 |
| I-86 | 0.39 | 10 | 14 | 42 | | 12 |
| I-87 | 0.45 | 30 | 15 | 54 | | 20 |
| I-88 | 0.55 | 21 | 8 | 27 | | 62 |
| I-89 | 0.53 | 26 | 38 | 42 | | 63 |

On the basis of their biological properties the compounds of general formula (I) according to the invention, their tautomers, racemates, enantiomers, diastereomers, mixtures thereof and the salts of all the above-mentioned forms are suitable for treating diseases characterised by excessive or abnormal cell proliferation or by aberrant activation of the phosphatidylinositol-3-kinase (PI3K) signal pathway.

Such diseases include for example: viral infections (e.g. HIV and Kaposi's sarcoma); inflammatory and autoimmune diseases (e.g. colitis, arthritis, Alzheimer's disease, glomerulonephritis and wound healing); bacterial, fungal and/or parasitic infections; leukaemias, lymphomas and solid tumours (e.g. carcinomas and sarcomas), skin diseases (e.g. psoriasis); diseases based on hyperplasia which are characterised by an increase in the number of cells (e.g. fibroblasts, hepatocytes, bones and bone marrow cells, cartilage or smooth muscle cells or epithelial cells (e.g. endometrial hyperplasia)); bone diseases and cardiovascular diseases (e.g. restenosis and hypertrophy).

For example, the following cancers may be treated with compounds according to the invention, without being restricted thereto: brain tumours such as for example acoustic neurinoma, astrocytomas such as pilocytic astrocytomas, fibrillary astrocytoma, protoplasmic astrocytoma, gemistocytary astrocytoma, anaplastic astrocytoma and glioblastoma, brain lymphomas, brain metastases, hypophyseal tumour such as prolactinoma, HGH (human growth hormone) producing tumour and ACTH producing tumour (adrenocorticotropic hormone), craniopharyngiomas, medulloblastomas, meningeomas and oligodendrogliomas; nerve tumours (neoplasms) such as for example tumours of the vegetative nervous system such as neuroblastoma sympathicum, ganglioneuroma, paraganglioma (pheochromocytoma, chromaffinoma) and glomus-caroticum tumour, tumours on the peripheral nervous system such as amputation neuroma, neurofibroma, neurinoma (neurilemmoma, Schwannoma) and malignant Schwannoma, as well as tumours of the central nervous system such as brain and bone marrow tumours; intestinal cancer such as for example carcinoma of the rectum, colon carcinoma, colorectal carcinoma, anal carcinoma, carcinoma of the large bowel, tumours of the small intestine and duodenum; eyelid tumours such as basalioma or basal cell carcinoma; pancreatic cancer or carcinoma of the pancreas; bladder cancer or carcinoma of the bladder; lung cancer (bronchial carcinoma) such as for example small-cell bronchial carcinomas (oat cell carcinomas) and non-small cell bronchial carcinomas (NSCLC) such as plate epithelial carcinomas, adenocarcinomas and large-cell bronchial carcinomas; breast cancer such as for example mammary carcinoma such as infiltrating ductal carcinoma, colloid carcinoma, lobular invasive carcinoma, tubular carcinoma, adenocystic carcinoma and papillary carcinoma; non-Hodgkin's lymphomas (NHL) such as for example Burkitt's lymphoma, low-malignancy non-Hodgkin's lymphomas (NHL) and mucosis fungoides; uterine cancer or endometrial carcinoma or corpus carcinoma; CUP syndrome (Cancer of Unknown Primary); ovarian cancer or ovarian carcinoma such as mucinous, endometrial or serous cancer; gall bladder cancer; bile duct cancer such as for example Klatskin tumour; testicular cancer such as for example seminomas and non-seminomas; lymphoma (lymphosarcoma) such as for example malignant lymphoma, Hodgkin's disease, non-Hodgkin's lymphomas (NHL) such as chronic lymphatic leukaemia, leukaemic reticuloendotheliosis, immunocytoma, plasmocytoma (multiple myeloma), immunoblastoma, Burkitt's lymphoma, T-zone mycosis fungoides, large-cell anaplastic lymphoblastoma and lymphoblastoma; laryngeal cancer such as for example tumours of the vocal cords, supraglottal, glottal and subglottal laryngeal tumours; bone cancer such as for example osteochondroma, chondroma, chondroblastoma, chondromyxoid fibroma, osteoma, osteoid osteoma, osteoblastoma, eosinophilic granuloma, giant cell tumour, chondrosarcoma, osteosarcoma, Ewing's sarcoma, reticulo-sarcoma, plasmocytoma, fibrous dysplasia, juvenile bone cysts and aneurysmatic bone cysts; head and neck tumours such as for example tumours of the lips, tongue, floor of the mouth, oral cavity, gums, palate, salivary glands, throat, nasal cavity, paranasal sinuses, larynx and middle ear; liver cancer such as for example liver cell carcinoma or hepatocellular carcinoma (HCC); leukaemias, such as for example acute leukaemias such as acute lymphatic/lymphoblastic leukaemia (ALL), acute myeloid leukaemia (AML); chronic leukaemias such as chronic lymphatic leukaemia (CLL), chronic myeloid leukaemia (CML); stomach cancer or gastric carcinoma such as for example papillary, tubular and mucinous adenocarcinoma, signet ring cell carcinoma, adenosquamous carcinoma, small-cell carcinoma and undifferentiated carcinoma; melanomas such as for example superficially spreading, nodular, lentigo-maligna and acral-lentiginous melanoma; renal cancer such as for example kidney cell carcinoma or hypernephroma or Grawitz's tumour; oesophageal cancer or carcinoma of the oesophagus; penile cancer; prostate cancer; throat cancer or carcinomas of the pharynx such as for example nasopharynx carcinomas, oropharynx carcinomas and hypopharynx carcinomas; retinoblastoma such as for example vaginal cancer or vaginal carcinoma; plate epithelial carcinomas, adenocarcinomas, in situ carcinomas, malignant melanomas and sarcomas; thyroid carcinomas such as for example papillary, follicular and medullary thyroid carcinoma, as well as anaplastic carcinomas; spinalioma, epidormoid carcinoma and plate epithelial carcinoma of the skin; thymomas, cancer of the urethra and cancer of the vulva.

Preferred cancer types, which might be treated with the compounds of the invention, are those where the pathway is activated by either mutation of PI3K or loss of PTEN. Preferred cancers, which may be treated with compounds according to the invention, are lung, liver, colon, brain, breast, ovary and prostate cancer.

The new compounds may be used for the prevention, short-term or long-term treatment of the above-mentioned diseases, optionally also in combination with radiotherapy or other "state-of-the-art" compounds, such as e.g. cytostatic or cytotoxic substances, cell proliferation inhibitors, anti-angiogenic substances, steroids or antibodies.

The compounds of general formula (1) may be used on their own or in combination with other active substances according to the invention, optionally also in combination with other pharmacologically active substances.

Chemotherapeutic agents which may be administered in combination with the compounds according to the invention, include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors (growth factors such as for example "platelet derived growth factor" and "hepatocyte growth factor", inhibitors are for example "growth factor" antibodies, "growth factor receptor" antibodies and tyrosine kinase inhibitors, such as for example cetuximab, gefitinib, imatinib, lapatinib and trastuzumab); antimetabolites (e.g. antifolates such as methotrexate, raltitrexed, pyrimidine analogues such as 5-fluorouracil, capecitabin and gemcitabin, purine and adenosine analogues such as mercaptopurine, thioguanine, cladribine and pentostatin, cytarabine, fludarabine); antitumour antibiotics (e.g. anthracyclins such as doxorubicin, daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); topoisomerase inhibitors (e.g. epipodophyllotoxins such as for example etoposide and etopophos, teniposide, amsacrin, topotecan, irinotecan, mitoxantron) and various chemotherapeutic agents such as amifostin, anagrelid, clodronat, filgrastin, interferon alpha, leucovorin, rituximab, procarbazine, levamisole, mesna, mitotane, pamidronate and porfimer.

Other possible combination partners are 2-chlorodesoxyadenosine, 2-fluorodesoxycytidine, 2-methoxyoestradiol, 2C4,3-alethine, 131-I-TM-601, 3CPA, 7-ethyl-10-hydroxycamptothecin, 16-aza-epothilone B, A 105972, A 204197, aldesleukin, alitretinoin, altretamine, alvocidib, amonafide, anthrapyrazole, AG-2037, AP-5280, apaziquone, apomine, aranose, arglabin, arzoxifene, atamestane, atrasentan, auristatin PE, AVLB, AZ10992, ABX-EGF, ARRY-300, ARRY-142886/AZD-6244, ARRY-704/AZD-8330, AS-703026, azacytidine, azaepothilone B, azonafide, BAY-43-9006, BBR-3464, BBR-3576, bevacizumab, biricodar dicitrate, BCX-1777, bleocin, BLP-25, BMS-184476, BMS-247550, BMS-188797, BMS-275291, BNP-1350, BNP-7787, BIBW 2992, BIBF 1120, bleomycinic acid, bleomycin A, bleomycin B, bryostatin-1, bortezomib, brostallicin, busulphan, CA-4 prodrug, CA-4, CapCell, calcitriol, canertinib, canfosfamide, capecitabine, carboxyphthalatoplatin, CCI-779, CEP-701, CEP-751, CBT-1 cefixime, ceflatonin, ceftriaxone, celecoxib, celmoleukin, cemadotin, CH4987655/RO-4987655, chlorotrianisene, cilengitide, ciclosporin, CDA-II, CDC-394, CKD-602, clofarabin, colchicin, combretastatin A4, CHS-828, CLL-Thera, CMT-3 cryptophycin 52, CTP-37, CP-461, CV-247, cyanomorpholinodoxorubicin, cytarabine, D 24851, decitabine, deoxorubicin, deoxyrubicin, deoxycoformycin, depsipeptide, desoxyepothilone B, dexamethasone, dexrazoxanet, diethylstilbestrol, diflomotecan, didox, DMDC, dolastatin 10, doranidazole, E7010, E-6201, edatrexat, edotreotide, efaproxiral, eflornithine, EKB-569, EKB-509, elsamitrucin, epothilone B, epratuzumab, ER-86526, erlotinib, ET-18-OCH3, ethynylcytidine, ethynyloestradiol, exatecan, exatecan mesylate, exemestane, exisulind, fenretinide, floxuridine, folic acid, FOLFOX, FOLFIRI, formestane, galarubicin, gallium maltolate, gefinitib, gemtuzumab, gimatecan, glufosfamide, GCS-IOO, G17DT immunogen, GMK, GPX-100, GSK-5126766, GSK-1120212, GW2016, granisetron, hexamethylmelamine, histamine, homoharringtonine, hyaluronic acid, hydroxyurea, hydroxyprogesterone caproate, ibandronate, ibritumomab, idatrexate, idenestrol, IDN-5109, IMC-1C11, immunol, indisulam, interferon alpha-2a, interferon alfa-2b, interleukin-2, ionafarnib, iproplatin, irofulven, isohomohalichondrin-B, isoflavone, isotretinoin, ixabepilone, JRX-2, JSF-154, J-107088, conjugated oestrogens, kahalid F, ketoconazole, KW-2170, lobaplatin, leflunomide, lenograstim, leuprolide, leuporelin, lexidronam, LGD-1550, linezolid, lutetium texaphyrin, lometrexol, losoxantrone, LU 223651, lurtotecan, mafosfamide, marimastat, mechloroethamine, methyltestosteron, methylprednisolone, MEN-10755, MDX-H210, MDX-447, MGV, midostaurin, minodronic acid, mitomycin, mivobulin, MK-2206, MLN518, motexafin gadolinium, MS-209, MS-275, MX6, neridronate, neovastat, nimesulide, nitroglycerin, nolatrexed, norelin, N-acetylcysteine, 06-benzylguanine, omeprazole, oncophage, ormiplatin, ortataxel, oxantrazole, oestrogen, patupilone, pegfilgrastim, PCK-3145, pegfilgrastim, PBI-1402, PEG-paclitaxel, PEP-005, P-04, PKC412, P54, PI-88, pelitinib, pemetrexed, pentrix, perifosine, perillylalcohol, PG-TXL, PG2, PLX-4032/RO-5185426, PT-100, picoplatin, pivaloyloxymethylbutyrate, pixantrone, phenoxodiol 0, PKI166, plevitrexed, plicamycin, polyprenic acid, porfiromycin, prednisone, prednisolone, quinamed, quinupristin, RAF-265, ramosetron, ranpirnase, RDEA-119/BAY 869766, rebeccamycin analogues, revimid, RG-7167, rhizoxin, rhuMAb, risedronate, rituximab, rofecoxib, Ro-31-7453, RO-5126766, RPR 109881A, rubidazon, rubitecan, R-flurbiprofen, S-9788, sabarubicin, SAHA, sargramostim, satraplatin, SB 408075, SU5416, SU6668, SDX-101, semustin, seocalcitol, SM-11355, SN-38, SN-4071, SR-27897, SR-31747, SRL-172, sorafenib, spiroplatin, squalamine, suberanilohydroxamic acid, sutent, T 900607, T 138067, TAS-103, tacedinaline, talaporfin, tariquitar, taxotere, taxoprexin, tazarotene, tegafur, temozolamide, tesmilifene, testosterone, testosterone propionate, tesmilifene, tetraplatin, tetrodotoxin, tezacitabine, thalidomide, theralux, therarubicin, thymectacin, tiazofurin, tipifarnib, tirapazamine, tocladesine, tomudex, toremofin, trabectedin, TransMID-107, transretinic acid, traszutumab, tretinoin, triacetyluridine, triapine, trimetrexate, TLK-286TXD 258, urocidin, valrubicin, vatalanib, vincristine, vinflunine, virulizin, WX-UK1, vectibix, xeloda, XELOX, XL-281, XL-518/R-7420, YM-511, YM-598, ZD-4190, ZD-6474, ZD-4054, ZD-0473, ZD-6126, ZD-9331, ZDI839, zoledronat and zosuquidar.

Suitable preparations include for example tablets, capsules, suppositories, solutions—particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may, of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour.

The dosage for tablets use is from 1-10000 mg per patient per day, preferably 10-1000 mg per patient per day.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The invention claimed is:
1. A compound of the Formula (I)

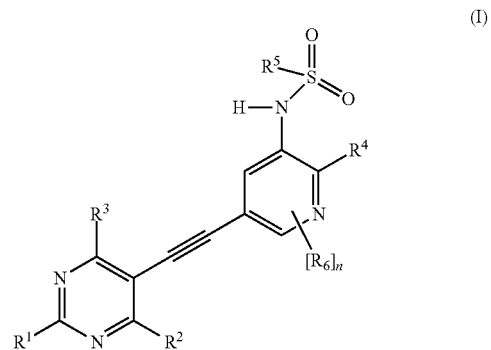

wherein
$R^1$ is —H or —$NH_2$;
$R^2$ is —$N(R^7, R^8)$;
$R^3$ is —$C_{1-5}$alkyl;
$R^4$ is selected from halogen, —CN, —$C_{1-5}$alkyl, —O—$C_{1-5}$alkyl, —$C_{1-5}$alkyl-O—$C_{1-5}$alkyl or —O—$C_{1-5}$-haloalkyl;
$R^5$ is selected from —$C_{1-5}$alkyl, —$C_{2-5}$alkenyl, —$C_{2-5}$alkynyl, —$C_{3-10}$cycloalkyl, 3-14 membered heterocyclyl, all of which groups can be optionally and independently substituted with one or more =O, —CN, =S, halogen, $R^{15}$ or $R^{16}$,
or $R^5$ is selected from —$C_{6-10}$aryl or 5-12 membered heteroaryl, all of which groups can be optionally and independently substituted with one or more —CN, halogen, $R^{15}$ or $R^{16}$;
or $R^5$ is —$N(R^{12}, R^{13})$;
$R^6$ is selected from halogen, —CN, —$C_{1-5}$alkyl, —$C_{1-5}$-haloalkyl, —O—$C_{1-5}$alkyl, —$C_{1-5}$alkyl-O—$C_{1-5}$alkyl or —O—$C_{1-5}$-haloalkyl;
n is 0, 1 or 2;
$R^7$ is selected from —H, —$C_{1-5}$alkyl, —$C_{2-5}$alkenyl, —$C_{2-5}$alkynyl, —$C_{3-10}$cycloalkyl, 3-14 membered heterocyclyl, —$C_{1-5}$alkyl-O—$R^9$, —$C_{1-5}$alkyl-S—$R^9$, or —$C_{1-5}$alkyl-N($R^9$,$R^{10}$), all of which groups can be optionally and independently substituted with one or more =O, —CN, =S, halogen, or $R^{11}$,
$R^8$ is selected from —O—$C_{1-5}$alkyl, —S—$C_{1-5}$alkyl, —$C_{1-5}$alkyl, —$C_{2-5}$alkenyl, —$C_{2-5}$alkynyl, —$C_{3-10}$cycloalkyl, 3-14 membered heterocyclyl, —$C_{1-5}$alkyl-O—$R^9$, —$C_{1-5}$alkyl-S—$R^9$, or —$C_{1-5}$alkyl-N($R^9$,$R^{10}$), all of which groups can be optionally and independently substituted with one or more =O, —CN, =S, halogen, or $R^{11}$,
or $R^7$, $R^8$ are the same or different, independently selected from —$C_{6-10}$aryl, 5-12 membered heteroaryl, all of which groups can be optionally and independently substituted with one or more —CN, halogen, or $R^{11}$,
or $R^7$ and $R^8$ taken together with the nitrogen atom to which they are attached form a partially or fully saturated 3-14 membered heterocyclyl which group can be optionally and independently substituted with one or more =O, —CN, =S, halogen, or $R^{11}$;

$R^9$ is selected from —H, —$C_{1-5}$alkyl, —$C_{2-5}$alkenyl, —$C_{2-5}$alkynyl, —$C_{3-10}$cycloalkyl, 3-14 membered heterocyclyl, —$C_{1-5}$alkyl-O—$C_{1-5}$alkyl, —$C_{1-5}$alkyl-S—$C_{1-5}$alkyl, or —$C_{1-5}$alkyl-N($C_{1-5}$alkyl, $C_{1-5}$alkyl), all of which groups can be optionally and independently substituted with one or more =O, —CN, =S, halogen, or $R^{11}$, $R^{10}$ is selected from —H, —O—$C_{1-5}$alkyl, —$C_{1-5}$alkyl, —$C_{2-5}$alkenyl, —$C_{2-5}$alkynyl, —$C_{3-10}$cycloalkyl, 3-14 membered heterocyclyl, —$C_{1-5}$alkyl-O—$C_{1-5}$alkyl, —$C_{1-5}$alkyl-S—$C_{1-5}$alkyl or —$C_{1-5}$alkyl-N($C_{1-5}$alkyl, $C_{1-5}$alkyl), all of which groups can be optionally and independently substituted with one or more =O, —CN, =S, halogen, or $R^{11}$, or $R^9$, $R^{10}$ are the same or different, independently selected from —$C_{6-10}$aryl, 5-12 membered heteroaryl, all of which groups can be optionally and independently substituted with one or more —CN, halogen, or $R^{11}$, or $R^9$ and $R^{10}$ taken together with the atom to which they are attached form a 3-14 membered heterocyclyl which group can be optionally and independently substituted with one or more =O, —CN, =S, halogen, or $R^1$;

$R^{11}$ is selected from —OH, —$NH_2$, —$CF_3$, —$OCF_3$, —$OCHF_2$, —$S(O)_2CH_3$, —$C(O)CH_3$, or nitro, or $R^{11}$ is selected from —$C_{6-10}$aryl or 5-12 membered heteroaryl, all of which groups can be optionally and independently substituted with one or more —CN, halogen, —OH, —$NH_2$, —$CH_3$, —$CH_2CH_3$, —$CF_3$, —$S(O)_2CH_3$, —$C(O)CH_3$, -propyl, -isopropyl, -cyclopropyl, -butyl, iso-butyl-, tert-butyl-, -cyclobutyl, -cyclopentyl, -cyclohexyl, —NH—$CH_3$, —N($CH_3$)$_2$, —N($CH_2CH_3$)$_2$, —NH—$CH_2CH_3$, —N($CH_3$,$CH_2CH_3$), —O—$CH_3$, —O—$CH_2CH_3$, —S—$CH_3$, —C(O)NH$CH_3$, —C(O)N($CH_3$)$_2$, —C(O)NH—$CH_2CH_3$, —C(O)N($CH_2CH_3$)$_2$, —C(O)-pyrazolidinyl, —$OCF_3$, —$OCHF_2$, -tetrahydrofuryl, -tetrahydropyranyl, —N-methylpiperazinyl, -pyrrolidinyl, -morpholinyl or -nitro;

or $R^{11}$ is selected from —NH—$C_{1-5}$alkyl, —N($C_{1-5}$alkyl, $C_{1-5}$alkyl), —O—$C_{1-5}$alkyl, —S—$C_{1-5}$alkyl, —$C_{1-5}$alkyl, —$C_{2-5}$alkenyl, —$C_{2-5}$alkynyl, —$C_{3-10}$cycloalkyl, 3-14 membered heterocyclyl, all of which groups can be optionally and independently substituted with one or more =O, —CN, =S, halogen, —OH, —$NH_2$, —$CH_3$, —$CH_2CH_3$, —$CF_3$, —$S(O)_2CH_3$, —$C(O)CH_3$, -propyl, -isopropyl, -cyclopropyl, -butyl, iso-butyl-, tert-butyl-, -cyclobutyl, -cyclopentyl, -cyclohexyl, —NH—$CH_3$, —N($CH_3$)$_2$, —N($CH_2CH_3$)$_2$, —NH—$CH_2CH_3$, —N($CH_3$,$CH_2CH_3$), —O—$CH_3$, —O—$CH_2CH_3$, —S—$CH_3$, —C(O)NH$CH_3$, —C(O)N($CH_3$)$_2$, —C(O)NH—$CH_2CH_3$, —C(O)N($CH_2CH_3$)$_2$, —C(O)-pyrazolidinyl, —$OCF_3$, —$OCHF_2$, -tetrahydrofuryl, -tetrahydropyranyl, —N-methylpiperazinyl, -pyrrolidinyl, -morpholinyl or -nitro;

$R^{12}$ is selected from —H, —$C_{1-5}$alkyl, —$C_{2-5}$alkenyl, —$C_{2-5}$alkynyl, —$C_{3-10}$cycloalkyl, 3-14 membered heterocyclyl, —$C_{1-5}$alkyl-O—$C_{1-5}$alkyl, —$C_{1-5}$alkyl-S—$C_{1-5}$alkyl or —$C_{1-5}$alkyl-N($C_{1-5}$alkyl, $C_{1-5}$alkyl), all of which groups can be optionally and independently substituted with one or more =O, —CN, =S, halogen, or $R^{14}$, $R^{13}$ is selected from —H, —O—$C_{1-5}$alkyl, —$C_{1-5}$alkyl, —$C_{2-5}$alkenyl, —$C_{2-5}$alkynyl, —$C_{3-10}$cycloalkyl, 3-14 membered heterocyclyl, —$C_{6-10}$aryl, 5-12 membered heteroaryl, —$C_{1-5}$alkyl-O—$C_{1-5}$alkyl, —$C_{1-5}$alkyl-S—$C_{1-5}$alkyl, or —$C_{1-5}$alkyl-N($C_{1-5}$alkyl, $C_{1-5}$alkyl), all of which groups can be optionally and independently substituted with one or more =O, —CN, =S, halogen, or $R^{14}$;

or $R^{12}$, $R^{13}$ are the same or different, independently selected from —$C_{6-10}$aryl, 5-12 membered heteroaryl, all of which groups can be optionally and independently substituted with one or more —CN, halogen, or $R^{14}$, or $R^{12}$ and $R^{13}$ taken together with the nitrogen atom to which they are attached form a 3-14 membered heterocyclyl which group can be optionally and independently substituted with one or more =O, —CN, =S, halogen, or $R^{14}$;

$R^{14}$ is selected from —OH, —$NH_2$, —$CF_3$, —$OCF_3$, —$OCHF_2$, —$S(O)_2CH_3$, —$C(O)CH_3$ or -nitro, or $R^{14}$ is selected from —$C_{6-10}$aryl, 5-12 membered heteroaryl all of which groups can be optionally and independently substituted with one or more —CN, halogen, —OH, —$NH_2$, —$CH_3$, —$CH_2CH_3$, —$CF_3$, —$S(O)_2CH_3$, —$C(O)CH_3$, -propyl, -isopropyl, -cyclopropyl, -butyl, iso-butyl-, tert-butyl-, -cyclobutyl, -cyclopentyl, -cyclohexyl, —NH—$CH_3$, —N($CH_3$)$_2$, —N($CH_2CH_3$)$_2$, —NH—$CH_2CH_3$, —N($CH_3$,$CH_2CH_3$), —O—$CH_3$, —O—$CH_2CH_3$, —S—$CH_3$, —C(O)NH$CH_3$, —C(O)N($CH_3$)$_2$, —C(O)NH—$CH_2CH_3$, —C(O)N($CH_2CH_3$)$_2$, —C(O)-pyrazolidinyl, —$OCF_3$, —$OCHF_2$, -tetrahydrofuryl, -tetrahydropyranyl, —N-methylpiperazinyl, -pyrrolidinyl, -morpholinyl or -nitro;

or $R^{14}$ is selected from —NH—$C_{1-5}$alkyl, —N($C_{1-5}$alkyl, —$C_{1-5}$alkyl), —O—$C_{1-5}$alkyl, —S—$C_{1-5}$alkyl, —$C_{1-5}$alkyl, —$C_{2-5}$alkenyl, —$C_{2-5}$alkynyl, —$C_{3-10}$cycloalkyl, 3-14 membered heterocyclyl, all of which groups can be optionally and independently substituted with one or more =O, —CN, =S, halogen, —H, —OH, —$NH_2$, —$CH_3$, —$CH_2CH_3$, —$CF_3$, —$S(O)_2CH_3$, —$C(O)CH_3$, -propyl, -isopropyl, -cyclopropyl, -butyl, iso-butyl-, tert-butyl-, -cyclobutyl, -cyclopentyl, -cyclohexyl, —NH—$CH_3$, —N($CH_3$)$_2$, —N($CH_2CH_3$)$_2$, —NH—$CH_2CH_3$, N($CH_3$,$CH_2CH_3$), —O—$CH_3$, —O—$CH_2CH_3$, —S—$CH_3$, —C(O)NH$CH_3$, —C(O)N($CH_3$)$_2$, —C(O)NH—$CH_2CH_3$, —C(O)N($CH_2CH_3$)$_2$, —C(O)-pyrazolidinyl, —$OCF_3$, —$OCHF_2$, -tetrahydrofuryl, -tetrahydropyranyl, —N-methylpiperazinyl, -pyrrolidinyl, -morpholinyl or -nitro;

$R^{15}$ and $R^{16}$ are the same or different, independently selected from:
  —OH, —$NH_2$, —$CF_3$, —$S(O)_2CH_3$, —$C(O)CH_3$, —$OCF_3$, —$OCHF_2$ or -nitro, or $R^{15}$ and $R^{16}$ are the same or different, independently selected from —$C_{6-10}$aryl or 5-12 membered heteroaryl, all of which groups can be optionally and independently substituted with one or more —CN, halogen, —OH, —$NH_2$, —$CH_3$, —$CH_2CH_3$, —$CF_3$, —$S(O)_2CH_3$, —$C(O)CH_3$, -propyl, -isopropyl, -cyclopropyl, -butyl, iso-butyl-, tert-butyl-, -cyclobutyl, -cyclopentyl, -cyclohexyl, —NH—$CH_3$, —N($CH_3$)$_2$, —N($CH_2CH_3$)$_2$, —NH—$CH_2CH_3$, —N($CH_3$,$CH_2CH_3$), —O—$CH_3$, —O—$CH_2CH_3$, —S—$CH_3$, —C(O)NH$CH_3$, —C(O)N($CH_3$)$_2$, —C(O)NH—$CH_2CH_3$, —C(O)N($CH_2CH_3$)$_2$, —C(O)-pyrazolidinyl, —$OCF_3$, —$OCHF_2$, -tetrahydrofuryl, -tetrahydropyranyl, —N-methylpiperazinyl, -pyrrolidinyl, -morpholinyl or -nitro;

or $R^{15}$ and $R^{16}$ are the same or different, independently selected from:
  —NH—$C_{1-5}$alkyl, —N($C_{1-5}$alkyl, $C_{1-5}$alkyl), —O—$C_{1-5}$alkyl, —S—$C_{1-5}$alkyl, —$C_{1-5}$alkyl, —$C_{2-5}$alkenyl, —$C_{2-5}$alkynyl, —$C_{3-10}$cycloalkyl, 3-14 membered heterocyclyl, all of which groups can be optionally and independently substituted with one or more =O, —CN, =S, halogen, —OH, —$NH_2$, —$CH_3$, —$CH_2CH_3$, —$CF_3$, —$S(O)_2CH_3$, —$C(O)CH_3$, -propyl, -isopropyl, -cyclopropyl, -butyl, iso-butyl-, tert-butyl-, -cyclobutyl, -cyclopentyl, -cyclohexyl, —NH—CH$_3$, —N(CH$_3$)$_2$, —N(CH$_2$CH$_3$)$_2$, —NH—CH$_2$CH$_3$, —N(CH$_3$,CH$_2$CH$_3$), —O—CH$_3$, —O—CH$_2$CH$_3$, —S—CH$_3$, —C(O)NHCH$_3$, —C(O)N(CH$_3$)$_2$, —C(O)NH—CH$_2$CH$_3$, —C(O)N(CH$_2$CH$_3$)$_2$, —C(O)-pyrazolidinyl, —OCF$_3$, —OCHF$_2$, -tetrahydrofuryl, -tetrahydropyranyl, —N-methylpiperazinyl, -pyrrolidinyl, -morpholinyl or -nitro;

or R$^{15}$ and R$^{16}$ taken together with the atom to which they are attached form a partially or fully saturated —C$_{3-10}$ cycloalkyl or 4-8 membered heterocyclyl all of which groups can be optionally and independently substituted with one or more =O, —CN, =S, halogen, —OH, —NH$_2$, —CH$_3$, —CH$_2$CH$_3$, —CF$_3$, —S(O)$_2$CH$_3$, —C(O)CH$_3$, -propyl, -isopropyl, -cyclopropyl, -butyl, iso-butyl-, tert-butyl-, -cyclobutyl, -cyclopentyl, -cyclohexyl, —NH—CH$_3$, —N(CH$_3$)$_2$, —N(CH$_2$CH$_3$)$_2$, —NH—CH$_2$CH$_3$, —N(CH$_3$,CH$_2$CH$_3$), —O—CH$_3$, —O—CH$_2$CH$_3$, —S—CH$_3$, —C(O)NHCH$_3$, —C(O)N(CH$_3$)$_2$, —C(O)NH—CH$_2$CH$_3$, —C(O)N(CH$_2$CH$_3$)$_2$, —C(O)-pyrazolidinyl, —OCF$_3$, —OCHF$_2$, -tetrahydrofuryl, -tetrahydropyranyl, —N-methylpiperazinyl, -pyrrolidinyl, -morpholinyl or -nitro;

or a salt thereof.

2. The compound of claim 1, wherein n is 0.

3. The compound of claim 1, wherein
R$^5$ is selected from —C$_{1-5}$alkyl, —C$_{3-10}$cycloalkyl, 3-14 membered heterocyclyl,
all of which groups can be optionally and independently substituted with one or more =O, —CN, =S, halogen, R$^{15}$ or R$^{16}$, wherein R$^{15}$ and R$^{16}$ are defined as in claim 1;
or R$^5$ is selected from —C$_{6-10}$aryl or 5-12 membered heteroaryl, all of which groups can be optionally and independently substituted with one or more —CN, halogen, R$^{15}$ or R$^{16}$, wherein R$^{15}$ and R$^{16}$ are defined as in claim 1.

4. The compound of claim 1, wherein
R$^5$ is 5-12 membered heteroaryl, optionally substituted with one or more of the substituents as defined in claim 1.

5. The compound of claim 4, wherein
R$^5$ is selected from pyridyl, imidazolyl, pyrrazolyl, thiophenyl, furyl, N-methyl-pyrazolyl, N-methyl-imidazolyl, all of which can be optionally and independently substituted with one or more —CN, halogen, R$^{15}$ or R$^{16}$.

6. The compound of claim 1, wherein
R$^5$ is selected from —C$_{1-5}$-alkyl, pyrrolidinyl, cyclopropyl, cyclohexyl or phenyl all of which groups can be optionally and independently substituted with one or more of the substituents as defined in claim 1.

7. The compound according to claim 1, wherein
R$^7$ is selected from —H, —C$_{1-5}$alkyl, —C$_{3-10}$cycloalkyl, 3-14 membered heterocyclyl or —C$_{1-5}$alkyl-N(R$^9$,R$^{10}$), all of which groups can be optionally and independently substituted with one or more =O, —CN, =S, halogen or R$^{11}$, and
R$^8$ is selected from —O—C$_{1-5}$alkyl, —S—C$_{1-5}$alkyl, —C$_{1-5}$alkyl, —C$_{3-10}$cycloalkyl, 3-14 membered heterocyclyl or —C$_{1-5}$alkyl-N(R$^9$,R$^{10}$), all of which groups can be optionally and independently substituted with one or more =O, —CN, =S, halogen, or R$^{11}$,
or R$^8$ is selected from —C$_{6-10}$aryl, 5-12 membered heteroaryl, all of which groups can be optionally and independently substituted with one or more —CN, halogen, or R$^{11}$,
wherein, R$^9$, R$^{10}$ and R$^{11}$ are as defined in claim 1.

8. The compound according to claim 1, wherein
R$^7$ and R$^8$ are taken together with the nitrogen atom to which they are attached form a partially or fully saturated 3-14 membered heterocyclyl, which group can be optionally and independently substituted with one or more =O, —CN, =S, halogen, or R$^{11}$, wherein R$^{11}$ is defined as in claim 1.

9. The compound according to claim 1, wherein
R$^2$ is morpholinyl or piperazinyl which can be optionally and independently substituted with one or more =O, —CN, =S, halogen, or R$^{11}$.

10. The compound according to claim 1, wherein R$^7$ is —C$_{1-3}$alkyl or tetrahydropyranyl.

11. The compound according to claim 1, wherein
R$^4$ is —C$_{1-5}$alkyl or —O—C$_{1-5}$alkyl.

12. The compound according to claim 1, wherein
R$^9$ is —C$_{1-5}$-alkyl, —C$_{3-10}$cycloalkyl, 3-14 membered heterocyclyl, —C$_{1-5}$alkyl-O—C$_{1-5}$alkyl, or —C$_{1-5}$alkyl-N(—C$_{1-3}$alkyl, —C$_{1-3}$alkyl), all of which groups can be optionally and independently substituted with one or more =O, —CN, =S, halogen, or R$^1$; and
R$^{10}$ is —H, —O—C$_{1-5}$alkyl, —C$_{1-5}$alkyl, —C$_{3-10}$cycloalkyl, 3-14 membered heterocyclyl, —C$_{1-5}$alkyl-O—C$_{1-5}$alkyl, or —C$_{1-5}$alkyl-N(—C$_{1-3}$alkyl, —C$_{1-3}$alkyl), all of which groups can be optionally and independently substituted with one or more =O, —CN, =S, halogen, or R$^{11}$,
wherein R$^{11}$ is defined as in claim 1.

13. The compound according to claim 1, wherein
R$^{12}$ and R$^{13}$ taken together with the atom to which they are attached form a 3-14 membered heterocyclyl which can be optionally and independently substituted with one or more =O, —CN, =S, halogen, or R$^{14}$,
wherein R$^{14}$ is defined as in claim 1.

14. A compound selected from the group consisting of:

| Ex. # | Molecular Structure | Name |
|---|---|---|
| I-1 | 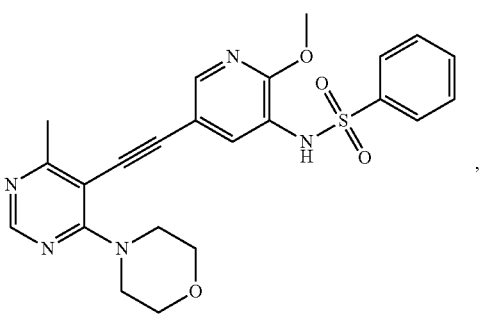 [SMILES: COc1ncc(C#Cc2c(C)ncnc2N2CCOCC2)cc1NS(=O)(=O)c1ccccc1] | N-[2-Methoxy-5-(4-methyl-6-morpholin-4-yl-pyrimidin-5-ylethynyl)-pyridin-3-yl]-benzenesulfonamide |

-continued

| Ex. # | Molecular Structure | Name |
|---|---|---|
| I-2 | 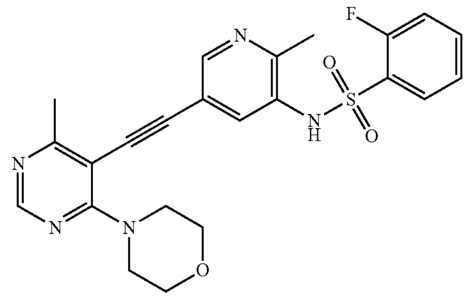 | 2-Fluoro-N-[2-methyl-5-(4-methyl-6-morpholin-4-yl-pyrimidin-5-ylethynyl)-pyridin-3-yl]-benzenesulfonamide |
| I-3 | 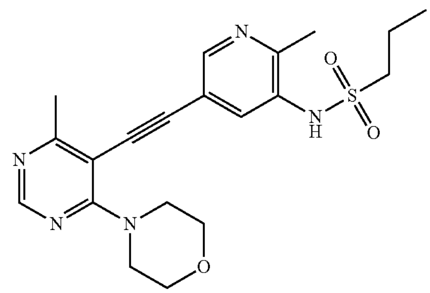 | Propane-1-sulfonic acid [2-methyl-5-(4-methyl-6-morpholin-4-yl-pyrimidin-5-ylethynyl)-pyridin-3-yl]-amide |
| I-4 | 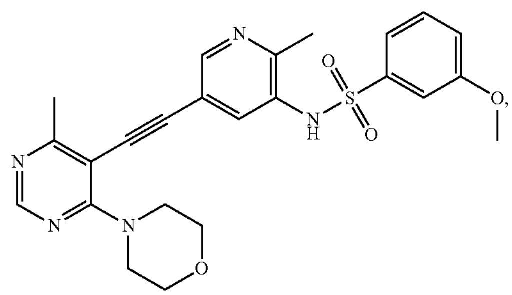 [SMILES: COc1cccc(S(=O)(=O)Nc2cc(C#Cc3c(C)ncnc3N3CCOCC3)cnc2C)c1] | 3-Methoxy-N-[2-methyl-5-(4-methyl-6-morpholin-4-yl-pyrimidin-5-ylethynyl)-pyridin-3-yl]-benzenesulfonamide |
| I-5 | 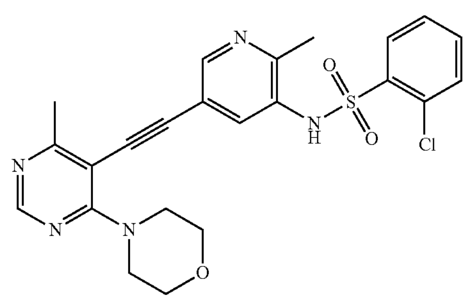 | 2-Chloro-N-[2-methyl-5-(4-methyl-6-morpholin-4-yl-pyrimidin-5-ylethynyl)-pyridin-3-yl]-benzenesulfonamide |
| I-6 | 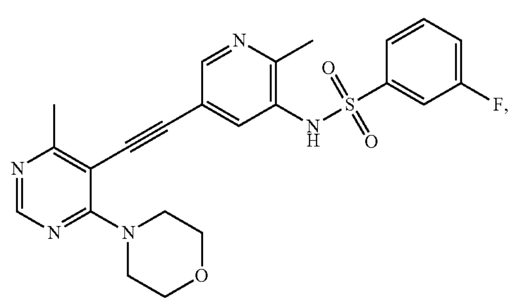 | 3-Fluoro-N-[2-methyl-5-(4-methyl-6-morpholin-4-yl-pyrimidin-5-ylethynyl)-pyridin-3-yl]-benzenesulfonamide |

| Ex. # | Molecular Structure | Name |
|---|---|---|
| I-7 | 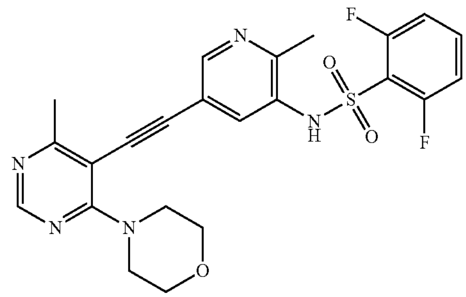 | 2,6-Difluoro-N-[2-methyl-5-(4-methyl-6-morpholin-4-yl-pyrimidin-5-ylethynyl)-pyridin-3-yl]-benzenesulfonamide |
| I-8 | 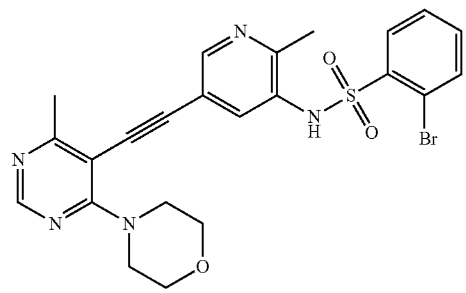 | 2-Bromo-N-[2-methyl-5-(4-methyl-6-morpholin-4-yl-pyrimidin-5-ylethynyl)-pyridin-3-yl]-benzenesulfonamide |
| I-9 | 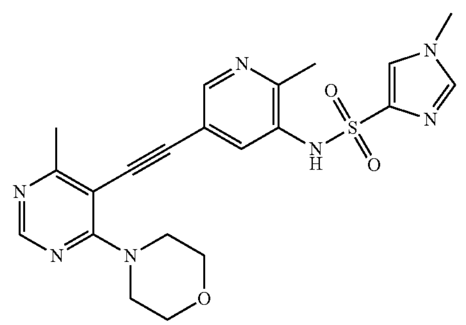 | 1-Methyl-1H-imidazole-4-sulfonic acid [2-methyl-5-(4-methyl-6-morpholin-4-yl-pyrimidin-5-ylethynyl)-pyridin-3-yl]-amide |
| I-10 | 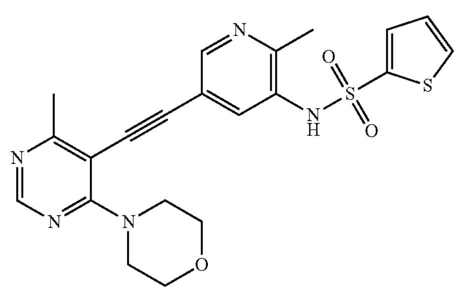 | Thiophene-2-sulfonic acid [2-methyl-5-(4-methyl-6-morpholin-4-yl-pyrimidin-5-ylethynyl)-pyridin-3-yl]-amide |
| I-11 | 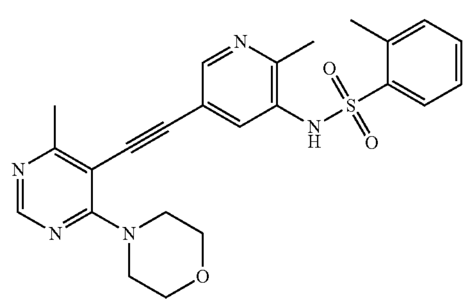 | 2-Methyl-N-[2-methyl-5-(4-methyl-6-morpholin-4-yl-pyrimidin-5-ylethynyl)-pyridin-3-yl]-benzenesulfonamide |

| Ex. # | Molecular Structure | Name |
|---|---|---|
| I-12 | 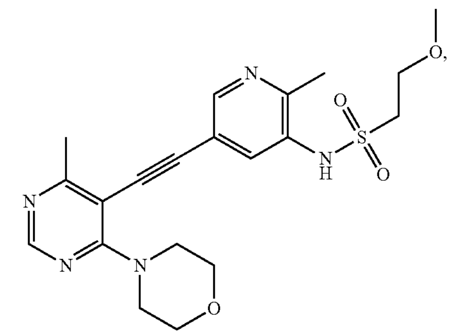 [SMILES: COCCS(=O)(=O)Nc1cc(C#Cc2c(C)ncnc2N2CCOCC2)cnc1C] | 2-Methoxy-ethanesulfonic acid [2-methyl-5-(4-methyl-6-morpholin-4-yl-pyrimidin-5-ylethynyl)-pyridin-3-yl]-amide |
| I-13 | 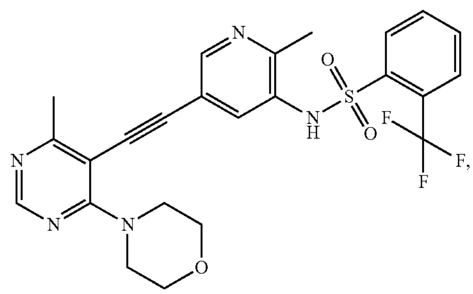 [SMILES: Cc1ncc(C#Cc2c(C)ncnc2N2CCOCC2)cc1NS(=O)(=O)c1ccccc1C(F)(F)F] | N-[2-Methyl-5-(4-methyl-6-morpholin-4-yl-pyrimidin-5-ylethynyl)-pyridin-3-yl]-2-trifluoromethyl-benzenesulfonamide |
| I-14 | 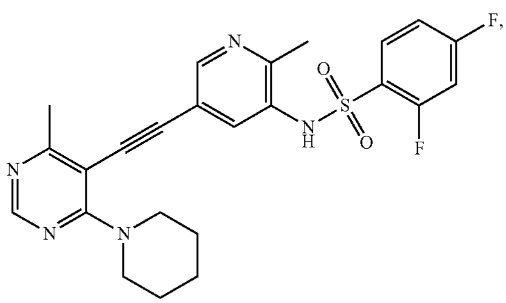 [SMILES: Cc1ncc(C#Cc2c(C)ncnc2N2CCCCC2)cc1NS(=O)(=O)c1ccc(F)cc1F] | 2,4-Difluoro-N-[2-methyl-5-(4-methyl-6-piperidin-1-yl-pyrimidin-5-ylethynyl)-pyridin-3-yl]-benzenesulfonamide |
| I-15 | 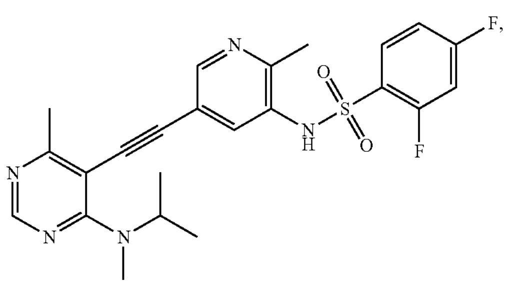 [SMILES: Cc1ncc(C#Cc2c(C)ncnc2N(C)C(C)C)cc1NS(=O)(=O)c1ccc(F)cc1F] | 2,4-Difluoro-N-{5-[4-(isopropyl-methyl-amino)-6-methyl-pyrimidin-5-ylethynyl]-2-methyl-pyridin-3-yl}-benzenesulfonamide |
| I-16 | 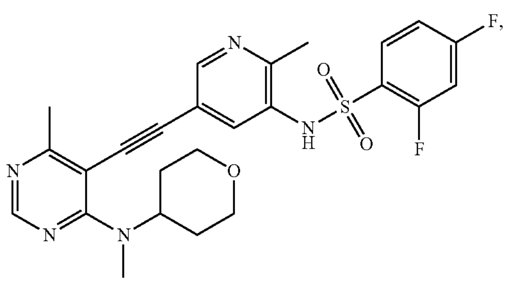 [SMILES: Cc1ncc(C#Cc2c(C)ncnc2N(C)C2CCOCC2)cc1NS(=O)(=O)c1ccc(F)cc1F] | 2,4-Difluoro-N-(2-methyl-5-{4-methyl-6-[methyl-(tetrahydro-pyran-4-yl)-amino]-pyrimidin-5-ylethynyl}-pyridin-3-yl)-benzenesulfonamide |

| Ex. # | Molecular Structure | Name |
|---|---|---|
| I-17 | 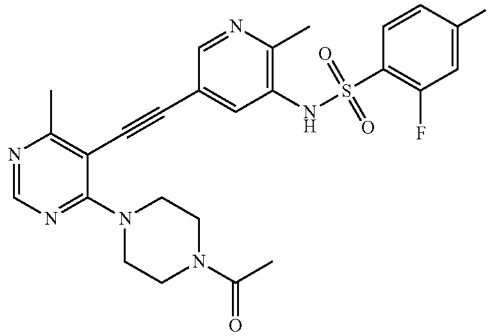 | N-{5-[4-(4-Acetyl-piperazin-1-yl)-6-methyl-pyrimidin-5-ylethynyl]-2-methyl-pyridin-3-yl}-2,4-difluoro-benzenesulfonamide |
| I-18 | 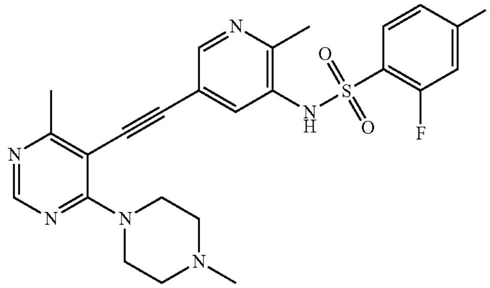 | 2,4-Difluoro-N-{2-methyl-5-[4-methyl-6-(4-methyl-piperazin-1-yl)-pyrimidin-5-ylethynyl]-pyridin-3-yl}-benzenesulfonamide |
| I-21 | 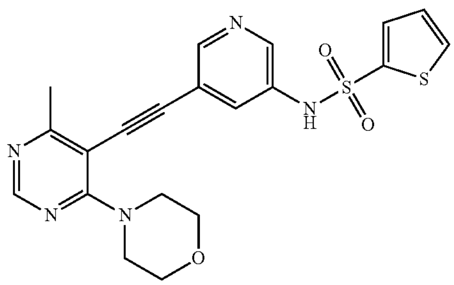 | Thiophene-2-sulfonic acid [5-(4-methyl-6-morpholin-4-yl-pyrimidin-5-ylethynyl)-pyridin-3-yl]-amide |
| I-22 | 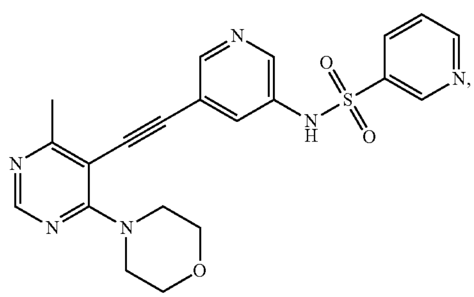 [SMILES: Cc1ncnc(N2CCOCC2)c1C#Cc1cncc(NS(=O)(=O)c2cccnc2)c1] | Pyridine-3-sulfonic acid [5-(4-methyl-6-morpholin-4-yl-pyrimidin-5-ylethynyl)-pyridin-3-yl]-amide |
| I-23 | 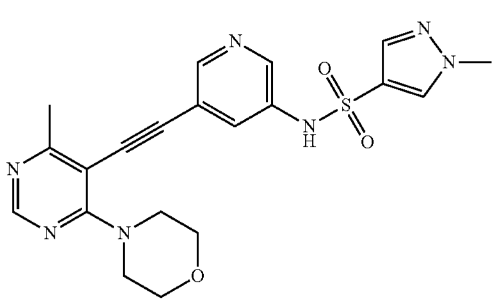 | 1-Methyl-1H-pyrazole-4-sulfonic acid [5-(4-methyl-6-morpholin-4-yl-pyrimidin-5-ylethynyl)-pyridin-3-yl]-amide |

-continued

| Ex. # | Molecular Structure | Name |
|---|---|---|
| I-24 | 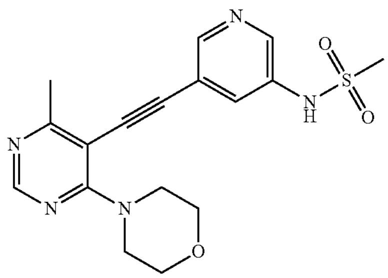 | N-[5-(4-Methyl-6-morpholin-4-yl-pyrimidin-5-ylethynyl)-pyridin-3-yl]-methanesulfonamide |
| I-25 | 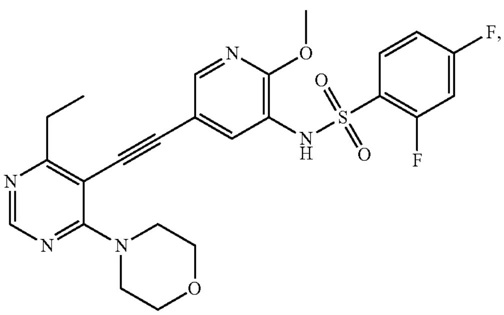 [SMILES: CCc1ncnc(N2CCOCC2)c1C#Cc1cnc(OC)c(NS(=O)(=O)c2ccc(F)cc2F)c1] | N-[5-(4-Ethyl-6-morpholin-4-yl-pyrimidin-5-ylethynyl)-2-methoxy-pyridin-3-yl]-2,4-difluoro-benzenesulfonamide |
| I-26 | 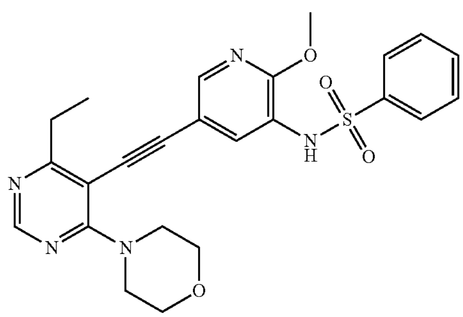 | N-[5-(4-Ethyl-6-morpholin-4-yl-pyrimidin-5-ylethynyl)-2-methoxy-pyridin-3-yl]-benzenesulfonamide |
| I-27 | 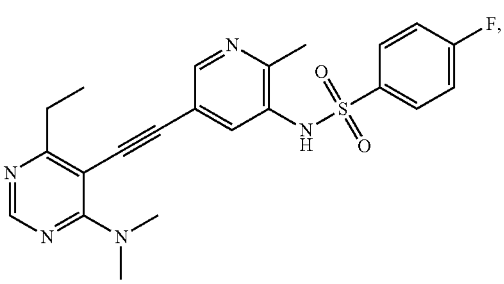 [SMILES: CCc1ncnc(N(C)C)c1C#Cc1cnc(C)c(NS(=O)(=O)c2ccc(F)cc2)c1] | N-[5-(4-Dimethylamino-6-ethyl-pyrimidin-5-ylethynyl)-2-methyl-pyridin-3-yl]-4-fluoro-benzenesulfonamide |
| I-28 | 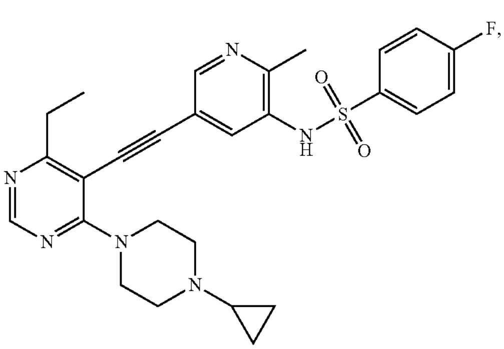 [SMILES: CCc1ncnc(N2CCN(C3CC3)CC2)c1C#Cc1cnc(C)c(NS(=O)(=O)c2ccc(F)cc2)c1] | N-{5-[4-(4-Cyclopropyl-piperazin-1-yl)-6-ethyl-pyrimidin-5-ylethynyl]-2-methyl-pyridin-3-yl}-4-fluoro-benzenesulfonamide |

-continued

| Ex. # | Molecular Structure | Name |
|---|---|---|
| I-29 | 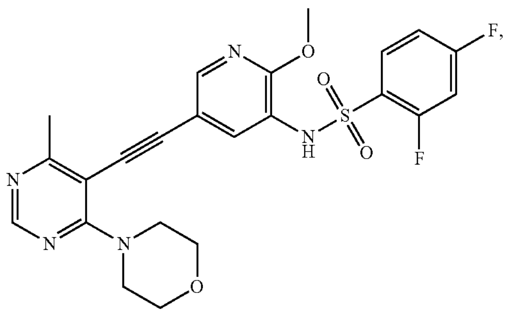 [SMILES: COc1ncc(C#Cc2c(C)ncnc2N2CCOCC2)cc1NS(=O)(=O)c1ccc(F)cc1F] | 2,4-Difluoro-N-[2-methoxy-5-(4-methyl-6-morpholin-4-yl-pyrimidin-5-ylethynyl)-pyridin-3-yl]-benzenesulfonamide |
| I-30 | 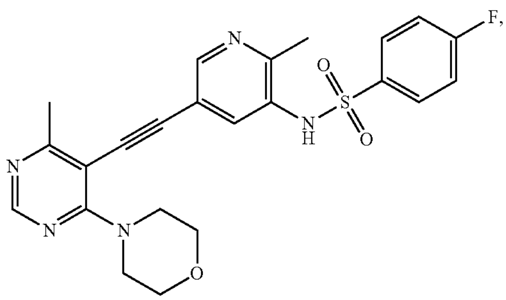 [SMILES: Cc1ncc(C#Cc2c(C)ncnc2N2CCOCC2)cc1NS(=O)(=O)c1ccc(F)cc1] | 4-Fluoro-N-[2-methyl-5-(4-methyl-6-morpholin-4-yl-pyrimidin-5-ylethynyl)-pyridin-3-yl]-benzenesulfonamide |
| I-31 | 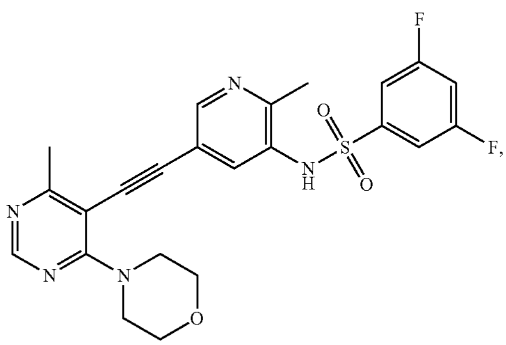 [SMILES: Cc1ncc(C#Cc2c(C)ncnc2N2CCOCC2)cc1NS(=O)(=O)c1cc(F)cc(F)c1] | 3,5-Difluoro-N-[2-methyl-5-(4-methyl-6-morpholin-4-yl-pyrimidin-5-ylethynyl)-pyridin-3-yl]-benzenesulfonamide |
| I-32 | 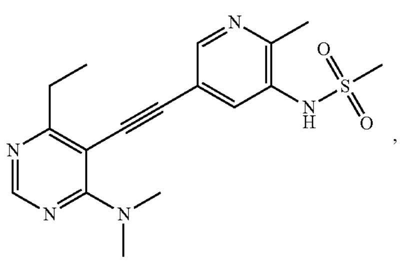 [SMILES: CCc1ncnc(N(C)C)c1C#Cc1cnc(C)c(NS(C)(=O)=O)c1] | N-[5-(4-Dimethylamino-6-ethyl-pyrimidin-5-ylethynyl)-2-methyl-pyridin-3-yl]-methanesulfonamide |
| I-33 | 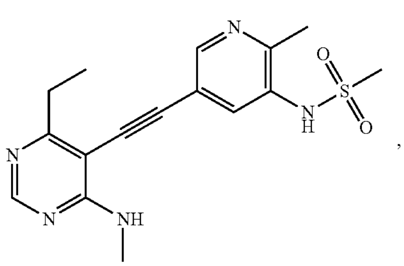 [SMILES: CCc1ncnc(NC)c1C#Cc1cnc(C)c(NS(C)(=O)=O)c1] | N-[5-(4-Ethyl-6-methylamino-pyrimidin-5-ylethynyl)-2-methyl-pyridin-3-yl]-methanesulfonamide |

| Ex. # | Molecular Structure | Name |
|---|---|---|
| I-34 | 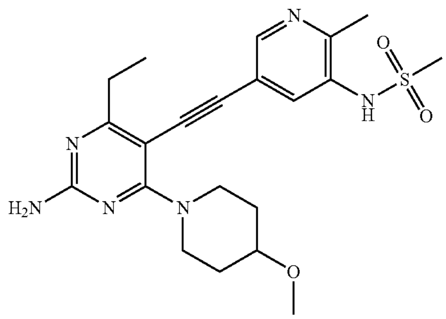 | N-{5-[2-Amino-4-ethyl-6-(4-methoxy-piperidin-1-yl)-pyrimidin-5-ylethynyl]-2-methyl-pyridin-3-yl}-methanesulfonamide |
| I-35 | 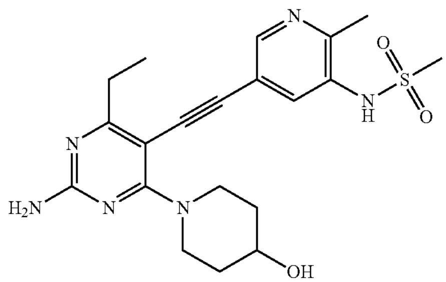 | N-{5-[2-Amino-4-ethyl-6-(4-hydroxy-piperidin-1-yl)-pyrimidin-5-ylethynyl]-2-methyl-pyridin-3-yl}-methanesulfonamide |
| I-36 | 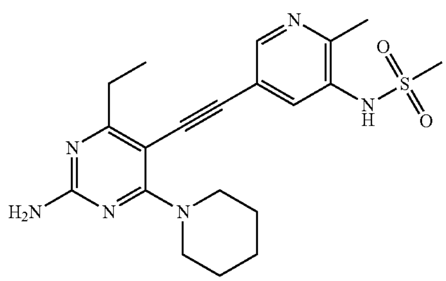 | N-[5-(2-Amino-4-ethyl-6-piperidin-1-yl-pyrimidin-5-ylethynyl)-2-methyl-pyridin-3-yl]-methanesulfonamide |
| I-37 | 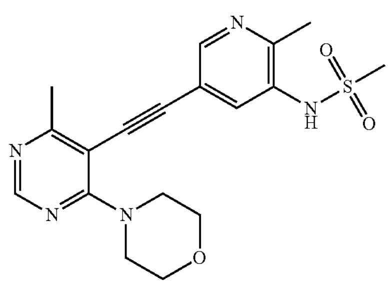 | N-[2-Methyl-5-(4-methyl-6-morpholin-4-yl-pyrimidin-5-ylethynyl)-pyridin-3-yl]-methanesulfonamide |
| I-38 | 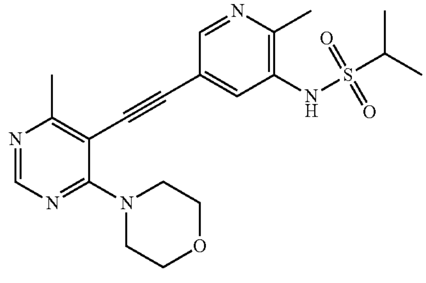 | Propane-2-sulfonic acid [2-methyl-5-(4-methyl-6-morpholin-4-yl-pyrimidin-5-ylethynyl)-pyridin-3-yl]-amide |

| Ex. # | Molecular Structure | Name |
|---|---|---|
| I-39 | 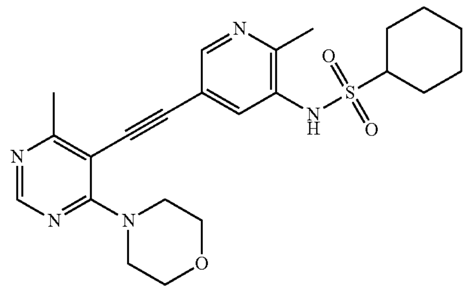 | Cyclohexanesulfonic acid [2-methyl-5-(4-methyl-6-morpholin-4-yl-pyrimidin-5-ylethynyl)-pyridin-3-yl]-amide |
| I-40 | 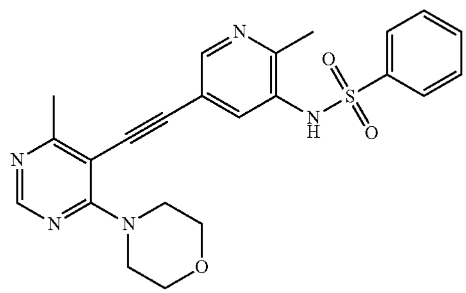 | N-[2-Methyl-5-(4-methyl-6-morpholin-4-yl-pyrimidin-5-ylethynyl)-pyridin-3-yl]-benzenesulfonamide |
| I-41 | 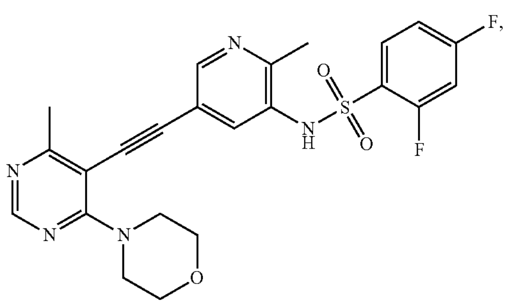 [SMILES: Cc1ncc(C#Cc2c(C)ncnc2N2CCOCC2)cc1NS(=O)(=O)c1ccc(F)cc1F] | 2,4-Difluoro-N-[2-methyl-5-(4-methyl-6-morpholin-4-yl-pyrimidin-5-ylethynyl)-pyridin-3-yl]-benzenesulfonamide |
| I-42 | 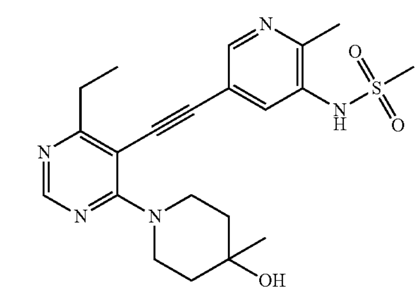 | N-{5-[4-Ethyl-6-(4-hydroxy-4-methyl-piperidin-1-yl)-pyrimidin-5-ylethynyl]-2-methyl-pyridin-3-yl}-methanesulfonamide |
| I-43 | 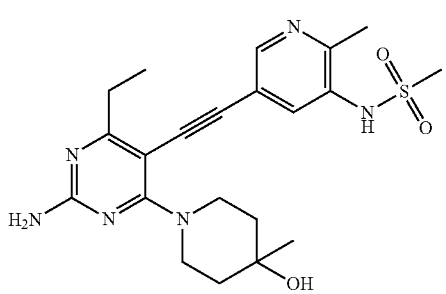 | N-{5-[2-Amino-4-ethyl-6-(4-hydroxy-4-methyl-piperidin-1-yl)-pyrimidin-5-ylethynyl]-2-methyl-pyridin-3-yl}-methanesulfonamide |

| Ex. # | Molecular Structure | Name |
|---|---|---|
| I-44 | 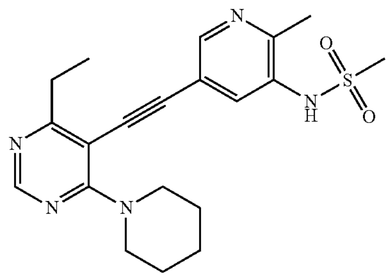 | N-[5-(4-Ethyl-6-piperidin-1-yl-pyrimidin-5-ylethynyl)-2-methyl-pyridin-3-yl]-methanesulfonamide |
| I-45 | 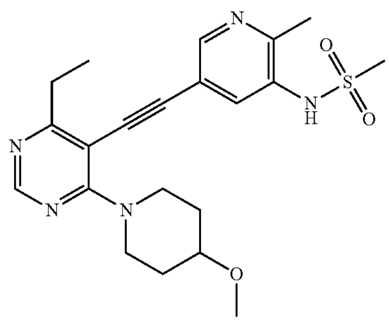 | N-{5-[4-Ethyl-6-(4-methoxy-piperidin-1-yl)-pyrimidin-5-ylethynyl]-2-methyl-pyridin-3-yl}-methanesulfonamide |
| I-46 | 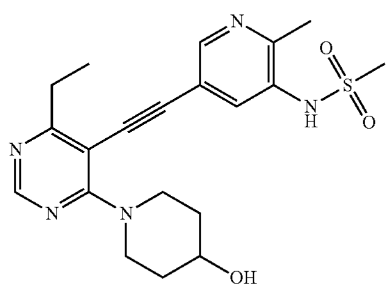 | N-{5-[4-Ethyl-6-(4-hydroxy-piperidin-1-yl)-pyrimidin-5-ylethynyl]-2-methyl-pyridin-3-yl}-methanesulfonamide |
| I-47 | 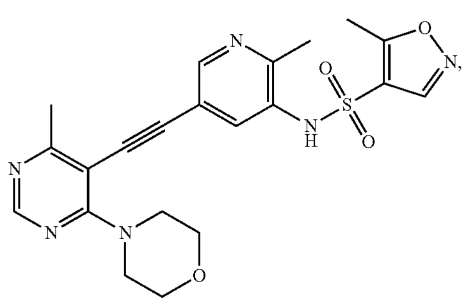 | 5-Methyl-isoxazole-4-sulfonic acid [2-methyl-5-(4-methyl-6-morpholin-4-yl-pyrimidin-5-ylethynyl)-pyridin-3-yl]-amide |
| I-48 | 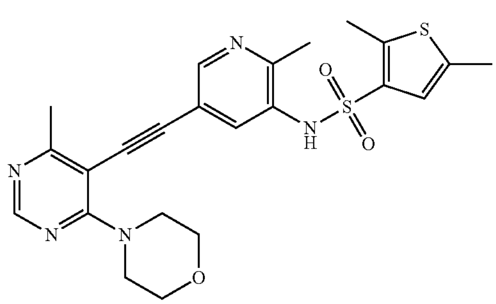 | 2,5-Dimethyl-thiophene-3-sulfonic acid [2-methyl-5-(4-methyl-6-morpholin-4-yl-pyrimidin-5-ylethynyl)-pyridin-3-yl]-amide |

-continued

| Ex. # | Molecular Structure | Name |
|---|---|---|
| I-49 | 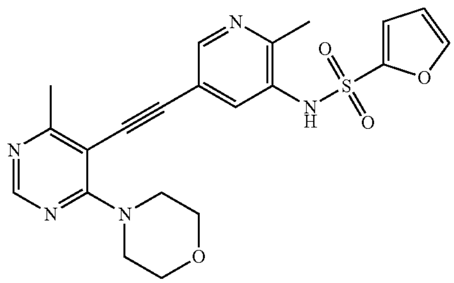 | Furan-2-sulfonic acid [2-methyl-5-(4-methyl-6-morpholin-4-yl-pyrimidin-5-ylethynyl)-pyridin-3-yl]-amide |
| I-50 | 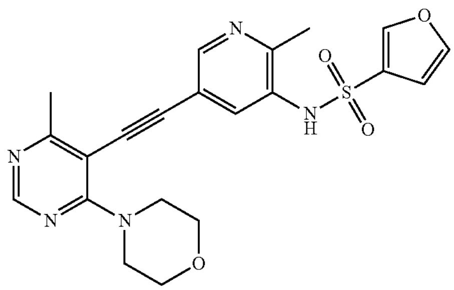 | Furan-3-sulfonic acid [2-methyl-5-(4-methyl-6-morpholin-4-yl-pyrimidin-5-ylethynyl)-pyridin-3-yl]-amide |
| I-51 | 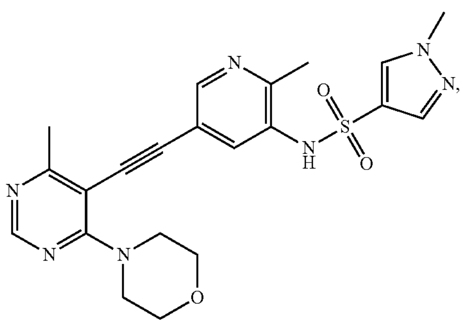 [SMILES: Cc1ncc(C#Cc2c(C)ncnc2N2CCOCC2)cc1NS(=O)(=O)c1cnn(C)c1] | 1-Methyl-1H-pyrazole-4-sulfonic acid [2-methyl-5-(4-methyl-6-morpholin-4-yl-pyrimidin-5-ylethynyl)-pyridin-3-yl]-amide |
| I-52 | 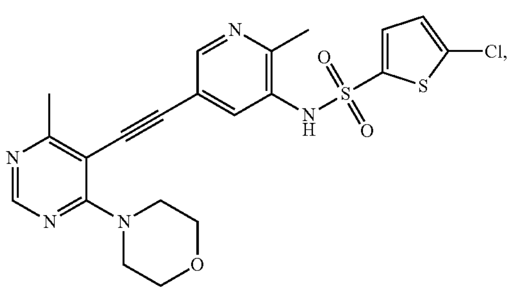 [SMILES: Cc1ncc(C#Cc2c(C)ncnc2N2CCOCC2)cc1NS(=O)(=O)c1ccc(Cl)s1] | 5-Chloro-thiophene-2-sulfonic acid [2-methyl-5-(4-methyl-6-morpholin-4-yl-pyrimidin-5-ylethynyl)-pyridin-3-yl]-amide |
| I-53 | 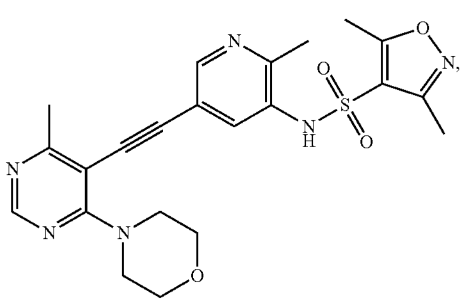 [SMILES: Cc1ncc(C#Cc2c(C)ncnc2N2CCOCC2)cc1NS(=O)(=O)c1c(C)noc1C] | 3,5-Dimethyl-isoxazole-4-sulfonic acid [2-methyl-5-(4-methyl-6-morpholin-4-yl-pyrimidin-5-ylethynyl)-pyridin-3-yl]-amide |

| Ex. # | Molecular Structure | Name |
|---|---|---|
| I-54 | 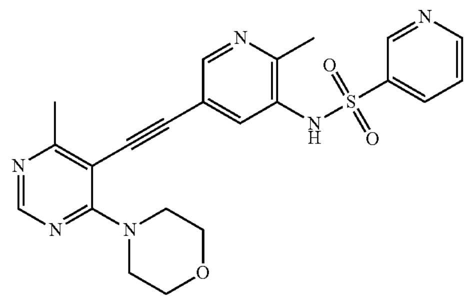 | Pyridine-3-sulfonic acid [2-methyl-5-(4-methyl-6-morpholin-4-yl-pyrimidin-5-ylethynyl)-pyridin-3-yl]-amide |
| I-55 | 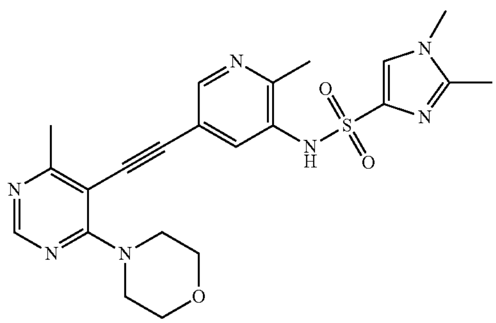 | 1,2-Dimethyl-1H-imidazole-4-sulfonic acid [2-methyl-5-(4-methyl-6-morpholin-4-yl-pyrimidin-5-ylethynyl)-pyridin-3-yl]-amide |
| I-56 | 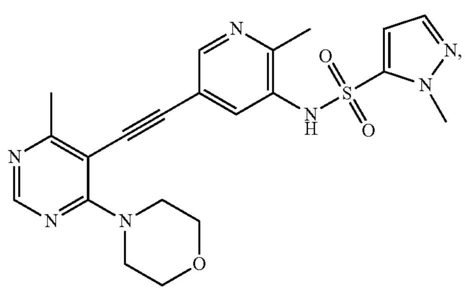 [SMILES: Cc1ncc(C#Cc2c(C)ncnc2N2CCOCC2)cc1NS(=O)(=O)c1ccnn1C] | 2-Methyl-2H-pyrazole-3-sulfonic acid [2-methyl-5-(4-methyl-6-morpholin-4-yl-pyrimidin-5-ylethynyl)-pyridin-3-yl]-amide |
| I-57 | 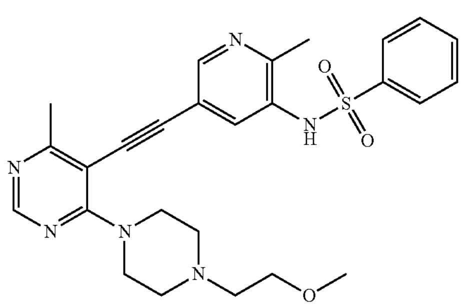 | N-(5-{4-[4-(2-Methoxy-ethyl)-piperazin-1-yl]-6-methyl-pyrimidin-5-ylethynyl}-2-methyl-pyridin-3-yl)-benzenesulfonamide |
| I-58 | 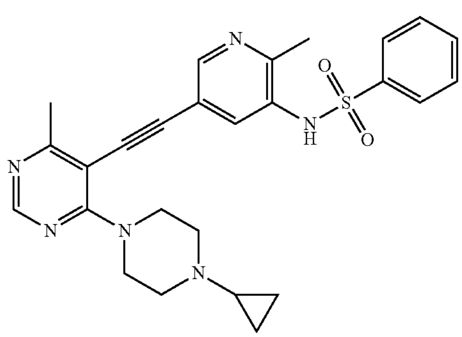 | N-{5-[4-(4-Cyclopropyl-piperazin-1-yl)-6-methyl-pyrimidin-5-ylethynyl]-2-methyl-pyridin-3-yl}-benzenesulfonamide |

-continued

| Ex. # | Molecular Structure | Name |
|---|---|---|
| I-59 | 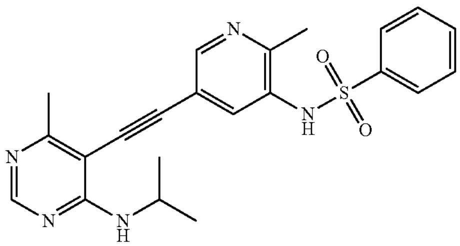 | N-[5-(4-Isopropylamino-6-methyl-pyrimidin-5-ylethynyl)-2-methyl-pyridin-3-yl]-benzenesulfonamide |
| I-60 | 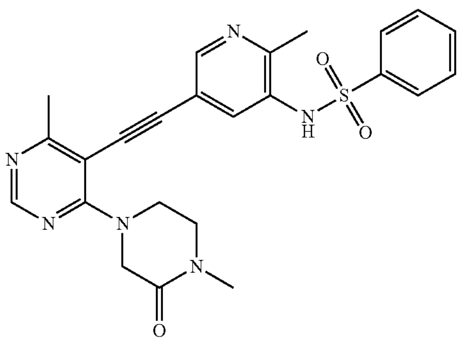 | N-{2-Methyl-5-[4-methyl-6-(4-methyl-3-oxo-piperazin-1-yl)-pyrimidin-5-ylethynyl]-pyridin-3-yl}-benzenesulfonamide |
| I-61 | 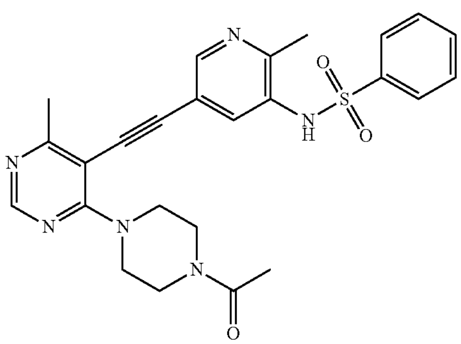 | N-{5-[4-(4-Acetyl-piperazin-1-yl)-6-methyl-pyrimidin-5-ylethynyl]-2-methyl-pyridin-3-yl}-benzenesulfonamide |
| I-62 | 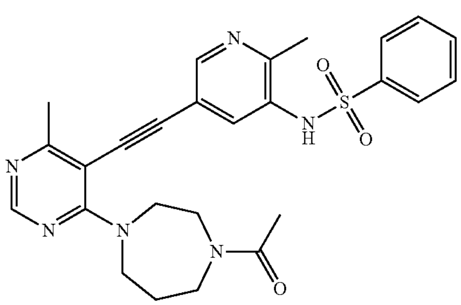 | N-{5-[4-(4-Acetyl-[1,4]diazepan-1-yl)-6-methyl-pyrimidin-5-ylethynyl]-2-methyl-pyridin-3-yl}-benzenesulfonamide |
| I-63 | 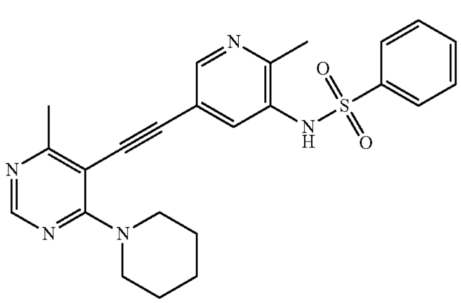 | N-[2-Methyl-5-(4-methyl-6-piperidin-1-yl-pyrimidin-5-ylethynyl)-pyridin-3-yl]-benzenesulfonamide |

| Ex. # | Molecular Structure | Name |
|---|---|---|
| I-64 | 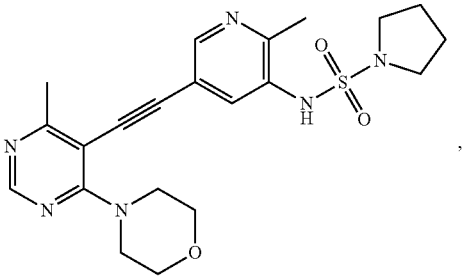 [SMILES: Cc1ncc(C#Cc2c(C)ncnc2N2CCOCC2)cc1NS(=O)(=O)N1CCCC1] | Pyrrolidine-1-sulfonic acid [2-methyl-5-(4-methyl-6-morpholin-4-yl-pyrimidin-5-ylethynyl)-pyridin-3-yl]-amide |
| I-65 | 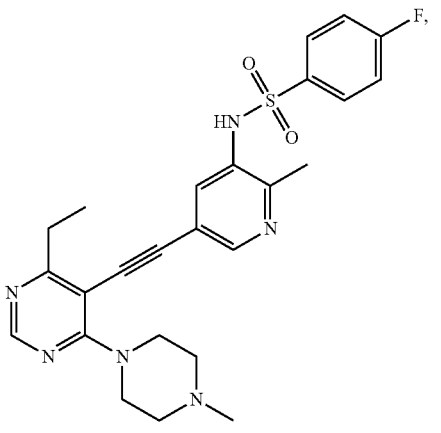 [SMILES: CCc1ncnc(N2CCN(C)CC2)c1C#Cc1cnc(C)c(NS(=O)(=O)c2ccc(F)cc2)c1] | N-{5-[4-Ethyl-6-(4-methyl-piperazin-1-yl)-pyrimidin-5-ylethynyl]-2-methyl-pyridin-3-yl}-4-fluoro-benzenesulfonamide |
| I-66 | 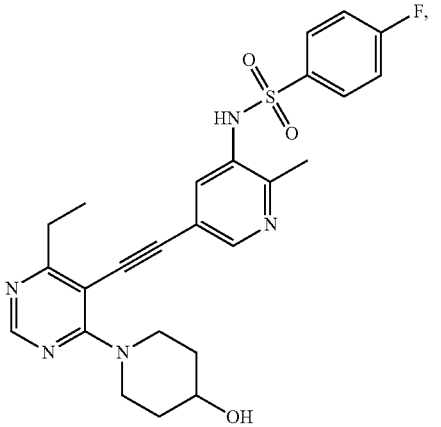 [SMILES: CCc1ncnc(N2CCC(O)CC2)c1C#Cc1cnc(C)c(NS(=O)(=O)c2ccc(F)cc2)c1] | N-{5-[4-Ethyl-6-(4-hydroxy-piperidin-1-yl)-pyrimidin-5-ylethynyl]-2-methyl-pyridin-3-yl}-4-fluoro-benzenesulfonamide |
| I-67 | 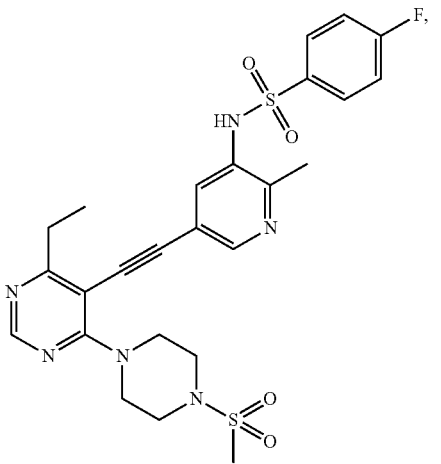 [SMILES: CCc1ncnc(N2CCN(S(C)(=O)=O)CC2)c1C#Cc1cnc(C)c(NS(=O)(=O)c2ccc(F)cc2)c1] | N-{5-[4-Ethyl-6-(4-methanesulfonyl-piperazin-1-yl)-pyrimidin-5-ylethynyl]-2-methyl-pyridin-3-yl}-4-fluoro-benzenesulfonamide |

| Ex. # | Molecular Structure | | Name |
|---|---|---|---|
| I-68 | 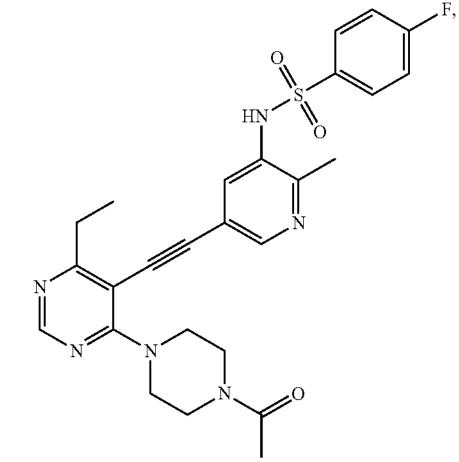 [SMILES: CCc1ncnc(N2CCN(C(C)=O)CC2)c1C#Cc1cnc(C)c(NS(=O)(=O)c2ccc(F)cc2)c1] | | N-{5-[4-(4-Acetyl-piperazin-1-yl)-6-ethyl-pyrimidin-5-ylethynyl]-2-methyl-pyridin-3-yl}-4-fluoro-benzenesulfonamide |
| I-69 | 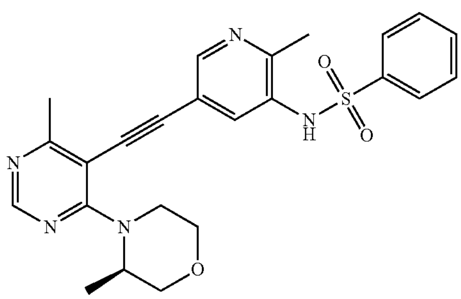 | Chiral | N-{2-Methyl-5-[4-methyl-6-((R)-3-methyl-morpholin-4-yl)-pyrimidin-5-ylethynyl]-pyridin-3-yl}-benzenesulfonamide |
| I-70 | 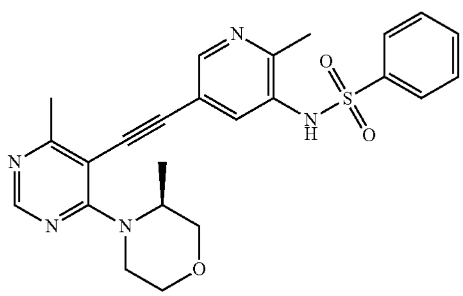 | Chiral | N-{2-Methyl-5-[4-methyl-6-((S)-3-methyl-morpholin-4-yl)-pyrimidin-5-ylethynyl]-pyridin-3-yl}-benzenesulfonamide |
| I-71 | 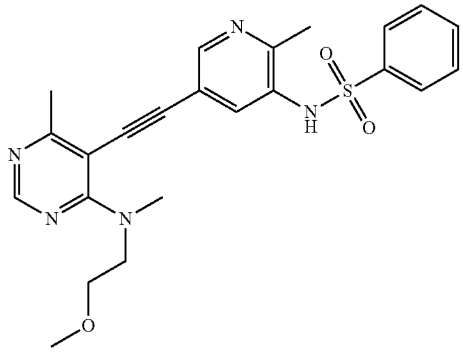 | | N-(5-{4-[(2-Methoxy-ethyl)-methyl-amino]-6-methyl-pyrimidin-5-ylethynyl}-2-methyl-pyridin-3-yl)-benzenesulfonamide |

| Ex. # | Molecular Structure | Name |
|---|---|---|
| I-72 | 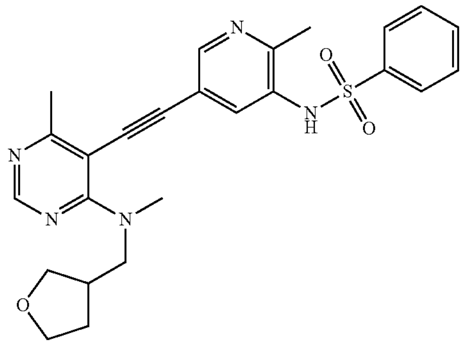 | N-(2-Methyl-5-{4-methyl-6-[methyl-(tetrahydro-furan-3-ylmethyl)-amino]-pyrimidin-5-ylethynyl}-pyridin-3-yl)-benzenesulfonamide |
| I-73 | 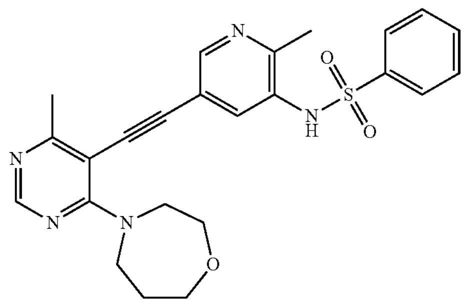 | N-[2-Methyl-5-(4-methyl-6-[1,4]oxazepan-4-yl-pyrimidin-5-ylethynyl)-pyridin-3-yl]-benzenesulfonamide |
| I-74 | 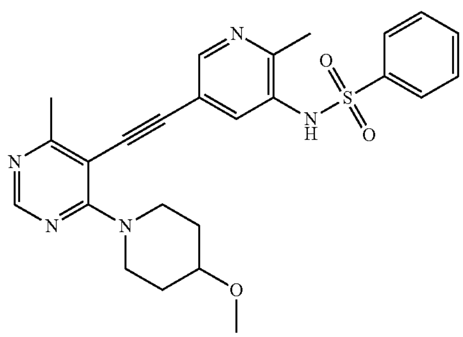 | N-{5-[4-(4-Methoxy-piperidin-1-yl)-6-methyl-pyrimidin-5-ylethynyl]-2-methyl-pyridin-3-yl}-benzenesulfonamide |
| I-75 | 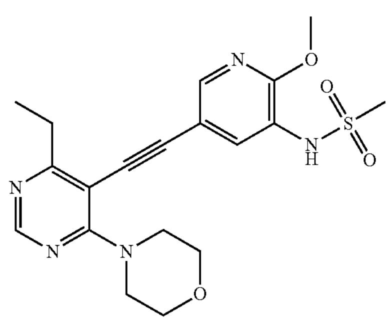 | N-[5-(4-Ethyl-6-morpholin-4-yl-pyrimidin-5-ylethynyl)-2-methoxy-pyridin-3-yl]-methanesulfonamide |
| I-76 | 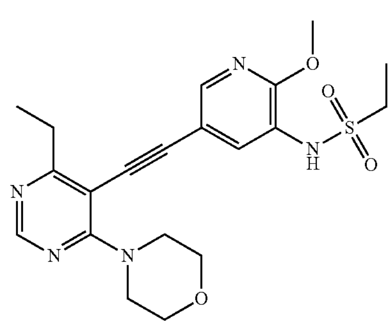 | Ethanesulfonic acid [5-(4-ethyl-6-morpholin-4-yl-pyrimidin-5-ylethynyl)-2-methoxy-pyridin-3-yl]-amide |

-continued

| Ex. # | Molecular Structure | Name |
|---|---|---|
| I-77 | 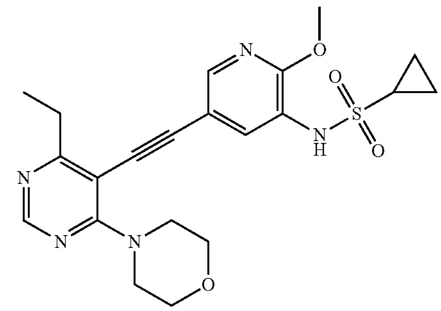 | Cyclopropanesulfonic acid [5-(4-ethyl-6-morpholin-4-yl-pyrimidin-5-ylethynyl)-2-methoxy-pyridin-3-yl]-amide |
| I-78 | 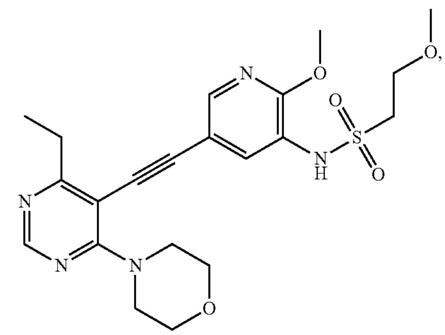 [SMILES: CCc1ncnc(N2CCOCC2)c1C#Cc1cnc(OC)c(NS(=O)(=O)CCOC)c1] | 2-Methoxy-ethanesulfonic acid [5-(4-ethyl-6-morpholin-4-yl-pyrimidin-5-ylethynyl)-2-methoxy-pyridin-3-yl]-amide |
| I-79 | 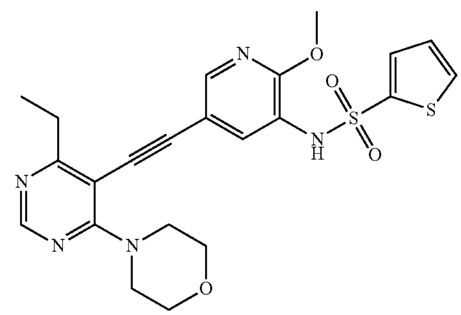 | Thiophene-2-sulfonic acid [5-(4-ethyl-6-morpholin-4-yl-pyrimidin-5-ylethynyl)-2-methoxy-pyridin-3-yl]-amide |
| I-80 | 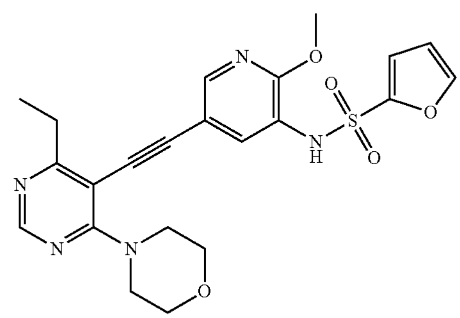 | Furan-2-sulfonic acid [5-(4-ethyl-6-morpholin-4-yl-pyrimidin-5-ylethynyl)-2-methoxy-pyridin-3-yl]-amide |
| I-81 | 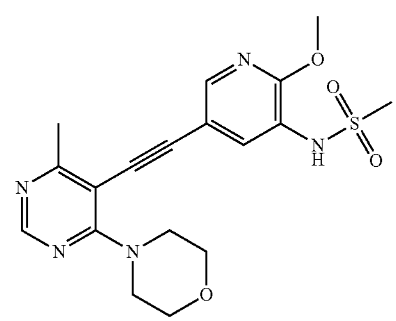 | N-[2-methoxy-5-(4-methyl-6-morpholin-4-yl-pyrimidin-5-ylethynyl)-pyridin-3-yl]-methylsulfonamide |

| Ex. # | Molecular Structure | Name |
|---|---|---|
| I-82 | 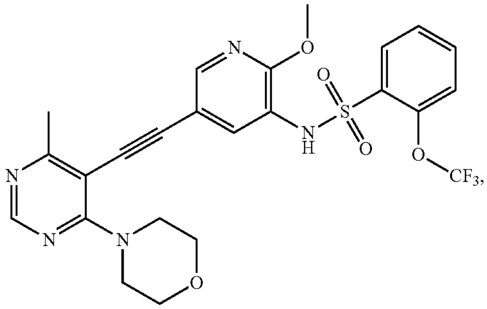 [SMILES: COc1ncc(C#Cc2c(C)ncnc2N2CCOCC2)cc1NS(=O)(=O)c1ccccc1OC(F)(F)F] | 2-Trifluoromethoxy-N-[2-methoxy-5-(4-methyl-6-morpholin-4-yl-pyrimidin-5-ylethynyl)-pyridin-3-yl]-benzenesulfonamide |
| I-83 | 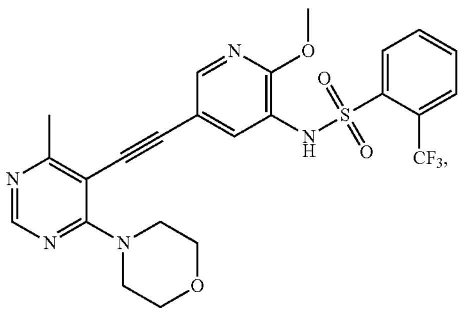 [SMILES: COc1ncc(C#Cc2c(C)ncnc2N2CCOCC2)cc1NS(=O)(=O)c1ccccc1C(F)(F)F] | 2-Trifluoromethyl-N-[2-methoxy-5-(4-methyl-6-morpholin-4-yl-pyrimidin-5-ylethynyl)-pyridin-3-yl]-benzenesulfonamide |
| I-84 | 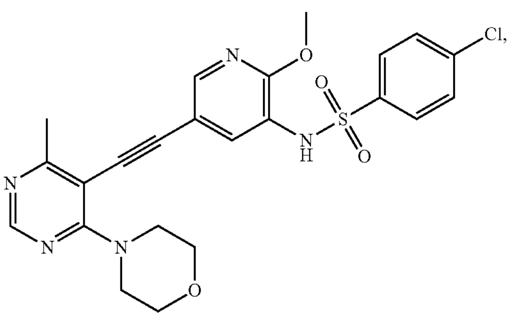 [SMILES: COc1ncc(C#Cc2c(C)ncnc2N2CCOCC2)cc1NS(=O)(=O)c1ccc(Cl)cc1] | 4-Chloro-N-[2-methoxy-5-(4-methyl-6-morpholin-4-yl-pyrimidin-5-ylethynyl)-pyridin-3-yl]-benzenesulfonamide |
| I-85 | 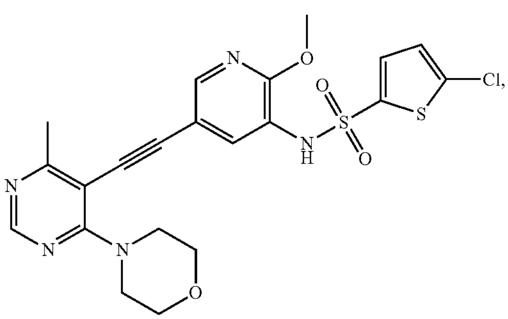 [SMILES: COc1ncc(C#Cc2c(C)ncnc2N2CCOCC2)cc1NS(=O)(=O)c1ccc(Cl)s1] | 5-Chloro-N-[2-methoxy-5-(4-methyl-6-morpholin-4-yl-pyrimidin-5-ylethynyl)-pyridin-3-yl]-thiophene-2-sulfonamide |
| I-86 | 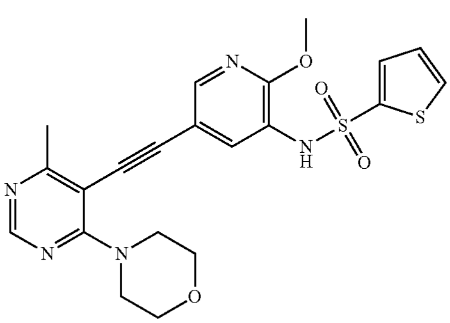 | N-[2-Methoxy-5-(4-methyl-6-morpholin-4-yl-pyrimidin-5-ylethynyl)-pyridin-3-yl]-thiophene-2-sulfonamide |

-continued

| Ex. # | Molecular Structure | Name |
|---|---|---|
| I-87 | 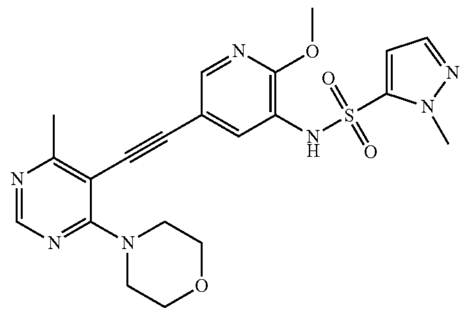 [SMILES: COc1ncc(C#Cc2c(C)ncnc2N2CCOCC2)cc1NS(=O)(=O)c1ccnn1C] | N-[2-methoxy-5-[2-(4-methyl-6-morpholin-4-ylpyrimidin-5-yl)ethynyl]pyridin-3-yl]-2-methylpyrazole-3-sulfonamide |
| I-88 | 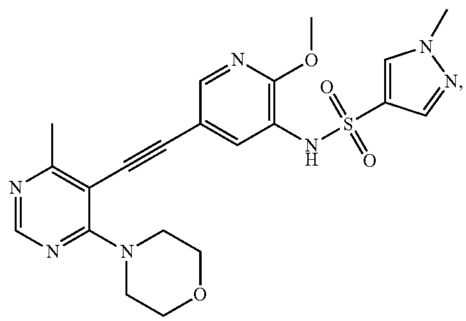 | N-[2-methoxy-5-[2-(4-methyl-6-morpholin-4-ylpyrimidin-5-yl)ethynyl]pyridin-3-yl]-1-methylpyrazole-4-sulfonamide |
| I-89 | 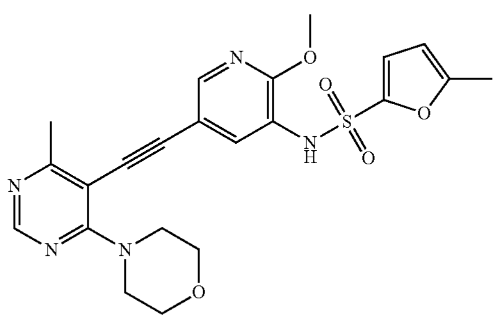 | N-[2-methoxy-5-[2-(4-methyl-6-morpholin-4-ylpyrimidin-5-yl)ethynyl]pyridin-3-yl]-5-methylfuran-2-sulfonamide |

\* \* \* \* \*